(12) United States Patent
Sukerkar et al.

US008580231B2

(10) Patent No.: US 8,580,231 B2
(45) Date of Patent: Nov. 12, 2013

(54) COMPOSITIONS AND METHODS COMPRISING MAGNETIC RESONANCE CONTRAST AGENTS

(75) Inventors: Preeti A. Sukerkar, Glenview, IL (US); Jiyoun Lee, Palo Alto, CA (US); Teresa K. Woodruff, Chicago, IL (US); Thomas J. Meade, Wilmette, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/551,344

(22) Filed: Jul. 17, 2012

(65) Prior Publication Data

US 2013/0011340 A1 Jan. 10, 2013

Related U.S. Application Data

(63) Continuation-in-part of application No. 12/471,731, filed on May 26, 2009, now abandoned.

(60) Provisional application No. 61/055,629, filed on May 23, 2008.

(51) Int. Cl.
*A61K 31/57* (2006.01)
*C01F 17/00* (2006.01)
*A61K 49/10* (2006.01)
*C07J 1/00* (2006.01)

(52) U.S. Cl.
CPC .............. *A61K 49/106* (2013.01); *A61K 31/57* (2013.01); *C01F 17/00* (2013.01); *C07J 1/0003* (2013.01)
USPC ........ 424/9.363; 324/309; 423/263; 540/465; 568/371

(58) Field of Classification Search
None
See application file for complete search history.

(56) References Cited

U.S. PATENT DOCUMENTS

| 4,885,363 | A | 12/1989 | Tweedle et al. |
| 5,087,440 | A | 2/1992 | Cacheris et al. |
| 5,155,215 | A | 10/1992 | Ranney |
| 5,188,816 | A | 2/1993 | Sherry et al. |
| 5,219,553 | A | 6/1993 | Kraft et al. |
| 5,262,532 | A | 11/1993 | Tweedle et al. |
| 5,358,704 | A | 10/1994 | Desreux et al. |
| 5,707,605 | A | 1/1998 | Meade et al. |
| 5,980,862 | A | 11/1999 | Meade et al. |
| 6,656,450 | B2 | 12/2003 | Hubin et al. |
| 6,713,045 | B1 | 3/2004 | Meade et al. |
| 6,770,261 | B2 | 8/2004 | Meade et al. |
| 7,029,655 | B2 | 4/2006 | Allen et al. |
| 7,354,568 | B1 | 4/2008 | Meade et al. |
| 2002/0197648 | A1 | 12/2002 | Silva et al. |
| 2003/0004236 | A1 | 1/2003 | Meade |
| 2003/0021750 | A1 | 1/2003 | Bakan et al. |
| 2003/0135108 | A1 | 7/2003 | Silva et al. |
| 2003/0198597 | A1 | 10/2003 | Meade et al. |
| 2004/0146463 | A1* | 7/2004 | Meade et al. ............... 424/9.323 |
| 2004/0170563 | A1 | 9/2004 | Meade |
| 2004/0209317 | A1* | 10/2004 | Ting ................................ 435/7.5 |
| 2005/0002866 | A1 | 1/2005 | Meade et al. |
| 2006/0088475 | A1 | 4/2006 | Duimstra et al. |
| 2009/0196829 | A1* | 8/2009 | Song et al. ................... 424/9.35 |

OTHER PUBLICATIONS

PA Sukerkar, KW MacRenaris, TR Townsend, RA Ahmed, JE Burdette, TJ Meade. "Synthesis and Biological Evaluation of Water-Soluble Progesterone-Conjugated Probes for Magnetic Resonance Imaging of Hormone Related Cancers." Bioconjugate Chemistry, vol. 22(11), 2011, pp. 2304-2316, published Oct. 5, 2011.*
Madauss et al. "Progesterone receptor ligand binding pocket flexibility: crystal structures of the norethindrone and mometasone furoate complexes" J Med Chem, 2004, 47: 3381-3387.
Major et al. "Bioresponsive, Cell-Penetrating and Multimeric MR Contrast Agents," Acc Chem Res, 2009, 42: 893-903.
Mankoff et al. "Tumor receptor imaging," J Nucl Med, 2008, 49 (Suppl 2): 149S-163S.
Marik et al. "Click for PET: rapid preparation of [18F]fluoropeptides using CuI catalyzed 1,3-dipolar cycloaddition," Tetrahedron Lett, 2006, 47: 6681-6684.
Meade et al. "New magnetic resonance contrast agents as biochemical reporters," Curr Opin Neurobiol, 2003, 13: 597-602.
Merbach & Toth (2001).The Chemistry of Contrast Agents in Medical Magnetic Resonance Imaging, New York: John Wiley and Sons.
Meyer et al., "Advances in macrocyclic gadolinium complexes as magnetic resonance imaging contrast agents" Invest. Radiol., 1990 25:S53.
Minchinton et al. "Drug penetration in solid tumours," Nat Rev Cancer, 2006, 6: 583-592.
Miyamoto et al. "Significance of progesterone receptor-A and -B expressions in endometrial adenocarcinoma" J Steroid Biochem Mol Biol, 2004, 92, 111-8.
Montemurro & Aglietta, "Incorporating trastuzumab into the neoadjuvant treatment of HER2-overexpressing breast cancer" Clin Breast Cancer, 2005, 6, 77-80.
Muss "Endocrine therapy for advanced breast cancer: a review" Breast Cancer Res. Treat., 1992 , 21, 15-26.
Orlando et al. "Molecularly targeted endocrine therapies for breast cancer," Cancer Treat Rev, 2010, 36 (Suppl 3): S67-S71.
Osborne et al. "Endocrine responsiveness: understanding how progesterone receptor can be used to select endocrine therapy" Breast, 2005, 14, 458-65.
Pomper et al. "21-[ 18F]Fluoro-16α-ethyl-19-norprogesteron Synthesis and Target Tissue Selective Uptake of a Progestin Receptor Based Radiotracer for Positron Emission Tomography" J Med Chem, 1988, 31, 1360-3.
Prasuhn et al. "Viral MRI contrast agents: coordination of Gd by native virions and attachment of Gd complexes by azide-alkyne cycloaddition," Chem Commun (Camb.), 2007, 1269-1271.
Preda et al. "MRI monitoring of Avastin antiangiogenesis therapy using B22956/1, a new blood pool contrast agent, in an experimental model of human cancer" J Magn Reson Imaging, 2004, 20, 865-73.

(Continued)

*Primary Examiner* — Frederick Krass
*Assistant Examiner* — Isaac Shomer
(74) *Attorney, Agent, or Firm* — Casimir Jones, S.C.

(57) ABSTRACT

The present invention relates to compositions and methods for imaging with magnetic resonance contrast agents. In particular, the present invention provides targeted contrast agents for selective imaging.

10 Claims, 28 Drawing Sheets

(56) References Cited

OTHER PUBLICATIONS

Price et al. "Physicochemical drug properties associated with in vivo toxicological outcomes: a review," Expert Opin Drug Metab Toxicol, 2009, 5:921-931.
Pysz et al. "Molecular imaging: current status and emerging strategies," Clin Radiol, 2010, 65: 500-516.
Quici et al. "Visible and near-infrared intense luminescence from water-soluble lanthanide [Tb(III), Eu(III), Sm(III), Dy(III), Pr(III), Ho(III), Yb(III), Nd(III), Er(III)] complexes," Inorg Chem, 2005, 44: 529-537.
Rao "Mode of entry of steroid and thyroid hormones into cells" Mol. Cell. Endocrinol., 1981, 21, 97-108.
Roy et al. "Predictive value of (16 alpha[18-F]-fluoroestradiol) FES-PET in recurrent estrogen receptor positive (ER+) breast cancer," J Nucl Med Meeting Abst, 2010, 51 (Supplement 2): 56.
Saha et al. "Synthesis, in vitro progesterone receptors affinity of gadolinium containing mifepristone conjugates and estimation of binding sites in human breast cancer cells," Bioorg Med Chem, 2010, 18: 1891-1898.
Saito et al. "Progesterone receptor isoforms as a prognostic marker in human endometrial carcinoma" Cancer Sci, 2006, 97, 1308-14.
Shellock & Spinazzi, "MRI safety update 2008: part 1, MRI contrast agents and nephrogenic systemic fibrosis," AJR Am J Roentgenol, 2008, 191, 1129-39.
Shellock & Spinazzi, "MRI safety update 2008: part 2, screening patients for MRI," AJR Am J Roentgenol, 2008, 191, 1140-1149.
So et al., "Quantitative structure-activity relationship studies of progesterone receptor binding steroids" J. Chem. Inf. Comput. Sci., 2000, 40, 762-772.
Song et al. "Synthesis of multimeric MR contrast agents for cellular imaging," J Am Chem Soc, 2008, 130: 6662-6663.
Stasiuk et al. "Click chemistry with lanthanide complexes: a word of caution," Dalton Trans, 2009, 9725-9727.
Sukerkar et al. "A steroid-conjugated magnetic resonance probe enhances contrast in progesterone receptor expressing organs and tumors in vivo," Mol Pharmaceutics, 2011, 8: 1390-1400.
Tornoe et al. "Peptidotriazoles on solid phase: [1,2,3]-triazoles by regiospecific copper(i)-catalyzed 1,3-dipolar cycloadditions of terminal alkynes to azides," J Org Chem, 2002 67: 3057-3064.
Tozaki "Diagnosis of breast cancer: MDCT versus MRI" Breast Cancer, 2008, 15, 205-11.
Tunggal et al. "Penetration of anticancer drugs through solid tissue: a factor that limits the effectiveness of chemotherapy for solid tumors," Clin Cancer Res, 1999, 5: 1583-1586.
Uharcek "Prognostic factors in endometrial carcinoma" Obstet Gynaecol Res, 2008, 34, 776-83.
Verhagen et al. "Metabolism of a [18F]fluorine labeled progestin (21 -[18F]fluoro-16α -ethyl-19-norprogesterone) in humans: a clue for future investigations," Nucl Med Biol, 1994,21: 941-952.
Viguier et al. "A sensitized europium complex generated by micromolar concentrations of copper(I): toward the detection of copper(I) in biology," J Am Chem Soc, 2006, 128: 11370-11371.
Vijaykumar et al. "An efficient route for the preparation of a 21-fluoro progestin-16 alpha,17 alpha-dioxolane, a high-affinity ligand for PET imaging of the progesterone receptor" A. J Org Chem, 2002, 67, 4904-10.
Webb, "The Physics of Medical Imaging" 1993, Bristol, UK and Philadelphia: Institute of Physics Publishing.
Weissleder, "Molecular imaging in cancer," Science, 2006, 312: 1168-1171.
Weissleder, "Scaling down imaging: molecular mapping of cancer in mice," Nat Rev Cancer, 2002, 2: 11-18.
Williams et al. "Atomic structure of progesterone complexed with its receptor," Nature, 1998, 393: 392-396.
Yoshida et al. "The positron emission tomography with F18 17beta-estradiol has the potential to benefit diagnosis and treatment of endometrial cancer," Gynecol Oncol, 2007, 104: 764-766.
Zhou et al. "Bromine- and iodine-substituted 16alpha,17alpha-dioxolane progestins for breast tumor imaging and radiotherapy: synthesis and receptor binding affinity" J Med Chem, 2006, 49:4737-44.
Zhou et al. "Imaging progesterone receptor in breast tumors: Synthesis and receptor binding affinity of fluoroalkyl-substituted analogs of Tanaproget,"J Med Chem, 2010, 3349-3360.
Zong et al. "Contrast-enhanced MRI with new biodegradable macromolecular Gd(III) complexes in tumor-bearing mice" Magn Reson Med, 2005, 53: 835-42.
Sukerkar et al. "Synthesis and biological evaluation of water-soluble progesterone-conjugated probes for magnetic resonance imaging of hormone related cancers," Bioconjugate Chem, 2011, 22(11):2304-2316.
Ahmad et al. "Steroid hormone receptors in cancer development: a target for cancer therapeutics," Cancer Lett, 2011, 300: 1-9.
Aime et al. "Targeting cells with MR imaging probes based on paramagnetic Gd(III) chelates" Curr Pharm Biotechnol 2004, 5:509-18.
Allen & Meade "Magnetic resonance contrast agents for medical and molecular imaging" Met Ions Biol Syst, 2004, 42, 1-38.
Allen and Meade "Synthesis and visualization of a membrane-permeable MRI contrast agent" J. Biol. Inorg. Chem., 2003, 8:746-750.
Allen et al. "Cellular Delivery of MRI Contrast Agents" Chem. Biol., 2004, 11, 301-307.
Alvarez et al. "Correlation between log P and ClogP for Some Steroids" J. Pharm. Sci., 1997 86, 1187-1189.
Andre & Pusztai "Molecular classification of breast cancer: implications for selection of adjuvant chemotherapy" Nat. Clin. Pract. Oncol., 2006, 3, 621-632.
Arnett-Mansfield et al. "Relative expression of progesterone receptors A and B in endometrioid cancers of the endometrium" Cancer Res, 2001, 61, 4576-82.
Arpino et al. "Estrogen receptor-positive, progesterone receptor-negative breast cancer: association with growth factor receptor expression and tamoxifen resistance" J. Natl. Cancer Inst, 2005, 97, 1254-1261.
Artemov et al. "Magnetic resonance molecular imaging of the HER-2/neu receptor" Cancer Res., 2003, 63, 2723-2727.
Bardou et al. "Progesterone receptor status significantly improves outcome prediction over estrogen receptor status alone for adjuvant endocrine therapy in two large breast cancer databases" J. Clin. Oncol., 2003, 21, 1973-1979.
Beeby et al. "Non-radiative deactivation of the excited states of europium, terbium and ytterbium complexes by proximate energy-matched OH, NH and CH oscillators: an improved luminescence method for establishing solution hydration states," J Chem Soc, Perkin Trans. 2, 1999, 493-504.
Benard et al. "Imaging in breast cancer: Single-photon computed tomography and positron-emission tomography," Breast Cancer Res, 2005, 7:153-162.
Bhujwalla et al. "Vascular differences detected by MRI for metastatic versus nonmetastatic breast and prostate cancer xenografts" Neoplasia, 2001, 3, 143-53.
Boruban et al. "From endometrial hyperplasia to endometrial cancer: insight into the biology and possible medical preventive measures" Eur J Cancer Prev, 2008, 17, 133-8. abstract only provided.
Bryce et al. "Accumulation of an anthraquinone and its platinum complexes in cancer cell spheroids: the effect of charge on drug distribution in solid tumour models," Chem Commun (Camb.), 2009, 2673-2675.
Bursi & Groen "Application of (quantitative) structure-activity relationships to progestagens: from serendipity to structure-based design" Eur. J. Med. Chem., 2000, 35, 787-796.
Caravan et al. "Gadolinium(III) Chelates as MRI Contrast Agents: Structure, Dynamics, and Applications," Chem Rev, 1999, 99: 2293-2352.
Couture et al. "Human 20alpha-hydroxysteroid dehydrogenase: crystallographic and site-directed mutagenesis studies lead to the identification of an alternative binding site for C21-steroids," J Mol Biol, 2003, 593-604.
Cui et al. "Biology of progesterone receptor loss in breast cancer and its implications for endocrine therapy" J. Clin. Oncol., 2005, 23, 7721-7735.

(56) References Cited

OTHER PUBLICATIONS

Dehdashti et al. "Assessment of 21-[18F]fluoro-16 alpha-ethyl-19-norprogesterone as a positron-emitting radiopharmaceutical for the detection of progestin receptors in human breast carcinomas" J Nucl Med, 1991, 32, 1532-7.
Dehdashti et al. "Positron tomographic assessment of androgen receptors in prostatic carcinoma," Eur J Nucl Med Mol Imaging, 2005, 32: 344-350.
Duimstra et al. "A gadolinium chelate for detection of beta-glucuronidase: a self-immolative approach" 2005 J. Am. Chem. Soc. 127, 12847-12855.
Frullano et al. "Multimodal MRI contrast agents," J Biol Inorg Chem, 2007, 12: 939-949.
Fuqua et al. "Insights into the role of progesterone receptors in breast cancer" J Clin Oncol, 2005, 23, 931-2; author reply 932-3.
Gambhir "Molecular imaging of cancer with positron emission tomography," Nat Rev Cancer, 2002, 2:683-693.
Golub et al. ""Natural" progesterone: information on fetal effects" Birth Defects Res. B Dev. Reprod. Toxicol. , 2006, 77, 455-470.
Henze et al., "Characterization of 68Ga-DOTA-D-Phe1-Tyr3-Octreotide Kinetics in Patients with Meningiomas," 2005 J Nucl Med, 46:763-769.
Hoffman et al. "Characterization of New Estrogen Receptor Destabilizing Compounds: Effects on Estrogen-Sensitive and Tamoxifen-Resistant Breast Cancer" J Natl Cancer Inst, 2004, 96, 210-8.
Hopp et al. "Breast cancer patients with progesterone receptor PR-A-rich tumors have poorer disease-free survival rates" Clin. Cancer Res., 2004, 10, 2751-2760.
Ismail et al. "Progesterone involvement in breast development and tumorigenesis—as revealed by progesterone receptor "knockout" and "knockin" mouse models" Steroids, 2003, 68, 779-787.
Ito et al. "Biological roles of estrogen and progesterone in human endometrial carcinoma—new developments in potential endocrine therapy for endometrial cancer" Endocr J, 2007, 54, 667-79.
Jacobs & Cherry "Complementary emerging techniques: high-resolution PET and MRI" Curr. Opin. Neurobiol., 2001, 11, 621-629.
Jacobsen et al. "Expression profiling of human breast cancers and gene regulation by progesterone receptors" J Mammary Gland Biol Neoplasia, 2003 , 8, 257-68.
Kay "Nephrogenic systemic fibrosis: a gadolinium-associated fibrosing disorder in patients with renal dysfunction" Ann Rheum Dis, 2008, 67 Suppl 3, 66-9.
Kolb et al. "Click Chemistry: Diverse Chemical Function from a Few Good Reactions," Angew Chem Int Ed Engl, 2001, 40: 2004-2021.
Kurtkoti & Hiremagalur "Gadolinium and nephrogenic systemic fibrosis: association or causation" Nephrology, 2008, 13, 235-41.
Lanari & Molinolo "Progesterone receptors—animal models and cell signalling in breast cancer. Diverse activation pathways for the progesterone receptor: possible implications for breast biology and cancer" Breast Cancer Res., 2002 , 4, 240-243.
Lebedev et al. "Clickable bifunctional radiometal chelates for peptide labeling," Chem Commun (Camb.), 2010, 46: 1706-1708.
Lee et al. "Breast cancer screening in BRCA1 mutation carriers: effectiveness of MR imaging—Markov Monte Carlo decision analysis" Radiology, 2008, 246, 763-71.
Lee et al. "Development of [F-18]fluorine-substituted Tanaproget as a progesterone receptor imaging agent for positron emission tomography," Bioconjugate Chem, 2010, 21: 1096-1104.
Lee et al. "Rational design, synthesis, and biological evaluation of progesterone-modified MRI contrast agents," Chem Biol, 2007, 14: 824-834.
Lee et al., "A Steroid-Conjugated Contrast Agent for Magnetic Resonance Imaging of Cell Signaling" J. Am. Chem. Soc., 2005, 127:13164-13166.
Leeson et al. "The influence of drug-like concepts on decision-making in medicinal chemistry," Nat Rev Drug Discov, 2007, 6: 881-890.
Lehman et al. "MRI evaluation of the contralateral breast in women with recently diagnosed breast cancer" N Engl J Med, 2007, 356, 1295-303.
Leo et al. "Partition coefficients and their uses," Chem Rev, 1971, 71: 525-616.
Leo et al. "Some advantages of calculating octanol-water partition coefficients," J Pharm Sci, 1987, 76: 166-168.
Li et al. "Mechanistic studies of a calcium-dependent MRI contrast agent" Inorg. Chem., 2002, 41, 4018-4024.
Linden et al. "Quantitative fluoroestradiol positron emission tomography imaging predicts response to endocrine treatment in breast cancer," J Olin Oncol, 2006, 24: 2793-2799.
Louie et al. "In vivo visualization of gene expression using magnetic resonance imaging" Nat. Biotechnol., 2000, 18, 321-325.

\* cited by examiner

| B | $T_1$ at 50 μM (ms) | | |
|---|---|---|---|
| | Control | 1 | 2 |
| 231+ (PR+) | 3720 ± 200.5 | 3774 ± 239.5 | 2481 ± 124.0 |
| 231- (PR-) | 3802 ± 251.9 | 3922 ± 261.0 | 2739 ± 143.0 |
| T47D (PR+) | n/d | n/d | n/d |

| | $T_1$ at 150 μM (ms) | | |
|---|---|---|---|
| | Control | 1 | 2 |
| 231+ (PR+) | 3473 ± 232.0 | 2701 ± 193.9 | 1521 ± 116.2 |
| 231- (PR-) | 3616 ± 263.6 | 2737 ± 195.3 | 1514 ± 114.6 |
| T47D (PR+) | 3310 ± 207.9 | 2849 ± 218.9 | 1742 ± 154.5 |

| | $T_1$ at 500 μM (ms) | | |
|---|---|---|---|
| | Control | 1 | 2 |
| 231+ (PR+) | 3530 ± 4.122 | 3530 ± 30.75 | 1743 ± 14.60 |
| 231- (PR-) | 3528 ± 57.90 | 3482 ± 47.81 | 1813 ± 27.22 |
| T47D (PR+) | 3440 ± 27.79 | n/d | n/d |

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
tgtttgagat cctcttccac cgca                                           24

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
tctccagcat cttcaggcac tgtt                                           24

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
atggggaagg tgaaggtcg                                                 19

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
ggggtcattg atggcaacaa ta                                             22
```

COMPOSITIONS AND METHODS COMPRISING MAGNETIC RESONANCE CONTRAST AGENTS

CROSS-REFERENCE TO RELATED APPLICATIONS

The present application is a continuation-in-part of U.S. application Ser. No. 12/471,731, filed May 26, 2009, which claims priority to U.S. Provisional Application Ser. No. 61/055,629 filed May 23, 2008, both of which are herein incorporated by reference.

STATEMENT REGARDING FEDERALLY SPONSORED RESEARCH OR DEVELOPMENT

This invention was made with government support under grant numbers R21 CA143331, U54 CA090810, R01 EB005866, and R01 HD044464 awarded by the National Institutes of Health. The government has certain rights in the invention.

FIELD OF THE INVENTION

The present invention relates to compositions and methods for imaging with magnetic resonance contrast agents. In particular, the present invention provides targeted contrast agents for selective imaging.

BACKGROUND

An important tool in clinical diagnosis of disease is the use of the magnetic resonance imaging (MRI) contrast agents. In MRI, images are acquired by employing radio frequency pulses to excite nuclear spins of a specimen. The observed signal is from the protons of water molecules in the specimen. MRI can capture three-dimensional images without the need for invasive procedures. By imposing one or more orthogonal magnetic field gradients onto a target, an MR image can be obtained using radio frequency pulses to excite nuclear spins as in NMR. Images are based upon the NMR signal from the protons of water molecules, where the signal intensity in a given volume element is a function of the water concentration and relaxation times ($T_1$ and $T_2$).

MRI has several advantages over other imaging modalities. MRI can image in three dimensions with high spatial and temporal resolution. Unlike while light microscopy and fluorescent microscopy, MRI is not limited by the distance of scattered light onto the cells of interest or dye intensity. It avoids the harmful ionizing radiation of X-ray and CT. Finally, while positron emission tomography (PET) has higher sensitivity, the resolution is much lower than for MRI. MRI can visualize opaque organisms in three dimensions and can follow organisms over time, making it an ideal biological imaging tool.

Sensitivity and intrinsic contrast can be enhanced by using paramagnetic contrast agents, such as the commonly used paramagnetic Gd(III) ion, that decreases the local $T_1$ relaxation of nearby water protons (Caravan et al. Chem Rev 1999, 99, 2293-352., herein incorporated by reference in its entirety). Images derived from changes in $T_1$ regions that are associated with a Gd(III) ion have a higher signal intensity (Aime et al. Curr Pharm Biotechnol 2004, 5, 509-18., herein incorporated by reference in its entirety). The ability of a contrast agent to decrease $T_1$ and therefore increase signal intensity at a given concentration is relaxivity ($mM^{-1} s^{-1}$). High relaxivity agents result in area of increased signal.

Free Gd(III) ions are toxic to biological systems, and a suitable ligand or chelate must bind the lanthanide to form a nontoxic complex. For many years, Gd(III) contrast agents have been used in a chelated form to eliminate toxicity in humans. Several factors influence the stability of chelate complexes including enthalpy and entropy effects (e.g., number, charge and basicity of coordinating groups, ligand field, and conformational effects). Recently, there has been concern associated with the use of Gd(III) agents due to an apparent link to a disabling condition called NSF (Kurtkoti & Hiremagalur. Nephrology 2008, 13, 235-41., Kay Ann Rheum Dis 2008, 67 Suppl 3, iii66-9., herein incorporated by reference in their entirety). Many patients with this condition experience a thickening of the skin that inhibits joint movement. Clinical data on known cases of NSF have revealed that the condition is only present in patients with renal failure (low pH) and only when certain classes of contrast agent are used. Three clinically approved contrast agents have been associated with the onset of NSF: OMNISCAN, MAGNEVIST and OPTIMARK. These are all linear Gd(III) chelates based on the structure of DTPA.

Macrocyclic chelates have higher thermodynamic stability constants and have not been associated with NSF. The reduced thermodynamic stability constants (and the presence of an amide) in linear chelates is thought to be the cause of NSF when Gd(III) is released from the chelate and displaced by other naturally occurring metals. The medical community has studied the risks of using gadolinium in patients with renal failure and has published guidelines to minimize the risk (Shellock & Spinazzi, AJR Am J Roentgenol 2008, 191, 1129-39., herein incorporated by reference in its entirety).

Gd(III) ions are toxic to living tissues, presumably due to binding to calcium channels and therefore, it must be chelated to reduce the bioavailability. These chelates are synthetically versatile and provide the means to attach targeting moieties (Allen & Meade. Met Ions Biol Syst 2004, 42, 1-38., herein incorporated by reference in its entirety).

Mammary epithelial cells express the progesterone receptor (PR) and estrogen receptors (ER) (Ismail et al. Steroids 2003, 68, 779-87., herein incorporated by reference in its entirety). The PR is present in two distinct isoforms both derived from the same gene, PRA and PRB. Each subtype is critical to mammary gland lobuloalveolar development and epithelial differentiation (Lanari & Molinolo Breast Cancer Res 2002, 4, 240-3., herein incorporated by reference in its entirety). The receptor consists of several regions that serve as functional units such as the DNA binding domain (DBD), the ligand binding domain (LBD), and transcriptional activation domains (AFs). The expression of these receptors is a critical parameter typically examined using immunohistochemistry in biopsies of human breast cancers (Jacobsen et al. J Mammary Gland Biol Neoplasia 2003, 8, 257-68., herein incorporated by reference in its entirety).

The presence of both receptors correlates significantly with the survival rate of breast cancer patients (Hopp et al. Clin Cancer Res 2004, 10, 2751-60., herein incorporated by reference in its entirety). The PR is an estrogen-regulated gene that becomes activated and expressed in the presence of estradiol and ER. Therefore, it is not surprising that treatment with tamoxifen (an anti-estrogenic therapy) reduces PR. Decreased PR correlates with tamoxifen resistance, although the mechanism of resistance is still being debated (Arpino et al. J Natl Cancer Inst 2005, 97, 1254-61., herein incorporated by reference in its entirety). Tumors that are ER+/PR− are considered more metastatic and aggressive than PR+ tumors and correlate with a lower survival rate (Cui et al. J Clin Oncol 2005, 23, 7721-35., herein incorporated by reference in its entirety).

An important prognostic marker is the presence of ER+/PR− tumors because these cancers respond much better to aromatase inhibitors than ER+/PR+ tumors that can be effectively treated with tamoxifen (Fuqua et al. J Clin Oncol 2005, 23, 931-2; author reply 932-3., Osborne et al. Breast 2005, 14, 458-65., herein incorporated by reference in their entireties). In addition, expression of PR may also reflect activation of the growth factor pathway Her2/neu. Since monoclonal antibodies directed against the Her2/neu receptor are being developed for breast cancer, knowing the PR status might help determine if a patient will respond to these treatments (Montemurro & Aglietta, Clin Breast Cancer 2005, 6, 77-80., herein incorporated by reference in its entirety). Therefore, non-invasively delineating whether or not a mammary cancer expresses the PR may be crucial to determining the best chemotherapeutic agent for the patient and ultimately improve survival.

The progression of endometrial cancer resembles that of breast cancer in regards to the expression of progesterone receptors. For example, the loss of both PRA and PRB is associated with a poor prognosis and inversely correlated with disease free survival (Boruban et al. Eur J Cancer Prev 2008, 17, 133-8., Uharcek. Obstet Gynaecol Res 2008, 34, 776-83., herein incorporated by reference in their entireties). When each isoforms of the receptor is analyzed separately, the correlation to disease progression is less clear (Arnett-Mansfield et al. Cancer Res 2001, 61, 4576-82., herein incorporated by reference in its entirety); however, the contrast agent would bind to all available progesterone receptors and therefore the overall loss of PR is more critical for imaging purposes. In cell lines, a reduction in the level of PRs is associated with increases in genes that regulate invasion (Miyamoto et al. J Steroid Biochem Mol Biol 2004, 92, 111-8., Saito et al. Cancer Sci 2006, 97, 1308-14., herein incorporated by reference in their entireties). Further, in tissue samples PR is inversely correlated to Ki67, a marker of cellular proliferation. Progesterone is also a therapeutic agent for endometrial cancers with many patients receiving progesterone to slow the growth of their cancer (Ito et al. Endocr J 2007, 54, 667-79., herein incorporated by reference in its entirety).

Recent reports have addressed the use of MR imaging for analyzing breast tumors (Lehman et al. N Engl J Med 2007, 356, 1295-303., Tozaki. Breast Cancer 2008, 15, 205-11., Lee et al. Radiology 2008, 246, 763-71., herein incorporated by reference in their entireties). Although the majority of physicians conclude that traditional mammography is the best for routine screening of the general population, MR imaging is increasingly used in tumor imaging. For patients with familial risk of breast cancer lesions tend to form quickly and have varying appearance using mammography. When a patient has a positive mammography and biopsy, MR imaging is a second line technique to discover other lesions and identify lesions in the contralateral breast. MR can be helpful for guiding biopsies so that the needle is inserted directly into the cancerous area for accurate results.

MR imaging is valuable for determining if a patient is responding to therapy. Response to therapy is one of the critical areas that a targeted steroid-based contrast agent can be used because many drugs for breast cancers down regulate estrogen inducible genes, such as the progesterone receptor. For uterine cancers in particular, progesterone is often given to the patient as part of treatment and in the case of the PR-imaging agent, the technology would possibly be both therapeutic and diagnostic (theranostic).

Progesterone agents have been developed for positron emission topography (PET) imaging with success in targeting breast cancer cells and tissues in rat models (Zhou et al. J Med Chem 2006, 49, 4737-44., Vijaykumar et al. A. J Org Chem 2002, 67, 4904-10., Pomper et al. J Med Chem 1988, 31, 1360-3., herein incorporated by reference in their entireties). Metabolic conversion of reported progestin based PET agents prevented the application of these probes in humans (Dehdashti et al. J Nucl Med 1991, 32, 1532-7., herein incorporated by reference in its entirety).

In vivo imaging agents could provide a tool for basic scientific investigations into the etiology of disease by providing size and molecular profiles of tumors without the need to euthanize the animal. Mouse models of cancer and uterine tumors are an essential component of understanding how to prevent and treat disease. Many models could be improved by applying imaging techniques such that tumors could develop and differentiate without the need to remove the tumor mass directly.

For example, models of ductal carcinoma in situ (DCIS) are available, but understanding when the lesion forms, where, and whether it is steroid responsive is difficult to accomplish without sacrificing the animal and performing a dissection. However, if contrast agents were applied, small lesions could be identified very early, allowing one to determine if they form invasive cancers, and then categorizing the cancer as steroid responsive or unresponsive. Progesterone receptor positive breast and uterine cancer cells can be subcutaneously injected into nude mice and produce solid tumors monitored with magnetic resonance imaging (Zong et al. Magn Reson Med 2005, 53, 835-42., Preda et al. J Magn Reson Imaging 2004, 20, 865-73., herein incorporated by reference in their entireties). The breast cancer cell lines typically used for such tumors include T47D and MCF7 cell lines, both of which express estrogen receptor (ER) and progesterone receptor (PR) (Hoffmann et al. J Natl Cancer Inst 2004, 96, 210-8., herein incorporated by reference in its entirety). For uterine cancers, the Ishikawa cell line lacks receptors and stable clones of the cell line with the PR gene integrated allow the investigator to analyze both receptor positive and negative tumors. Xenografted tumors visibly protrude from the mouse but may be analyzed earlier and with more ease using MR imaging (Bhujwalla et al. Neoplasia 2001, 3, 143-53., herein incorporated by reference in its entirety). These nude mouse tumor models will be used to study the targeting ability of progesterone based contrast agents to image PR+ receptor positive tumors and for quantitative imaging to determine tumor response to drug therapies.

SUMMARY

In some embodiments, the present invention provides a composition comprising: a) a ligand moiety, b) a contrast moiety, and c) a linkage region, wherein the linkage region covalently links the ligand moiety to the contrast moiety. In some embodiments, the ligand moiety comprises a hormone. In particular embodiments, the ligand moiety is produced naturally in a human or animal. In certain embodiments, the ligand moiety is a natural, non-synthetic hormone. In some embodiments, the hormone comprises progesterone. In some embodiments, the contrast moiety comprises a metal-ion chelator. In some embodiments, the metal-ion chelator comprises DO3A. In some embodiments, the metal-ion chelator coordinates a paramagnetic metal ion. In some embodiments, the paramagnetic metal ion includes, but is not limited to Gd(III), Fe(III), Mn(II), Y(III), Cr(III), Eu(III), and Dy(III). In some embodiments, the metal-ion chelator coordinates Gd(III). In some embodiments, the linker region comprises one or more methylene carbons. In some embodiments, the linker region comprises 3 or 6 methylene carbons. In particular embodiments, the linker region is hydrophilic. In some embodiments, the linker region comprises a covalent bond between the contrast moiety and the ligand moiety.

In some embodiments, the present invention provides a composition comprising: a) a hormone, b) metal-ion chelator, and c) a linkage region (e.g., a hydrophilic linkage region), wherein the linkage region covalently links the hormone to the metal-ion chelator. In some embodiments, the hormone comprises progesterone. In some embodiments, the metal-ion chelator coordinates a paramagnetic metal ion. In some embodiments, the paramagnetic metal ion comprises Gd(III).

In some embodiments, the present invention provides a method comprising: a) administering a composition comprising: a) a ligand moiety (e.g. progesterone), b) a metal-ion chelator (e.g. which chelates Gd(III)), and c) a linkage region (e.g., hydrophilic linkage region), wherein the linkage region covalently links the ligand moiety (e.g. progesterone) to the metal-ion chelator to a cell, tissue, or patient, and b) producing a magnetic resonance image of the cell, tissue or patient. In some embodiments, the cell expresses progesterone receptor. In some embodiments, the progesterone binds to a progesterone receptor. In some embodiments, the binding of the progesterone to the progesterone receptor results in localization of the composition. In some embodiments, the cells do not express progesterone receptor.

BRIEF DESCRIPTION OF THE DRAWINGS

The foregoing summary and detailed description is better understood when read in conjunction with the accompanying drawings which are included by way of example and not by way of limitation.

FIG. 21 also shows compound 21 which has a polyethylene glycol linker where n is variable. The compounds may be more hydrophilic with a higher number for n. FIG. 21 also shows compound 22 which employs a peptide linker, where the length and composition of the peptide can be varied to find-tune the water solubility of the compound.

DEFINITIONS

Figure 1:
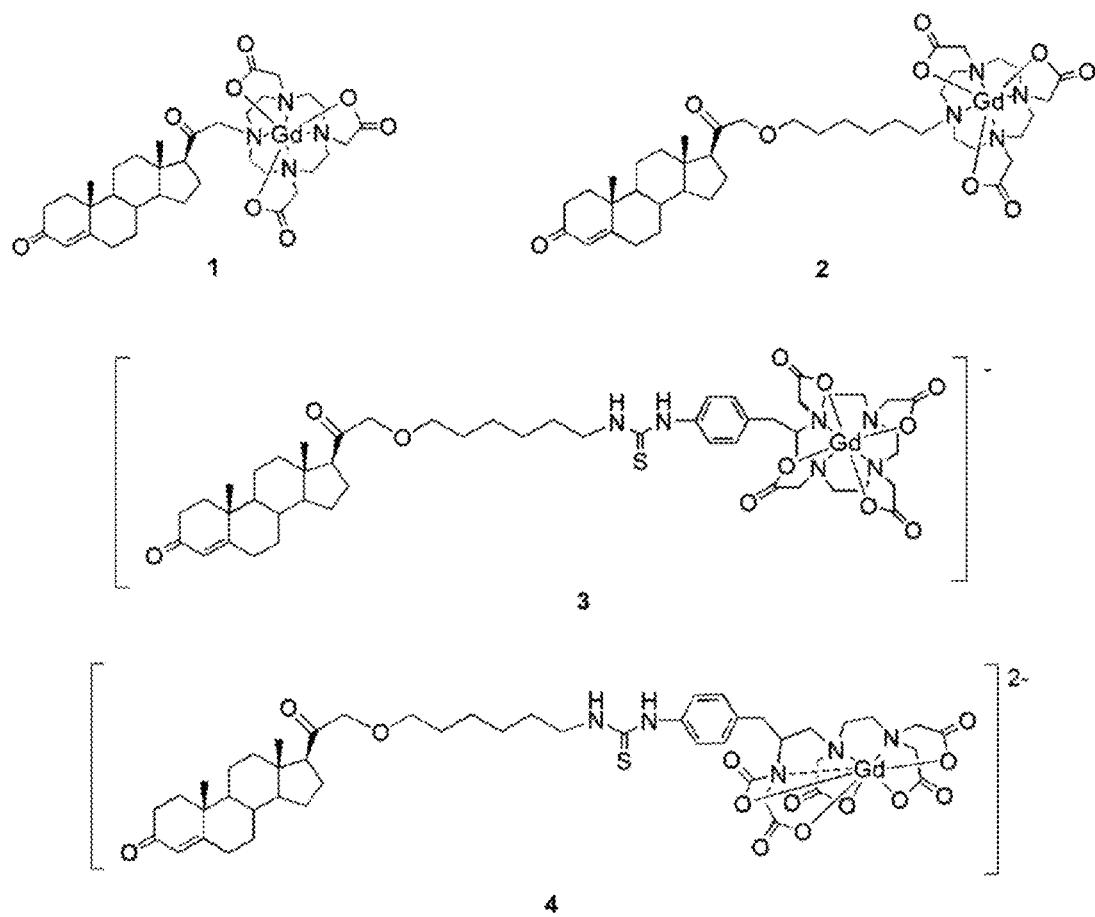
FIG. 1 shows structures of exemplary progesterone-conjugated MRI contrast agents.

As used herein, the term "sample" is used in its broadest sense. In one sense, it is meant to include a specimen or culture obtained from any source, as well as clinical, research, biological and environmental samples. Biological samples may be obtained from animals (including humans) and encompass cells, fluids, solids, tissues, and organs, and whole organisms. Such examples are not however to be construed as limiting the sample types applicable to the present invention.

The term "subject" refers to a cell, tissue, organ, animal, mammal, human, rodent, primate, etc. In some embodiments, the subject is a patient.

The term "bioactive molecule" refers to any chemical entity, whether in the solid, liquid, or gaseous phase which is capable of providing a biological effect when administered to a subject in accordance with the invention. The term "bioactive molecule" includes synthetic compounds, natural products and macromolecular entities such as polypeptides, polynucleotides, or lipids and also small entities such as neurotransmitters, ligands, hormones or elemental compounds. The term also includes such compounds whether in a crude mixture or purified and isolated.

As used herein, the term "relaxation time" refers to the time required for a nucleus which has undergone a transition into a higher energy state to return to the energy state from which it was initially excited. Regarding bulk phenomena, the term "relaxation time" refers to the time required for a sample of nuclei, the Boltzmann distribution of which has been perturbed by the application of energy, to reestablish the Boltzmann distribution. The relaxation times are commonly denoted $T_1$ and $T_2$. $T_1$ is referred to as the longitudinal relaxation time and $T_2$ is referred to as the transverse relaxation time. Other relaxation times of relevance include, but are not limited to $T_1\rho$ (the paramagnetic contribution to the longitudinal relaxation rate) and $T_2^*$ (the transverse relaxtion time including the effect of $B_0$ inhomogeneity). As used herein, the term "relaxation time" refers to the above-described relaxation times either together or in the alternative. Other relevant relaxation times will be apparent to those of skill in the art. An exhaustive treatise on nuclear relaxation is available in Banci, L, et al. NUCLEAR AND ELECTRON RELAXATION, VCH, Weinheim, 1991, which is herein incorporated by reference.

As used herein, the term "diagnostically effective amount" refers to an amount of contrast agent that is sufficient to enable imaging of the contrast agent in cells, tissues, or organisms using imaging equipment.

As used herein, the term "ligand" refers to is a molecule or molecules that are able to bind to and form a complex with a biomolecule.

DETAILED DESCRIPTION

In some embodiments, the present invention provides targeted contrast agents for use in magnetic resonance imaging. In particular, the present invention provides contrast agents for magnetic resonance imaging prepared by conjugating a hormone (e.g. progesterone) to a metal-ion chelator (e.g. Gd(III) chelator) via a linker region (e.g., hydrophilic linker region). The contrast agents are cell permeable and accumulate in target cells based on the affinity for the hormone for its hormone receptor target. The metal-ion chelator provides a $T_1$ contrast agent capable of enhancing MRI signal in the region of contrast agent accumulation Magnetic resonance imaging (MRI) has become an important tool in the clinical diagnosis of cancer. MRI provides noninvasive imaging of opaque specimens due to its high spatial and temporal resolution. The intrinsic magnetic resonance signal can be enhanced through the use of targeted contrast agents. Exogenous contrast agents manipulate relaxation times ($T_1$ and $T_2$) of water protons within a sample and enhance contrast in the image (U.S. Pat. Nos. 7,354,568; 7,029,655; 6,770,261; 6,713,046; 6,713,045; 6,656,450; 5,980,862; 5,707,605; Pub. App. No. 20060088475; Pub. App. No. 20050002866; Pub. App. No. 20040170563; Pub. App. No. 20030198597; Pub. App. No. 20030135108; Pub. App. No. 20030053954; Pub. App. No. 20030021750; Pub. App. No. 20030004236; Pub. App. No. 20020197648; Pub. App. No. 20020098153; and Pub. App. No. 20020049308; herein incorporated by reference in their entireties.

MRI images are acquired by employing radio frequency pulses to excite nuclear spins of a specimen and imposing one or more orthogonal magnetic field gradients (Merbach & Toth (2001). The Chemistry of Contrast Agents in Medical Magnetic Resonance Imaging, New York: John Wiley and Sons., Webb (1993) The Physics of Medical Imaging, Bristol, UK and Philadelphia: Institute of Physics Publishing., herein incorporated by reference in their entireties). The observed signal is that of the protons of water molecules, where signal intensity in a given volume element is a function of the water concentration and relaxation times ($T_1$ and $T_2$) (Allen & Meade (2004) Metal Ions in Biological Systems, Volume 42, New York: Fontis Media., herein incorporated by reference in its entirety). Optical microscopy of opaque specimens is limited by light scattering, whereas MRI can image in three dimensions with high spatial and temporal resolution (Meade et al. (2003) Curr. Opin. Neurobiol. 13, 597-602., Jacobs & Cherry (2001). Curr. Opin. Neurobiol. 11, 621-629., herein incorporated by reference in its entirety). Intrinsic MR contrast can be enhanced by using agents that modulate the spin-lattice relaxation rates of water protons (Caravan et al. (1999) Chem. Rev. 99, 2293-2352., herein incorporated by reference in its entirety). Paramagnetic ions can be used to decrease the local $T_1$ relaxation, and when chelated are nontoxic contrast agents.

A barrier to the development of MRI as a diagnostic tool has been the lack of targeted contrast agents. Previous approaches to develop targeted contrast agents have been limited by the ability of the agent to be linked to an antibody without perturbing the recognition properties or limited by the amount of uptake into cells (Louie et al. (2000) Nat. Biotechnol. 18, 321-325., Li et al. (2002) Inorg. Chem. 41, 4018-4024., Duimstra et al. (2005) J. Am. Chem. Soc. 127, 12847-12855., Allen et al. (2004) Chem. Biol. 11, 301-307., Artemov et al. (2003) Cancer Res. 63, 2723-2727., herein incorporated by reference in their entireties). Therefore, targeted strategies for new generations of chelates and ligands are required to improve cellular permeability and specificity of MRI agents.

The progesterone receptor (PR) is a member of the nuclear receptor superfamily that functions as a ligand activated transcription factor. Mammary epithelial cells express the PR and estrogen receptor (ER) (Ismail et al. (2003) Steroids 68, 779-787., herein incorporated by reference in its entirety). The PR is present in two distinct isoforms both derived from the same gene, PRA and PRB. Each subtype is critical to mammary gland lobuloalveolar development and epithelial differentiation (Lanari & Molinolo (2002) Breast Cancer Res. 4, 240-243., herein incorporated by reference in its entirety). The receptor consists of several regions that serve as functional units such as the DNA binding domain, the ligand binding domain, and transcriptional activation domains. The expression of these receptors is a parameter typically examined using immunohistochemistry in biopsies of human breast cancers (Jacobsen et al. (2003) J. Mammary Gland Biol. Neoplasia 8, 257-268., Bardou et al. (2003) J. Clin. Oncol. 21, 1973-1979., herein incorporated by reference in their entireties). The presence of both receptors correlates with the survival rate of breast cancer patients (Hopp (2004) Clin. Cancer Res. 10, 2751-2760., herein incorporated by reference in its entirety). The PR is an estrogen-regulated gene that becomes activated and expressed in the presence of estradiol and ER. Treatment with tamoxifen reduces PR and correlates with tamoxifen resistance, although the mechanism of resistance is still debated (Arpino et al. (2005) J. Natl. Cancer Inst. 97, 1254-1261., herein incorporated by reference in its entirety). Tumors that are ER+/PR− are considered more aggressive than PR+ tumors and correlate with a lower survival rate (Cui et al. (2005) J. Clin. Oncol. 23, 7721-7735., Muss (1992) Breast Cancer Res. Treat. 21, 15-26., herein incorporated by reference in its entirety). The current clinical methods to determine PR and ER levels require tissue biopsy or radioisotope injection followed by ionizing radiation. Therefore, noninvasively determining whether or not a mammary cancer expresses PR may be crucial to deciding the most effective chemotherapeutic agent for the patient.

As a result of its hydrophilic nature, many MR contrast agents using Gd(III) chelates do not traverse cell membranes and are restricted to the extracellular domains (Allen and Meade (2003). J. Biol. Inorg. Chem. 8, 746-750., Allen et al. (2004) Chem. Biol. 11, 301-307., herein incorporated by reference in their entirety). These chelates are thermodynamically stable ($Kd=10^{21}$~$10^{25}$) and kinetically inert. Embodiments of the present invention provide imaging systems employing steroids to facilitate cell entry of contrast agents. Steroids readily diffuse across the phospholipid bilayer due to their hydrophobic properties and small size (Rao (1981) Mol. Cell. Endocrinol. 21, 97-108., herein incorporated by reference in its entirety). Further, the availability of receptor-specific hormones provides a basis for determining whether the steroid is retained within a specific cell type, allowing the cell, and not the contrast agent, to determine molecular targeting. The steroid progesterone is an endogenous molecule with limited toxic activity and well-established pharmacokinetic profiling (Golub et al. (2006). Birth Defects Res. B Dev. Reprod. Toxicol. 77, 455-470., herein incorporated by reference in its entirety). In addition, steroids are typically retained in the nucleus of cells once bound to their receptor, where they interact with the DNA to drive gene transcription. Contrast agents that bind to large macromolecules such as enzymes or proteins undergo a dramatic increase in the relaxation rate of nearby water protons (Merbach & Toth (2001). The Chemistry of Contrast Agents in Medical Magnetic Resonance Imaging, New York: John Wiley and Sons., Webb (1993) The Physics of Medical Imaging, Bristol, UK and Philadelphia: Institute of Physics Publishing., herein incorporated by reference in their entireties). Binding to a macromolecule increases concentration and retention of the Gd(III) complex at the receptor binding site and affords an increase in rotational correlation time ($\tau_r$) of the agent.

As breast tumors become more aggressive, they typically lose hormone receptors and become less responsive to hormone-based breast cancer therapies. Few methods are available for imaging breast tumors in vivo, and none facilitate the molecular or therapeutic profiling of tumors. Previously, RU-486-modified MR contrast agents were proved to be membrane permeable, and successfully interact with progesterone receptors in cells and provide limited signal enhancement. Experiments were conducted during the development of embodiments of the invention to develop Gd(III)-conjugated steroid contrast agents that accumulate intracellularly, where they interact with nuclear progesterone receptors and thereby increase magnetic resonance. By using a progesterone receptor targeted contrast agent, it was contemplated that one can visualize the morphology of organs and diseased tissue and to determine the biochemical characteristics of cells. Embodiments of the present invention also provide synthetic methodologies for preparing new MRI contrast agents that are targeted to other hormones for imaging of hormone-dependent cancers.

In some embodiments the present invention provides a composition comprising a) a ligand moiety, b) a contrast moiety (e.g. metal-ion chelator and metal ion), and c) a linkage region (e.g., hydrophilic linker region), wherein the linkage region covalently links the ligand to the metal-ion chelator. In some embodiments the ligand moiety is a hormone, progesterone, a progesterone receptor-specific ligand, or anti-progesterone receptor antibody. In some embodiments, the contrast moiety comprises a metal-ion chelator and a metal ion. In some embodiments the metal-ion chelator of the contrast moiety comprises diethylenetriaminepentaacetic acid (DTPA), substituted DTPA, 1,4,7,10-tetraazacyclododecane N,N',N'',N'''-tetraacetic acid (DOTA), substituted DOTA, or other suitable chelators described in U.S. Pat. Nos. 5,155,215, 5,087,440, 5,219,553, 5,188,816, 4,885,363, 5,358,704, 5,262,532, and Meyer et al., Invest. Radiol. 25:S53 (1990), among others. In some embodiments generally suitable linkage regions include, but are not limited to, alkyl and aryl groups, including substituted alkyl and aryl groups and heteroalkyl (particularly oxo groups) and heteroaryl groups, including alkyl amine groups. In some embodiments the present invention provides a method comprising administering such a composition to a cell, tissue or patient. In some embodiments the method further comprises producing a magnetic resonance image of said cell, tissue or patient. In some embodiments the method is used for diagnostic or research purposes (e.g. drug screening applications).

In some embodiments, the present invention provides a contrast moiety which is configured to manipulate the relaxation times of surrounding water proton spins. In some embodiments, contrast moiety is configured to manipulate the longitudinal ($T_1$) and/or transverse ($T_2$) relaxation times. In some embodiments, contrast moiety is configured to manipulate $T_1$ relaxation of surrounding protons. In some embodiments, the materials of the present invention comprise one or more $T_1$ contrast agents. In some embodiments, $T_1$ contrast agents cause a reduction in the $T_1$ relaxation (e.g. increased relaxation time, decreased relaxation rate) resulting in increased signal intensity on $T_1$ weighted images. In some embodiments $T_1$ contrast agents are known as positive contrast agents. In some embodiments, $T_1$ contrast agents are small molecular weight compounds. In some embodiments, the contrast moiety of the present invention comprises a metal-ion chelator. In some embodiments, the contrast moiety of the present invention comprises a metal-ion chelator and a paramagnetic metal ion. In some embodiments, a paramagnetic metal ion is chelated by a metal-ion chelator of the contrast moiety. In some embodiments, $T_1$ contrast agents contain a paramagnetic metal ion as the active element of the paramagnetic contrast agents. Exemplary paramagnetic contrast agents suitable for use in the present compositions include, for example, stable free radicals, such as, for example, stable nitroxides, as well as compounds comprising transition, lanthanide and actinide elements, which may, if desired, be in the form of a salt or may be covalently or non-covalently bound to complexing agents, including lipophilic derivatives thereof, or to polypeptide-containing macromolecules. Preferable transition, lanthanide and actinide elements include, for example, Gd(III), Mn(II), Cu(II), Cr(III), Fe(II), Fe(III), Co(II), Er(II), Ni(II), Eu(III) and Dy(III). The foregoing elements may, if desired, be in the form of a salt, including inorganic and organic salts. In some embodiments, the contrast moiety comprises gadolinium (e.g. Gd(III)).

These elements may also, if desired, be complexed, for example, through covalent or noncovalent association, to one or more complexing agents, including metal-ion chelators, lipophilic derivatives, or to polypeptide-containing macromolecules. Preferable complexing agents for the present invention include, for example, diethylenetriaminepentaacetic acid (DTPA), ethylene-diaminetetraacetic acid (EDTA), 1,4,7,10-tetraazacyclododecane-N,N',N'',N'''-tetraacetic acid (DOTA), 1,4,7,10-tetraazacyclododecane-N,N',N''-triacetic acid (DO3A), 3,6,9-triaza-12-oxa-3,6,9-tricarboxymethylene-10-carboxy-13-phenyl-trideca noic acid (B-19036), hydroxybenzylethylenediamine diacetic acid (HBED), N,N'-bis(pyridoxy)-5-phosphate)ethylene diamine, N,N'-diacetate (DPDP), 1,4,7-triazacyclononane-N,N',N''-triacetic acid (NOTA), 1,4,8,11-tetraazacyclotetradecane-N,N',N'',N'''-tetraacetic acid (TETA), kryptands (macrocyclic complexes), and desferrioxamine. More preferably, the complexing agents are EDTA, DTPA, DOTA, DO3A and kryptands, most preferably DTPA. Preferable lipophilic complexes include alkylated derivatives of the complexing agents EDTA, DOTA, for example, N,N'-bis-(carboxydecylamidomethyl-N-2,3-dihydroxypropyl)-ethylenediamine-N,N'-diacetate (EDTA-DDP); N,N'-bis-(carboxy-octadecylamido-methyl-N-2,3-dihydroxypropyl)-ethylenedia mine-N, N'-diacetate (EDTA-ODP); N,N'-Bis(carboxy-laurylamidomethyl-N-2,3-dihydroxypropyl)ethylenediamine-N,N'-diacetate (EDTA-LDP); and the like, including those described in U.S. Pat. No. 5,312,617, the disclosures of which are hereby incorporated herein by reference, in their entirety. Preferable polypeptide-containing macromolecules include, for example, albumin, collagen, polyarginine, polylysine, polyhistidine, gamma-globulin and beta-globulin, or any polypeptide sequence.

Suitable complexes therefore include, and may be of the type of, but are not limited to: Mn(II)-DTPA, Mn(II)-EDTA, Mn(II)-DOTA, Mn(II)-DO3A, Mn(II)-kryptands, Gd(III)-DTPA, Gd(III)-DOTA, Gd(III)-DO3A, Gd(III)-kryptands, Cr(III)-EDTA, Cu(II)-EDTA, or iron-desferrioxamine.

Additionally, the present invention may utilize a number of different magnetic resonance contrast agents that are well known in the art, and are disclosed in, for example, U.S. Pat. Nos. 5,141,740; 5,078,986; 5,055,288; 5,010,191; 4,826,673; 4,822,594; and 4,770,183, which are incorporated herein by reference. Such magnetic resonance contrast agents include many different paramagnetic contrast agents, for example, gadolinium compounds.

In some embodiments, the present invention provides a linker region (e.g. a region which connects a contrast moiety and a ligand moiety). In some embodiments of the present invention, the ligand moiety and contrast moiety are linked, either directly (e.g. linker region comprises a covalent bond) or linked via a suitable linker (e.g. linker region comprises a linker group). The present invention is not limited to any particular linker group. Indeed, a variety of linker groups are contemplated, suitable linkers could comprise, but are not limited to, alkyl groups, methylene carbon chains, ether, polyether, alkyl amide linker, a peptide linker, a modified peptide linker, a Poly(ethylene glycol) (PEG) linker, a streptavidin-biotin or avidin-biotin linker, polyaminoacids (e.g. polylysine), functionalised PEG, polysaccharides, glycosaminoglycans, dendritic polymers (WO93/06868 and by Tomalia et al. in Angew. Chem. Int. Ed. Engl. 29:138-175 (1990), herein incorporated by reference in their entireties), PEG-chelant polymers (W94/08629, WO94/09056 and WO96/26754, herein incorporated by reference in their entireties), oligonucleotide linker, phospholipid derivatives, alkenyl chains, alkynyl chains, disulfide, or a combination thereof.

A targeted contrast agent of the present invention may comprise a single linker region or multiple linker regions (e.g. 1 linker, 2 linkers, 3 linkers, 4 linkers 5 linkers . . . 10 linkers . . . 20 liners, etc.). In some embodiments the linker comprises a single chain connecting one ligand moiety to one contrast moiety. In some embodiments, there are multiple linkers connecting multiple ligand moieties to a single contrast moiety. In some embodiments, a linker may connect multiple ligand moieties to each other. In some embodiments, a linker may connect multiple contrast moieties to each other. In some embodiments, a linker attaches an additional functional portion to a ligand moiety and/or contrast moiety. In some embodiments, a linker may be branched, connecting more than two ligand moieties and/or contrast moieties. A linker may be flexible, or rigid. A linker may be of any suitable length, and contain any suitable number of atoms and/or subunits.

In some embodiments, the linker of the present invention is cleavable or selectively cleavable. In some embodiments, the linker is cleavable under at least one set of conditions, while not being substantially cleaved (e.g. approximately 50%, 60%, 70%, 80%, 90%, 95%, 99%, or greater remains uncleaved) under another set (or other sets) of conditions. In some embodiments, the linker is susceptible to cleavage under specific conditions relating to pH, temperature, oxidation, reduction, UV exposure, exposure to radical oxygen species, chemical exposure, light exposure (e.g. photo-cleavable), etc.

In some embodiments, the linker region is photocleavable. That is, upon exposure to a certain wavelength of light, the linker region is cleaved, allowing release of the connected contrast agents. This embodiment has particular use in developmental biology fields (cell lineage, neuronal development, etc.), where the ability to follow the fates of particular cells is desirable. A particularly preferred class of photocleavable linkers are the O-nitrobenzylic compounds, which can be synthetically incorporated via an ether, thioether, ester (including phosphate esters), amine or similar linkage to a heteroatom (particularly oxygen, nitrogen or sulfur). Also of use are benzoin-based photocleavable linkers. A wide variety of suitable photocleavable moieties is outlined in the Molecular Probes Catalog, supra.

In some embodiments, the linker is susceptible to enzymatic cleavage (e.g. proteolysis). In some embodiments of the present invention, the ligand moiety and contrast moiety are linked, via a cleavable linker. The present invention is not limited to any particular linker group. In some embodiments, the cleavable linker region contains a peptide portion. In some embodiments, the peptide portion of the cleavable linker region is cleavable. In some embodiments, the peptide portion of the cleavable linker region is enzymatically cleavable. In some embodiments, the peptide portion of the cleavable linker region is configured to be cleaved by proteolysis. In some embodiments the cleavable linked contains a specific proteolytic site.

Figure 21:
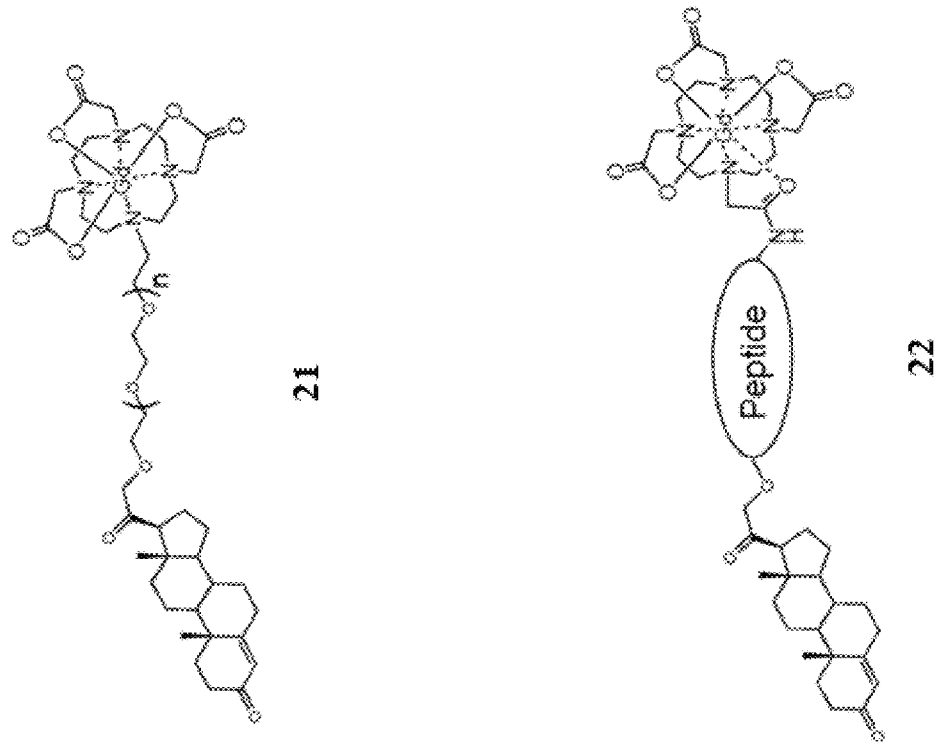
FIG. 21 shows compounds 20A, 20B, and 20C with short aliphatic chain linkers.
Figure 21:
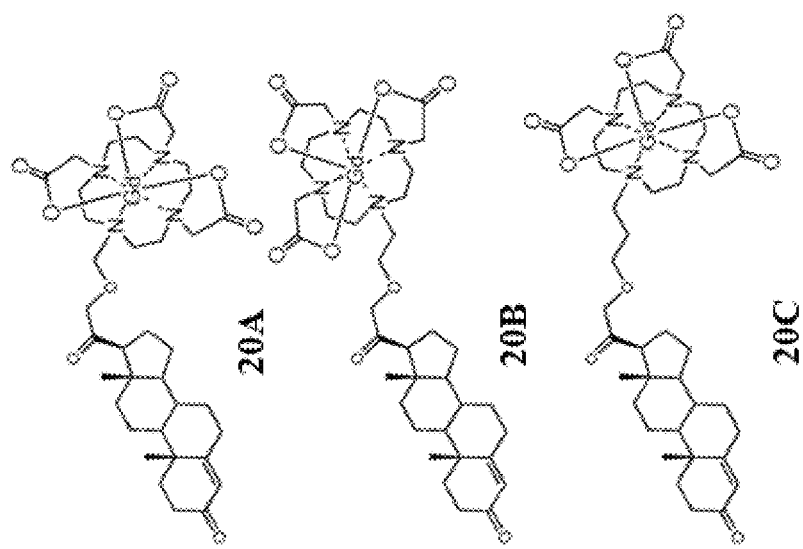

In some embodiments, multiple linker regions are contemplated. A linker region comprising a complex linker constructed from a variety of linker groups is contemplated. Suitable linker groups for construction of a complex linker may comprise, but are not limited to, alkyl groups, methylene carbon chains, ether, polyether, alkyl amide linker, a peptide linker, a modified peptide linker, a Poly(ethylene glycol) (PEG) linker, a streptavidin-biotin or avidin-biotin linker, polyaminoacids (eg. polylysine), functionalised PEG, polysaccharides, glycosaminoglycans, dendritic polymers (WO93/06868 and by Tomalia et al. in Angew. Chem. Int. Ed. Engl. 29:138-175 (1990), herein incorporated by reference in their entireties), PEG-chelant polymers (W94/08629, WO94/09056 and WO96/26754, herein incorporated by reference in their entireties), oligonucleotide linker, phospholipid derivatives, alkenyl chains, alkynyl chains, disulfide, or a combination thereof. In certain embodiments, the linker is a hydrophilic linker. In particular embodiments, the hydrophilic linker comprises a triazole ring. In other embodiments, the hydrophilic linker comprises at least one linker selected from 174 structures in U.S. Pat. Publication 20100323973 (e.g., labeled STR00001-STR00174 in the on-line version), which is herein incorporated by reference. It is noted that STR00001 through STR00174 are each specifically incorporated by reference as if fully set forth herein. In certain embodiments, the linker is short aliphatic chain linker, such as shown in compounds 20A, 20B, and 2C (FIG. 21). In other embodiments, the linker comprises polyethylene glycol as shown in FIG. 21, where n is variable (e.g., n is 1, 2, 3, 4, 5, 6, 7, 8, 9, 10 . . . 15 . . . 20 . . . 30 . . . 40 or more). In certain embodiments, the linker is a peptide as shown in compound 22 (FIG. 21). In particular embodiments, the peptide is a hydrophilic peptide.

In some embodiments, the present invention provides a ligand moiety. In some embodiments, the ligand moiety comprises a small molecule which is configured to bind to or be bound by another molecule (e.g. a binding partner). In some embodiments, the ligand moiety interacts with one or more binding partners through non-covalent binding, covalent binding, hydrogen binding, van der Waals forces, ionic bonds, hydrophobic interactions, electrostatic interaction, and/or combinations thereof. In some embodiments, the ligand moiety may comprise synthetic compounds, natural products, macromolecular entities such as polypeptides, polynucleotides or lipids, and also small entities such as neurotransmitters, substrates, ligands, small drug-like molecules, hormones or elemental compounds. In some embodiments, the ligand moiety comprises a hormone, hormone derivative, or hormone-like molecule. In some embodiments, the ligand moiety comprises a hormone selected from the list of melatonin, serotonin, thyroxine, triiodothyronine, epinephrine, norepinephrine, dopamine, antimullerian hormone, adiponectin, adrenocorticotropic hormone, angiotensinogen, angiotensin, antidiuretic hormone, vasopressin, arginine vasopressin, corticotrophin, atrial-natriuretic peptide, atriopeptin, calcitonin, cholecystokinin, corticotropin-releasing hormone, erythropoietin, follicle-stimulating hormone, gastrin, ghrelin, glucagon, gonadotropin-releasing hormone, growth hormone-releasing hormone, human chorionic gonadotropin, human placental lactogen, growth hormone, inhibin, insulin, insulin-like growth factor, somatomedin, leptin, luteinizing hormone, melanocyte stimulating hormone, orexin, oxytocin, parathyroid hormone, prolactin, relaxin, secretin, somatostatin, thrombopoietin, thyroid-stimulating hormone, thyrotropin, thyrotropin-releasing hormone, cortisol, aldosterone, testosterone, dehydroepiandrosterone, androstenedione, dihydrotestosterone, estradiol, estrone, estriol, progesterone, calcitriol, calcidiol, prostaglandins, leukotrienes, prostacyclin, thromboxane, prolactin releasing hormone, lipotropin, brain natriuretic peptide, neuropeptide Y, histamine, endothelin, pancreatic polypeptide, renin, enkephalin, human variations thereof, non-human variations thereof, combinations thereof, derivatives thereof, etc. In some embodiments, the ligand moiety comprises a steroid hormone selected from the classes of progestagens, estrogens, androgens, mineralocorticoids, and glucocorticoids. In some embodiments the ligand moiety is a hormone, progesterone, a progesterone receptor-specific ligand, or anti-progesterone receptor antibody. In some embodiments, the ligand moiety comprises progesterone.

In some embodiments, the ligand moiety is configured to bind to a biologically relevant molecule, biomolecule, or biological molecular complex. In some embodiments, a ligand moiety of the present invention binds to a protein, peptide, polypeptide, antibody, receptor protein, nucleic acid (e.g. RNA, DNA), carbohydrate, lipid, macromolecule, macromolecular complex, complex thereof, combination thereof, etc. In some embodiments, the ligand moiety is configured to bind to a receptor protein (e.g. hormone receptor (e.g. steroid hormone receptor (e.g. progesterone receptor))). In some embodiments, the ligand moiety is configured to bind to a steroid hormone receptor selected, for example, from the classes of type-I receptors, sex hormone receptors, androgen receptor, estrogen receptor, progesterone receptor, glucocorticoid receptor, mineralocorticoid receptors, type-II receptors, vitamin A receptor, vitamin A receptor, retinoid receptor, thyroid hormone receptor, and the like.

In some embodiments, the ligand moiety (e.g. a small molecule ligand (e.g. a hormone (e.g. progesterone))) is configured to bind to a biomolecule (e.g. macromolecule, protein (e.g. antibody, receptor (e.g. hormone receptor (e.g. progesterone receptor)))). In some embodiments, binding of the ligand moiety (e.g. a small molecule ligand (e.g. a hormone (e.g. progesterone))) to a biomolecule (e.g. macromolecule, protein (e.g. antibody, receptor (e.g. hormone receptor (e.g. progesterone receptor)))) results in targeting the contrast agent complex of the present invention to the specific biomolecule. In some embodiments, the binding of the ligand moiety to a biomolecule of interest results in co-localization of the contrast moiety and the molecule of interest. In some embodiments, binding of the ligand moiety to the biomolecule of interest provides enhanced imaging of the biomolecule of interest as a result of the co-localized contrast moiety. In some embodiments, the ligand moiety targets the contrast moiety to a biomolecule of interest.

In some embodiments, the present invention provides an additional functional portion along with, or in place of, the ligand moiety, linker region, and/or contrast moiety. In some embodiments, an additional functional portion is an optical dye. In some embodiments, the additional functional portion is a chromophore. In some embodiments, an optical dye functional portion allows co-localization of optical imaging with MRI. In some embodiments, the present invention allows co-localization of the contrast moiety with an optical dye functional portion. In some embodiments, the optical dye is selected from the group including, but not limited to acridine dyes, anthraquinone dyes, arylmethan dyes, azo dyes, cyanine dyes, diazonium dyes, nitro dyes, nitroso dyes, phenaanthridine dyes, pthalocyanine dyes, quinine-imine dyes, indamins, indophenols dyes, oxazin dyes, oxazone dyes, thiazin dyes, thiazole dyes, xanthenes dyes, fluorene dyes, pyronin dyes, fluorine dyes, rhodamine dyes, etc. In some embodiments, the optical dye is a fluorophore selected from the list including, but not limited to (E)-stilbene, (Z)-Stilbene, 7-Amino-actinomycin D, Acridine orange, Acridine yellow, Alexa Fluor, Auramine O, Auramine-rhodamine stain, Benzanthrone, 9,10-Bis(phenylethynyl)anthracene, 5,12-Bis(phenylethynyl)naphthacene, CFDA-SE, CFSE, Calcein, Carboxyfluorescein, 1-Chloro-9,10-bis(phenylethynyl)anthracene, 2-Chloro-9,10-bis(phenylethynyl)anthracene, Coumarin, Cyanine, DAPI, Dark quencher, DiOC6, DyLight Fluor, Ethidium bromide, Fluorescein, Fura-2, Fura-2-acetoxymethyl ester, Green fluorescent protein (GFP) and modifications of GFP that have different absorption/emission properties, HiLyte Fluor, Hoechst stain, Indian yellow, Indo-1, Luciferin, Nile red, Perylene, Phycobilin, Phycoerythrin, Phycoerythrobilin, Propidium iodide, Pyranine, Rhodamine, RiboGreen, Rubrene, Ruthenium(II) tris(bathophenanthroline disulfonate), SYBR Green, Sulforhodamine 101, Sulforhodamine B, TSQ, Texas Red, Umbelliferone, and Yellow fluorescent protein.

In some embodiments, an additional functional portion is a biomolecule, such as for example, a ligand, antibody, peptide, polypeptide, protein, nucleic acid, polysaccharide, carbohydrate, lipid, glycoprotein, phosphlipid, sterol, hormone, disaccharide, amino acid, nucleotide, phosphate, monsacharide, etc. In some embodiments, a biomolecule functional portion serves to localize the imaging system in a specific cell type, for example, blastomere, embryonic stem cell, erythrocyte, fibroblast, hepatocyte, myoblast, myotube, neuron, oocyte, osteoblast, osteoclast, T-Cell, zygote, prokaryotic cell, a specific bacteria, plant cells, fungal cells, etc. In some embodiments, a biomolecule functional portion serves to localize the imaging system in a specific cellular region, for example cytoplasm, nucleus, intracellular space, golgi complex, endoplasmic reticulum, mitochondria, chloroplasts, etc. In some embodiments, a biomolecule functional portion serves to localize the imaging system in a specific tissue, for example, epithelial, connective, muscle, neural, etc. In some embodiments, a biomolecule functional portion serves to localize imaging system in specific diseased cells, for example, cancer cells, virally infected cells, etc. In some embodiments, a biomolecule functional portion serves to interact with native biomolecules in a subject, sample, tissue, or cell, such as for example, cell surface markers, antibodies, receptor proteins, nucleic acid, specific classes of proteins, etc.

In some embodiments, an additional functional portion is a biomolecule which serves as a targeting moiety. Herein, the term "targeting moiety" is meant a functional group which serves to target or direct the complex to a particular location, cell type, diseased tissue, or association. In general, the targeting moiety is directed against a target molecule.

In some embodiments, an additional functional portion is a tag allowing the imaging system to be used with additional imaging modalities. In some embodiments, an additional imaging modality provides co-localization of multiple imaging modalities. In some embodiments, an additional imaging modality provides co-localization of an additional imaging modality with the contrast moiety of the imaging system. In some embodiments, an additional functional portion allows the imaging system to be used with, for example, nuclear medicine, molecular imaging, positron emission tomography (PET), single photon emission computed tomography (SPECT), optical imaging, infrared imaging, fluoroscopy, angiography, computed tomography (CT) scanning, etc. In some embodiments, a tag may comprise an additional contrast moiety configured to enhance $T_1$ and/or $T_2$ relaxation.

In some embodiments, the present invention provides contrast agents to be used in generating an image of a cell, tissue, organ, patient, human subject, or non-human subject by administering the contrast agent to the subject (e.g. vascularly, via the gastrointestinal tract, etc.) and generating an image of at least a part of the subject to which the contrast agent has distributed.

In some embodiments, the present invention is used by administering a contrast agent of the present invention to a subject. Known methods for administering therapeutics and diagnostics can be used to administer contrast agents for practicing the present invention. For example, fluids that include pharmaceutically and physiologically acceptable fluids, including water, physiological saline, balanced salt solutions, buffers, aqueous dextrose, glycerol or the like as a vehicle, can be administered by any method used by those skilled in the art. These solutions are typically sterile and generally free of undesirable matter. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration and imaging modality selected. The invention further provides formulations comprising the contrast agent of the invention and a pharmaceutically acceptable excipient, wherein the contrast agent is formed according to any of the above described embodiments, and wherein the formulation is suitable for administration as an imaging enhancing agent and the contrast agent is present in an amount sufficient to enhance a magnetic resonance tomography image. These agents can be administered by any means in any appropriate formulation. Detergents can also be used to stabilize the composition or the increase or decrease the absorption of the composition. Other physiologically acceptable compounds include wetting agents, emulsifying agents, dispersing agents or preservatives that are particularly useful for preventing the growth or action of microorganisms. One skilled in the art appreciates that the choice of an acceptable carrier, including a physiologically acceptable compound depends, for example, on the route of administration and on the particular physio-chemical characteristics of any co-administered agent.

Methods of introduction include, but are not limited to, intradermal, intramuscular, intraperitoneal, intravenous, subcutaneous, intranasal, rectal, vaginal, and oral routes. The compositions may be administered by any convenient route, for example by infusion or bolus injection, by absorption through epithelial or mucocutaneous linings (e.g., oral mucosa, vaginal, rectal and intestinal mucosa, etc.) and may be administered together with other biologically active agents. Administration can be systemic or local. In addition, the contrast agent compositions may be introduced into the central nervous system by any suitable route, including intraventricular and intrathecal injection; intraventricular injection may be facilitated by an intraventricular catheter, for example, attached to a reservoir, such as an Ommaya reservoir. The compositions of the invention can be delivered by any means known in the art systematically (e.g. intravenously), regionally or locally (e.g. intra- or peri-tumoral or intra-cystic injection, e.g. to image bladder cancer) by e.g. intra-arterial, intra-tumoral, intra-venous (iv), parenteral, intra-pneural cavity, topical, oral or local administration, as sub-cutaneous intra-zacheral (e.g. by aerosol) or transmucosal (e.g. voccal, bladder, vaginal, uterine, rectal, nasal, mucosal), intra-tumoral (e.g. transdermal application or local injection). For example, intra-arterial injections can be used to have a "regional effect", e.g. to focus on a specific organ (e.g. brain, liver, spleen, lungs). For example intra-hepatic artery injection or intra-carotid artery injection may be used. If it is decided to deliver the preparation to the brain, it can be injected into a carotid artery or an artery of the carotid system of arteries (e.g. ocipital artery, auricular artery, temporal artery, cerebral artery, maxillary artery etc.). The present invention also provides pharmaceutical compositions which include contrast agents, alone or with a pharmaceutically acceptable carrier.

In some embodiments, amounts of the contrast agents sufficient to provide the desired results will be used, balanced by other considerations such as whether the contrast agent used for a particular application might produce undesirable physiological results. In some embodiments, the precise dose to be employed in the formulation can also depend on the route of administration, and should be decided according to the judgment of the practitioner and each subject's circumstances. In addition, in vitro and in vivo assays may optionally be employed to help identify optimal dosage ranges. Effective doses may be extrapolated from dose-response curves derived from in vitro or in vivo test systems. In some embodiments, the amounts of the contrast agent or agents administered can range from micromolar to molar amounts, but more likely will be used in millimolar-to-micromolar amounts.

The formulations of the invention can be administered in a variety of unit dosage forms, depending upon the particular cell or tissue or cancer to be imaged, the general medical condition of each patient, the method of administration, and the like. Details on dosages are well described on the scientific and patent literature. The exact amount and concentration of contrast agent or pharmaceutical of the invention and the amount of formulation in a given dose, or the "effective dose" can be routinely determined by, e.g. the clinician. The "dosing regimen" will depend upon a variety of factors, e.g. whether the cell or tissue or tumor to be imaged is disseminated or local, the general state of the patient's health, age and the like. Using guidelines describing alternative dosing regimens, e.g. from the use of other imaging contrast agents, the skilled artisan can determine by routine trials optimal effective concentrations of pharmaceutical compositions of the invention.

The present invention provides novel conjugate compositions comprising: a) a ligand moiety, b) a contrast moiety, and c) a linker region. In some embodiments, the present invention provides method of using such conjugates as contrast agents for MRI. In some embodiments, contrast agents of the present invention are administered to a sample, cell, tissue, or patient prior to magnetic resonance imaging of the sample, cell, tissue, subject, or patient. Contrast agents can be used in vivo or in vitro, and can be used in clinical, research, diagnostic, or treatment utilities. In some embodiments, compositions of the present invention may be administered to any cells prior to MRI, for example. In some embodiments, the present invention may find utility in vitro or in vivo applications. In some embodiments, compositions and methods of the present invention may be administered to a cell or tissue which has been isolated and/or purified. In some embodiments, compositions and methods of the present invention may be administered to a cell or tissue which is in the context of a subject or patient. In some embodiments, compositions and methods of the present invention may be administered to a patient or subject.

The present invention provides exemplary MR agents that were synthesized and evaluated to target progesterone receptors (SEE FIG. 1). Compound 2, demonstrated hormone receptor binding, progesterone-responsive gene transcription, and enhanced intracellular relaxivity. Thus, it is demonstrated that steroid receptor specific MR agents can be prepared and retain their ability to interact with their receptor to enhance relaxivity.

The progesterone-MR contrast agent conjugates were designed to optimize receptor interaction. A series of agents was synthesized with variable linkers between the Gd(III) chelate and the hormone backbone. The impact of linker length on receptor interaction was examined using progesterone receptor binding experiments. The agents with the highest affinity were those that had no spacer between the chelate and hormone, such as compound 1. Because it has a hydrophilic Gd(III) chelate instead of having a lipophilic chain on the 21 position, this might indicate that there is a favorable interaction between receptor protein and the chelate, although the present invention is not limited to any particular mechanism of action and an understanding of the mechanism of action is not necessary to practice the present invention. It is contemplated that altering the carbon chain with a hydrophilic PEG linker or poly-amino acid chain may result in higher receptor binding affinity. The progesterone Gd(III) chelates had an approximately 100-fold higher affinity for this receptor than the chelate conjugated to RU-486. Incorporating a linker region between the steroid and the chelate resulted in lower binding affinity for the receptor, perhaps through disruption of dimer formation, although the present invention is not limited to any particular mechanism of action and an understanding of the mechanism of action is not necessary to practice the present invention. The relatively tight binding of the hormone with the receptor demonstrates that the modification of the steroid decreases but does not prohibit interaction with the progesterone receptors.

Conjugation of a Gd(III) chelate to the steroid progesterone allowed for significant and rapid cellular accumulation. All of the compounds traversed the cell membrane in a dose-dependent manner. Conjugate 2 most readily entered the cells, as demonstrated by ICP-MS and X-ray analysis. Compound 1, however, was not as membrane permeable as the compounds containing a six-carbon extended spacer, likely due to its relatively low lipophilicity. The addition of different charges on the chelate adversely affected cell permeability. This may be due to the inability of the charged group to readily pass the hydrophobic membrane, although the present invention is not limited to any particular mechanism of action and an understanding of the mechanism of action is not necessary to practice the present invention. These experiments demonstrate that the steroid conjugation of the Gd(III) chelate allows it to be carried into the cell.

Progesterone-conjugated Gd(III) chelates are cell permeable and interact with the progesterone receptor, providing cell-specific image enhancement. Activation of the specific biological target by the contrast agent was directly demonstrated using the transcriptional activation of the PRE-luciferase construct. Transcriptional activation may enhance specific cellular targeting because the contrast agent would be engaged in a receptor:DNA complex and might be retained within the cell, although the present invention is not limited to any particular mechanism of action and an understanding of the mechanism of action is not necessary to practice the present invention. By directly comparing the amount of gadolinium that leached from progesterone receptor-expressing T47D cells as compared to receptor-negative MDA-MB-231 cells, a relative retention was calculated. Compound 2 was specifically retained in receptor-expressing cells. Compound 1 was not specifically retained, because the initial absorption of the compound is relatively low. Cellular retention is likely different between 1 and 2, due to the enhanced interaction with the receptor after high absorption and the generation of a transcription complex, although the present invention is not limited to any particular mechanism of action and an understanding of the mechanism of action is not necessary to practice the present invention. Evidence of transcriptional regulation is supported by the high level of luciferase activity generated by compound 2 in the PRE transcription assay. The conjugate-induced transcription provides evidence of cellular permeability, receptor-mediated retention, and a lack of toxicity. Cellular transcription suggests that these contrast agents may be useful for obtaining images long after traditional agents that are readily excreted.

Progesterone-based contrast agents provide magnetic resonance signal enhancement inside breast cancer cells. The $T_1$ effects of compound 2 were substantially changed at 150 mM in MDA-MB-231 cells both with and without receptor. Incubating the cells with higher doses of the contrast agent did not produce additional signal enhancement. Compound 1 was expected to produce a greater $\tau_r$ effect because it has the highest binding affinity for the receptor and the slowest rotation of the Gd(III) chelate due to the absence of the six-carbon spacer. However, membrane permeability of 1 was significantly lower even at the highest concentration (500 mM) and failed to enhance MR contrast in vitro. Compound 2 showed high cellular accumulation; however, differences in the amount of accumulation inside cells between PR-positive and PR-negative were insignificant, thereby creating MR images with the same signal intensity. The changes in $T_1$ using relatively low doses of contrast agent indicate that these newly synthesized compounds are viable contrast agents that can be utilized in low doses.

A series of exemplary and illustrative progesterone-modified Gd(III) chelate conjugates were synthesized to generate contrast agents that accumulate intracellularly and interact with a biological target relevant for cancer prognosis. The chelates varied in linker length and charge, and compound 2 has been identified as an efficient agent for progesterone receptor binding and intracellular accumulation. The aliphatic carbon linker between the steroid and the Gd(III) chelate improved cellular permeability while retaining transcriptional activation of the progesterone responsive element without toxicity. Embodiments of the present invention provides that changing the modification site from 3-keto to 21-hydroxyl can enhance the binding affinity approximately 100-fold as compared to a previously reported RU-486-modified contrast agent. The observed relaxivity of the contrast agent in mammary cells was significant.

In some embodiments, the invention provides a kit comprising one or more containers filled with one or more of the contrast agent(s) compositions. In some embodiments, the compositions comprising the contrast agents of the present invention, may be packaged, stored, or administered in combination with other diagnostic or therapeutic treatments.

EXPERIMENTAL

Examples 1 through 8 describe a set of experiments performed during development of embodiments of the present invention (Lee et al. (2007) Chemistry & Biology 14, 824-834., herein incorporated by reference in its entirety). Examples 9 through 14 describe a second set of experiments performed during the development of embodiments of the present invention.

Example 1

Compositions and Methods for Development and Characterization of MR-contrast Agents Octanol-Water Partition Coefficient Measurements. Octanol-water partition coefficients were obtained by dissolving 5-7 mg of each compound (1-4) into mixtures of 500 ml water and 500 ml 1-octanol. The resulting mixture was shaken vigorously for 2 hr on a LAB-LINE lab rotator (model 1304; LAB-LINE, Dubuque, Iowa, USA). The solvent layers were allowed to separate, and 400 ml of each layer was removed. The solvent was removed under reduced pressure, and the mass of material from each layer was measured. The reported values are for the mass of compound in the 1-octanol layer divided by the mass of compound in the water layer.

Relaxivity Measurements. Relaxivity measurements were acquired by taking the slope of a plot of $T_1^{-1}$ versus concentration. The longitudinal water proton relaxation time ($T_1$) at 59.97 MHz was measured using a BRUKER mq60 NMR analyzer (BRUKER Canada, Milton, ON, Canada). A 4 mM stock solution of each compound in deionized water was diluted to give 500 ml each of six concentrations for each run: 0, 0.125, 0.25, 0.5, 1.0, and 2.0 mM. For 3, a 1 mM stock solution in deionized water was diluted to give 250 ml each of six concentrations for each run: 0, 0.001, 0.005, 0.01, 0.05, and 0.1 mM. The $T_1$ of each concentration was determined using an inversion recovery pulse sequence with appropriate recycle delays. The resulting curves were fit to a monoexponential function to obtain $T_1$. Lines fit with $r^2 > 0.998$.

Progesterone Receptor Binding Assay. The progesterone receptor A ligand binding domain (amino acids 675-933) fused to GST (PR-LBD-GST; 80 nM), a fluorescently tagged PR ligand (fluoromone green PL; 4 nM), and either progesterone (1 mM) or compound 1-4 (several concentrations) were incubated in PR screening buffer with 4 mM dithiothreitol (DTT) in a total volume of 100 ml for 1 hr at room temperature according to the manufacturer's protocol (INVITROGEN, Carlsbad, Calif., USA). A Beacon 2000 fluorescence polarization analyzer (INVITROGEN) was used to take fluorescence measurements. The machine was used in static mode, batch blank, no delay, with an average of 1 read per cycle, at 22° C. Buffer and PR-LBD-GST with no fluorescent PL was used as the blank to eliminate background signal from the protein or buffer. A sample with no competitor was used to determine 100% binding capacity of the PR-LBD-GST for the PL ligand.

Progesterone Response Element Transcriptional Activation. T47D breast cancer epithelial cells (American Type Culture Collection, Manassas, Va., USA) were cultured in phenol red-free RPMI (LIFE TECHNOLOGIES, Gaithersburg, Md., USA) supplemented with 10% fetal bovine serum (FBS) (INVITROGEN) and 1% antimycotic/antibiotic (INVITROGEN) and incubated at 37° C., under 5% $CO_2$. Cells were plated 1 day before transfection in 24-well plates and transiently transfected in Opti-MEM (INVITROGEN) with PRE-luciferase. Cells were then treated with serum-free media and vehicle (DMSO), progesterone, and progesterone-modified contrast agents for 24 hr. Cells were lysed in GME buffer (25 mM glycylglycine (pH 7.8), 15 mM MgSO4, 4 mMEGTA, 1 mMDTT, and 1% Triton X-100) and lysates were added to assay buffer (GME buffer, 16.5 mM KPO4, 2.2 mM ATP, and 1.1 mM DTT). Luciferase activity was measured for 30 seconds using an AUTOLUMAT (BERTHOLD TECHNOLOGIES, Oak Ridge, Tenn., USA). A separate protein determination using the BCA kit (PIERCE, Rockford, Ill., USA) was used to normalize protein levels that might differ from treatment with hormone.

Progesterone-Gd(III) Cellular Uptake. Progesterone receptor-positive cells, T47D, and progesterone receptor-negative cells (MDA-MB-231) were used to determine uptake efficiency of progesterone-modified contrast agents into hormone receptor-expressing cells. MDA-MB-231 breast cancer epithelial cells (American Type Culture Collection) were cultured in phenol red-free DMEM/F12 (LIFE TECHNOLOGIES) supplemented with 10 mg/ml insulin, 5% charcoal dextran-stripped FBS (CELLGRO, Herndon, Va., USA), 1% glutamax, and 1% antimycotic/antibiotic (INVITROGEN) and incubated at 37° C., under 5% CO2. Cells were plated into 12-well dishes and the next day they were moved into serum-free media for 24 hr before treatment with compound 1-4. The following doses were incubated with cells for 24 hr: 0, 0.05, 0.5, 5, and 50 mM. 50 mM PR-Gd compounds were incubated with the cells for the following time periods: 0, 1, 2, 4, and 24 hr. Data were analyzed by counting the cells, followed by lysis and ICP-MS. For leaching experiments, contrast agents were incubated with the cells for 4 hr, removed, and rinsed with PBS. At each time point after the initial rinse, cell media were removed, rinsed, and replaced with serum-free media and then collected at 15 min, 1, 2, 4, 6, 24, 48, and 72 hr. The cells were also collected by trypsinization and lysed to compare intracellular content of the cells with that which leached into the media.

Synchrotron Radiation X-Ray Fluorescence Analysis. The receptor-positive and -negative cells were incubated with 1 and 2 for 24 hr prior to analysis. The cells were washed and collected by following the same procedure as described above. Approximately 15 ml of each suspension was applied to Formvar-coated gold grids with a sterile glass Pasteur pipette for 1 min and the excess supernatant was removed. This was followed by addition of approximately 15 ml of room temperature ethanol, removal of the ethanol, and drying at ambient temperature for 15 hr. The cell coverage was approximately 15-30 cells/grid. Electron microscope grids with cells were mounted onto a kinematic specimen mount for both visible light and X-ray fluorescence microscopy. The samples were examined under a light microscope (LEICA DMXRE, Solms, Germany), and the cells to be scanned with SR-XRF were placed on the grid relative to a reference point using a high spatial resolution motorized x/y stage(LUDL BIOPRECISION, Hawthorne, N.Y., USA).

X-Ray Fluorescence Microscopy. Synchrotron scanning X-ray fluorescence microscopy was carried out at the 2-ID-E beamline of the Advanced Photon Source at Argonne National Laboratory (Argonne, Ill., USA). Hard X-rays (10 keV) from an undulator source were monochromatized using a single-bounce Si <111> monochromator. The energy was selected to allow for efficient excitation of the Gd L lines and to enable the detection of the Zn K lines. A Fresnel zone plate (320 mm diameter, focal length f=250 mm, Xradia, Concord, Calif., USA) was used to focus the monochromatic X-ray beam to a spot size of approximately $0.3 \times 0.3$ mm$^2$ on the specimen. The sample was raster scanned through the beam at room temperature under a helium atmosphere. At each scan position, a full fluorescence spectrum was acquired using an energy dispersive germanium detector (ULTRA-LEGE; Canberra, Meriden, Conn., USA). Elemental content was determined by comparison of fitted sample spectra with National Bureau of Standards thin film standards 1832 and 1833 (National Institute of Standards and Technology, Gaithersburg, Md., USA) using MAPS software supplemented with fitting of fluorescence spectra at each pixel.

$T_1$-Weighted Image Acquisition. The receptor-positive (T47D and MDA-MB-231 transfected with PRA) and -negative (MDA-MB-231) cells were incubated with no agent or 50, 150, and 500 mM compound 1 and 2 for 24 hr at 37° C. Cells were loaded into capillary tubes (1 mm diameter) as trypsin suspensions. MR data was collected at ambient temperature in a GENERAL ELECTRIC/BRUKER Omega 400WB 9.4 T magnet (83 mm bore size) fitted with ACCUSTAR shielded gradient coils (BRUKER, Westmont, Ill., USA). Spin lattice relaxation times ($T_1$) were measured using an inversion recovery pulse sequence, and images were acquired using a $T_1$-weighted spin-echo pulse sequence with a repetition time ($T_R$) of 100~2000 ms and an echo time ($T_E$) of 10~10.2 ms.

Example 2

PR-targeted MR Contrast Agents

A series of progesterone conjugates with Gd(III) contrast agents was synthesized and characterized (FIG. 1). Previously, RU-486 was modified with a similar Gd(III) chelate, and it was discovered that the site of attachment was critical to the binding affinity of the complex. The RU-486-modified conjugate had approximately a 100-fold decrease in affinity for the receptor. The labeling strategy was modified for the synthesis of new progesterone agents. The 3-keto group on the hormone is not an ideal modification site because it interacts with a highly conserved region in the receptor protein (Andre & Pusztai (2006) Nat. Clin. Pract. Oncol. 3, 621-632., Madauss et al. (2004) J. Med. Chem. 47, 3381-3387., herein incorporated by reference in their entireties). Therefore, modification or isomerism at this site may compromise the binding affinity of the modified steroid (So et al. (2000) J. Chem. Inf. Comput. Sci. 40, 762-772., Bursi & Groen (2000) Eur. J. Med. Chem. 35, 787-796., Williams & Sigler (1998) Nature 393, 392-396., herein incorporated by reference in their entireties). A number of alternatives to this site are available and position 17 of the D ring was chosen.

Figure 2:
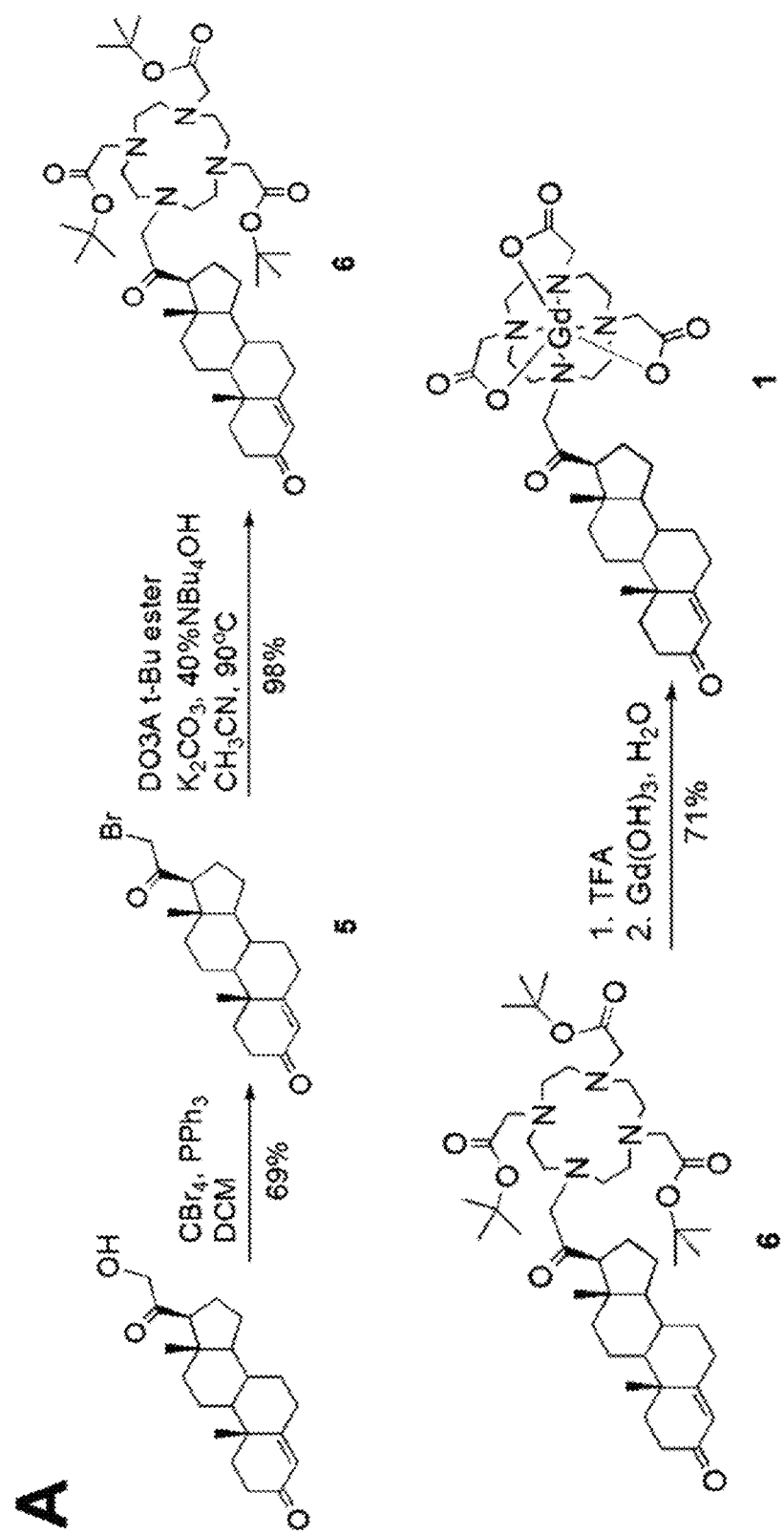
FIG. 2 shows an exemplary synthesis scheme for progesterone modified Gd(III) chelate conjugates: (A) synthesis of neutral conjugates containing no spacer between the contrast moiety and the ligand moiety, (B) synthesis of neutral conjugates containing with a six-carbon linker region between the contrast moiety and the ligand, and (C) synthesis of charged progesterone conjugates.
Figure 2:
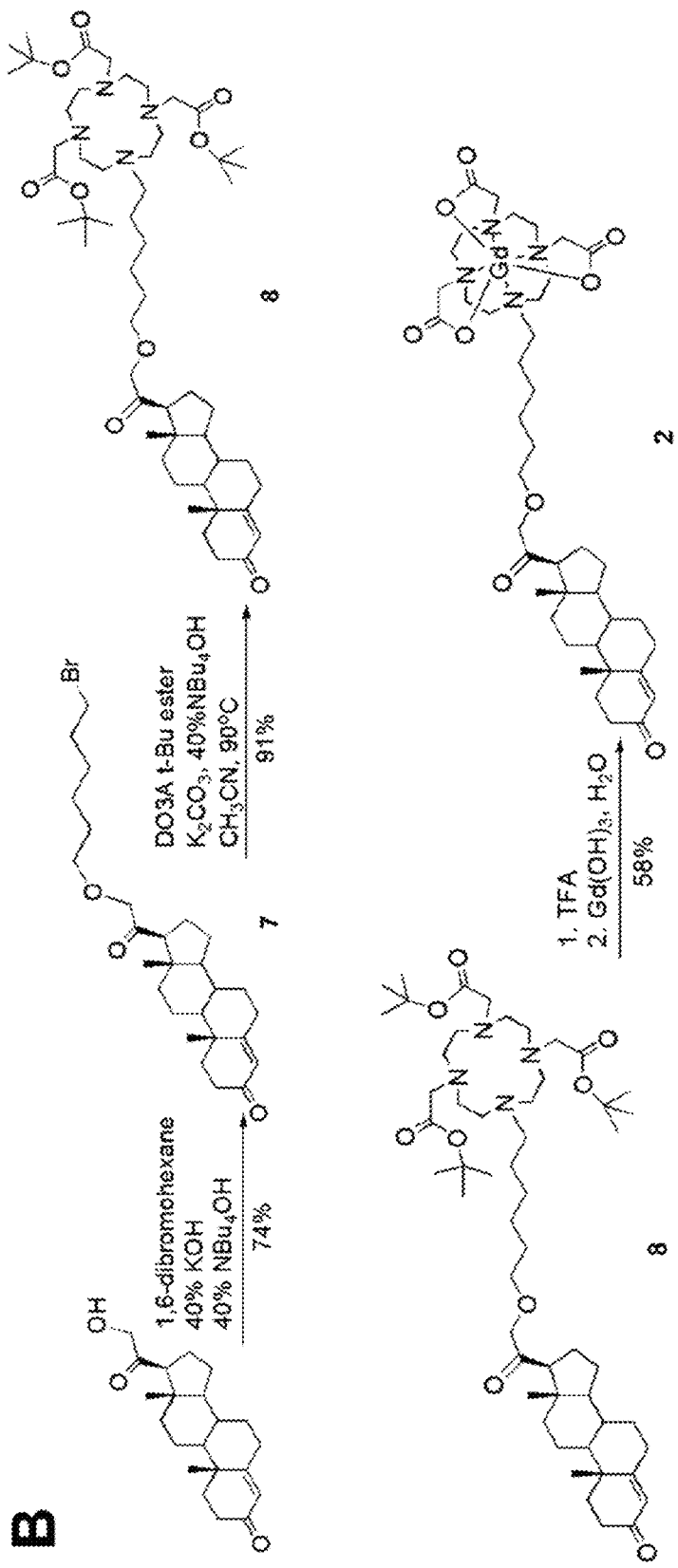
Figure 2:
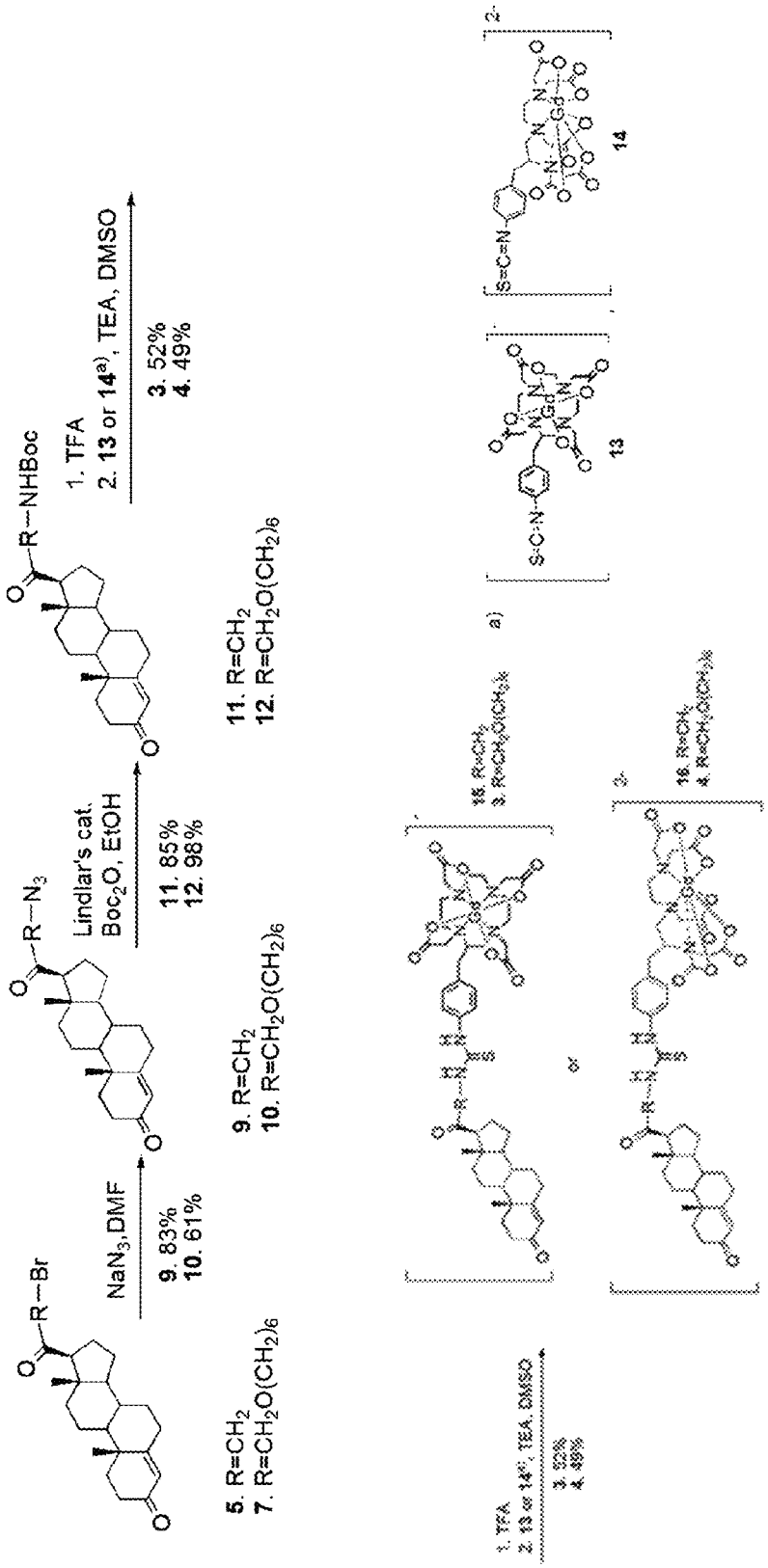

A series of Gd(III) complexes was synthesized to examine the effect of charge on lipophilicity and cell permeability of the conjugate (neutral, −1, and −2). Further, to determine the effect distance between the chelate and steroid may have on receptor binding affinity, spacers with varying lengths (zero, three, and six methylene carbons) were inserted between progesterone and the Gd(III) chelate. The neutral series of conjugates with zero- and six-carbon spacers (1, 2) was synthesized from 21-hydroxyprogesterone, as shown in FIGS. 2A and 2B. The synthesis of 1 began with bromination of the 21-hydroxyl group using carbon tetrabromide and triphenylphosphine. The attachment of 5 with $K_2CO_3$ (NBu$_4$OH as a catalyst) afforded the t-butyl-protected ligand in high yield (93%). After deprotection of the t-butyl group by trifluoroacetic acid, the ligand was heated with Gd(III) chloride at 60° C. to produce compound 1 in 72% yield. The synthesis of 2 started with alkylation of the 21-hydroxyl group by 1,6-dibromohexane. This biphasic alkylation reaction produced bromine-tethered progesterone (7) in 74% yield. A coupling reaction with DO3A followed by insertion of the lanthanide was performed by the same methods described in the synthesis of 2, with 58% yield.

The synthesis of the charged series of conjugates (3, 4) begins with the bromine intermediates (5, 7) from the neutral series (FIG. 2C). In the first step, the bromine group was substituted with an azide. After reducing the azide with Lindlar's catalyst, a coupling reaction of the free amine with an isothiocyanate-Gd(III) chelate was attempted. However, when the pendant amine is neutral or in basic form, the product is unstable, producing a number of uncharacterized byproducts. To circumvent this problem, the azide group was reduced and protected with a Boc group in one pot to give 13 and 14. After deprotection of the Boc group using trifluoroacetic acid, the TFA salt of amines was coupled with the charged Gd(III) chelates (15 and 16) to produce 3 and 4, respectively. Chelates possessing a −1 or −2 charge with no spacer (17 and 18) decomposed during preparative high-performance liquid chromatography purification, and the structure of these molecules was not determined. The charged Gd(III) chelates (15 and 16) were synthesized from commercially available ligands by previously published methods.

Example 3

Relaxivity and Octanol-water Partition Coefficients

The relaxivity and octanol-water partition coefficients of 1-4 are presented in Table 1 and show that charged complexes have higher relaxivities. This tendency is due to aggregation caused by the amphiphilic nature of the compounds. The evidence supporting complex aggregation is the high relaxivity of 3 (19.1 mM$^{-1}$s$^{-1}$) measured in the range of 0.125-2 mM. However, when the solution was diluted approximately 100-fold (concentration range from 0.001 to 0.1 mM), the relaxivity decreased to 5.9 mM$^{-1}$s$^{-1}$.

The octanol-water partition coefficient (P) of each compound was measured to determine lipophilicity. The P value is often expressed in logarithmic form (logP), because the values usually range over many orders of magnitude. The observed logP values of the progesterone conjugates indicate that aggregation is occurring. Compound 3 has approximately the same logP value as 1; however, the relaxivities of these compounds are very different (19.1 and 3.77 mM$^{-1}$s$^{-1}$, respectively). The results indicate that the overall lipophilicity of the two molecules is similar and that the charged species seem to be sufficiently amphiphilic to aggregate in solution. In addition, cellular uptake studies show that unlike commercially available Gd(III) contrast agents, such as PROHANCE, these new steroid conjugates are membrane permeable. Compared to PROHANCE (logP=−2) (Alvarez et al. (1997) J. Pharm. Sci. 86, 1187-1189., herein incorporated by reference in their entireties), all conjugates have greater logP values, demonstrating that lipophilicity of the molecules contributes to membrane permeability.

TABLE 1

Relaxivity Data and Octonol-Water Partition Coefficients (LogP)

| Compound | LogP | Relaxivity (mM$^{-1}$s$^{-1}$)$^a$ |
|---|---|---|
| Progesterone | 3.87$^b$ | — |
| 1 | −0.292 | 3.77/4.76$^c$ |
| 2 | 0.262 | 4.73$^c$ |
| 3 | −0.377 | 19.1/5.9$^d$ |
| 4 | −0.959 | 6.5 |
| Prohance | −2.0 | 3.7* |

$^a$Data were measured at 60 MHz, 37° C.
$^b$data were taken from Alvarez et al.
$^c$Data were measured at 4.7 T, 21° C.
$^d$Data were measured at low concentration from 0.01 to 0.1 nM
*Data were taken from Caravan et al.

Example 4

Binding of Steroid-Gd(III) Conjugates Bind to PR A

Modification of a steroid with a Gd(III) chelate may interfere with the interaction of the steroid with its receptor. Competitive binding experiments were performed using increasing doses of the contrast agents and fluorescently labeled progesterone as the competitor, and the IC50 of each compound for PR was determined. The results are shown in Table 2. Relative binding of each progesterone contrast agent can be compared to progesterone. Compound 1 had the highest relative binding affinity for the receptor of all the compounds and differed only slightly from compound 3. Compound 2 had a relative affinity for the receptor that was about 100-fold lower than progesterone alone, but this was still in the high nanomolar range.

TABLE 2

Receptor Binding Affinity Results

| Compound | IC$_{50}$ (M) |
|---|---|
| Progesterone | $1.6 \times 10^{-9}$ |
| 1 | $9.6 \times 10^{-8}$ |
| 2 | $4.6 \times 10^{-7}$ |
| 3 | $8.6 \times 10^{-7}$ |
| RU-486* | $2.2 \times 10^{-8}$ |
| RU-486-Gd* | $1.9 \times 10^{-6}$ |

*Data were taken from Lee et al.

Example 5

Steroid-based Contrast Agents Demonstrate Accumulated Gd(III) Inside Cells

Figure 3:
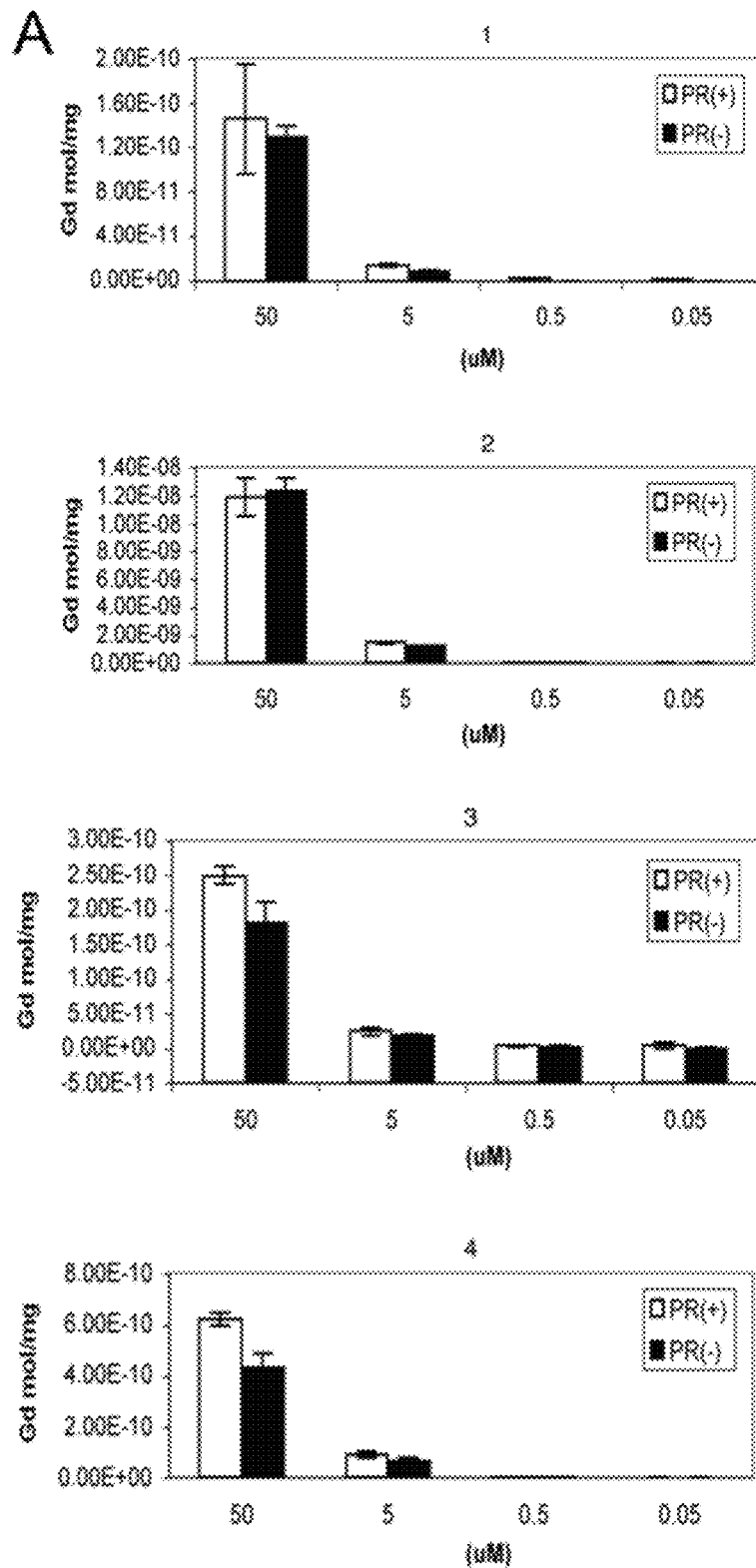
FIG. 3 shows cellular uptake studies of progesterone-modified contrast agents: (A) progesterone-Gd(III) chelates are dose dependently absorbed into mammalian breast cancer cells that either express progesterone or are receptor negative, (B) progesterone-Gd(III) chelates are time dependently absorbed into mammalian breast cancer cells that either express progesterone or are receptor negative, and (C) progesterone-Gd(III) chelates are selectively retained in progesterone receptor-expressing cells at specific time points after leaching into culture medium.
Figure 3B:
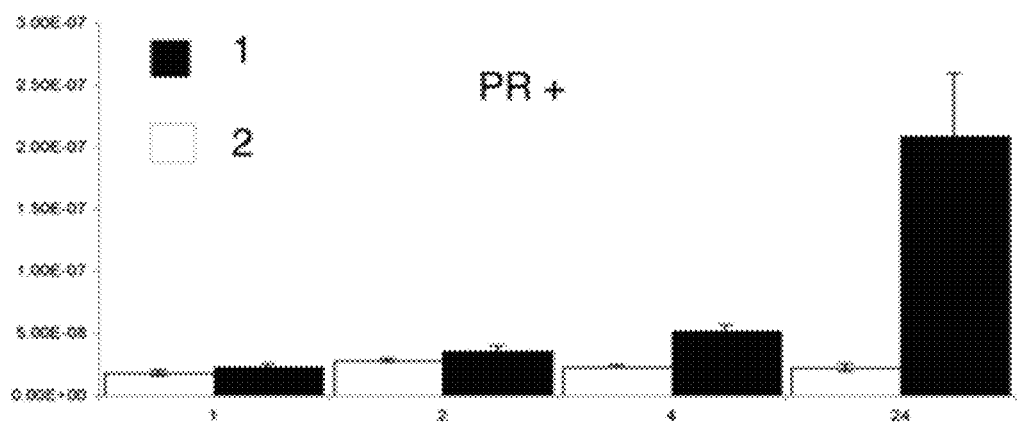
Figure 3B:
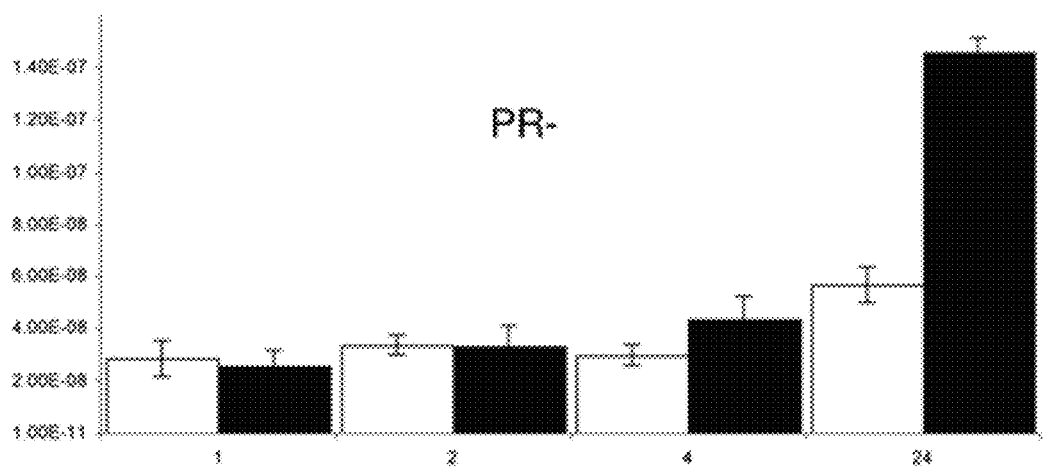

Cellular uptake experiments were performed by incubating the contrast agents with progesterone receptor positive (T47D) and progesterone receptor-negative (MDA-MB-231) mammary epithelial cells. In dose-response experiments cells were incubated with 50, 5, 0.5, or 0.05 mM agents for 24 hr with T47D and MDA-MB-231 cells. The contrast agents were absorbed in a dose-dependent manner and demonstrated maximal accumulation at 50 mM (FIG. 3A). Cells were incubated with only 1 or 2 at different time points including 1, 2, 4, and 24 hr. After incubation, the cells were lysed and subjected to inductively coupled plasma mass spectrometry (ICP-MS) analysis to quantify the number of Gd(III) ions present in each cell based on milligrams of protein (FIG. 3B). Compound 2 showed the highest uptake into the PR-expressing T47D cell line, and in cells lacking PR, the MDA-MB-231 cell line. Compounds 3 and 4 had much lower uptake, demonstrating that the negative charge of the contrast agent reduces cellular permeability. Similarly, compound 2 was significantly more absorbed than 1, demonstrating the importance of the hydrophobic carbon linker. To determine the cellular distribution of 1 and 2, synchrotron radiation X-ray fluorescence (SRXRF) analysis was performed. SR-XRF spectroscopy uses high-energy X-rays to produce a map of each element's concentration with submicrometer resolution, whereas conventional XRF analysis provides the elemental composition of materials. An advantage of SR-XRF over standard fluorescence microscopy is that images are obtained without altering the agent by attachment of an organic fluorophore. Compounds 1 and 2 (50 mM) were incubated with progesterone receptor-positive cells (T47D) and -negative cells (MDA-MB-231) for 24 hr prior to scanning The samples were raster scanned with 2.0 µm×2.0 µm step size. The images show accumulation of each compound within cells and confirmed cellular uptake of 2.

Example 6

Figure 3C:
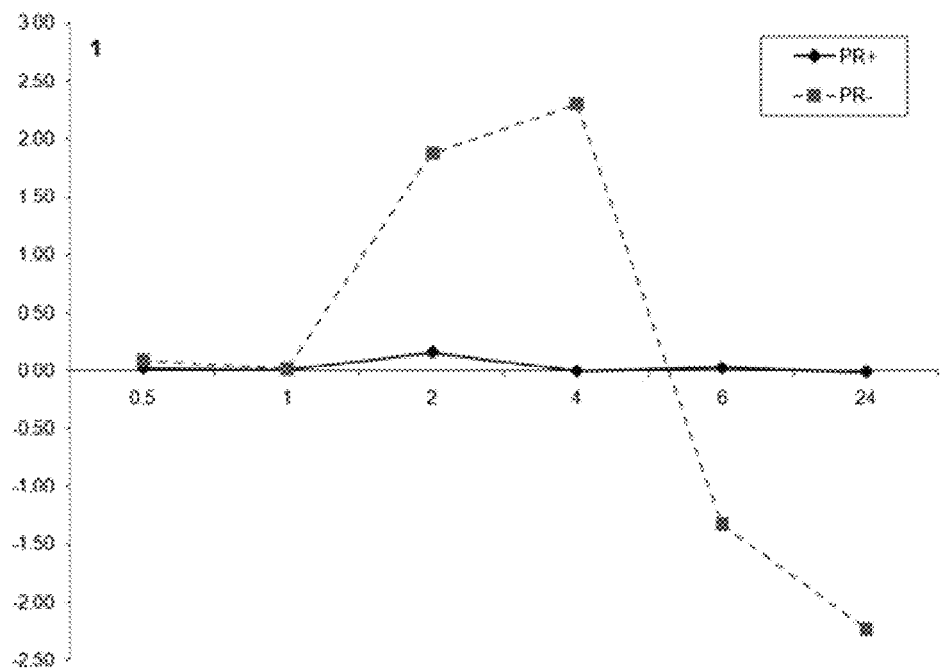
Figure 3C:
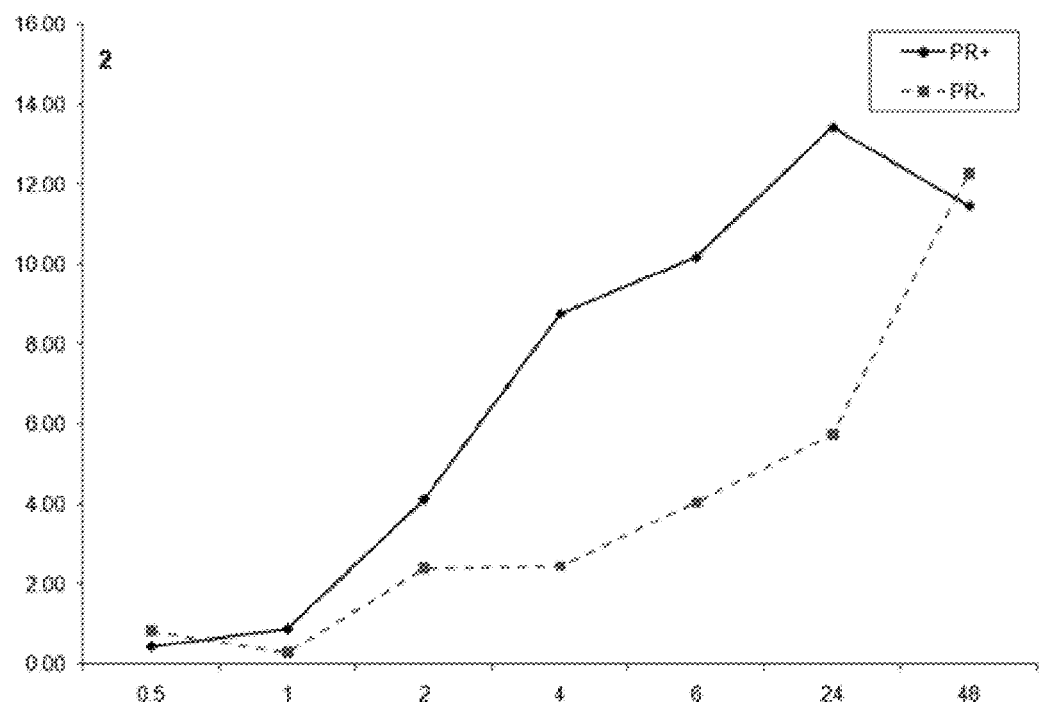
Figure 3C:
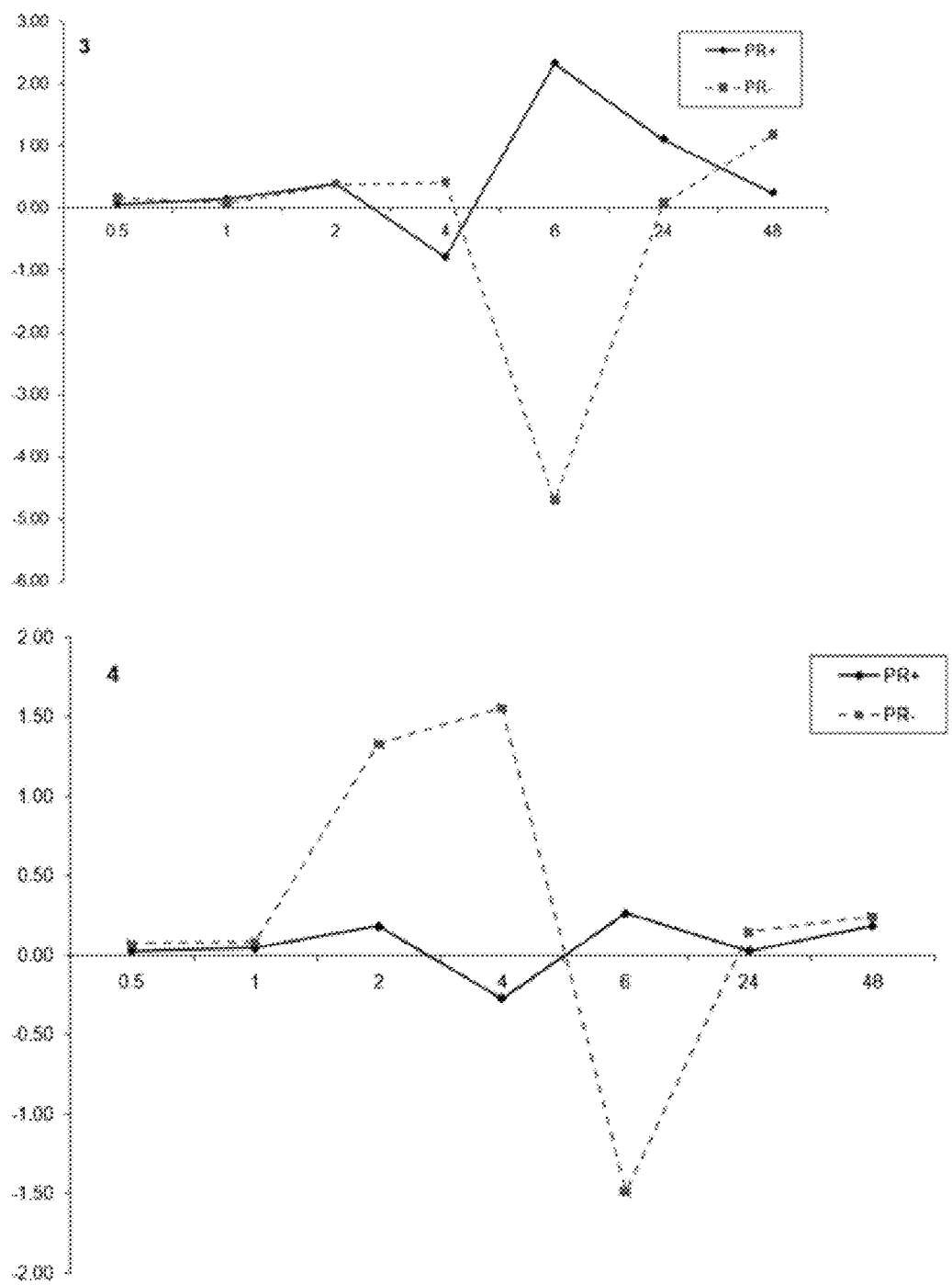

Steroid-based Contrast Agents Efflux More Slowly from Receptor-expressing Cancer Cells One aspect of molecular specificity that a steroid-based contrast agent may provide is retention in cells expressing the progesterone receptor. Because progesterone interacts with its receptor and is active in the nucleus as a transcription factor long after initial absorption, experiments were designed to determine whether this would result in a slower leaching of the contrast agents from progesterone receptor-expressing T47D cells as compared to the progesterone receptor-negative MDA-MB-231 cells. Cells were incubated with 50 mM contrast agents for an initial 24 hr absorption period. The media containing the contrast agents were then removed, followed by three PBS washes, and the cells were then allowed to leach the intracellular portion of the contrast agent into serum-free media for 1, 2, 4, 6, 24, or 48 hr. The amount of the contrast agents was then determined by quantifying the amount of compound inside the cell using ICP-MS and then divided by the amount of gadolinium in the leached media minus the background (FIG. 3C). Although 1 did not appear to leach from the MDA-MB-231 cells more quickly, compound 2 showed much higher retention in the T47D cell line as compared to MDA-MB-231. Therefore, one way that these compounds specifically mark progesterone receptor-positive cells is by residing in the cell longer, due to interaction with PR.

Example 7

Steroid Conjugates Function to Transcriptionally Upregulate Pre-luciferase

Figure 4:
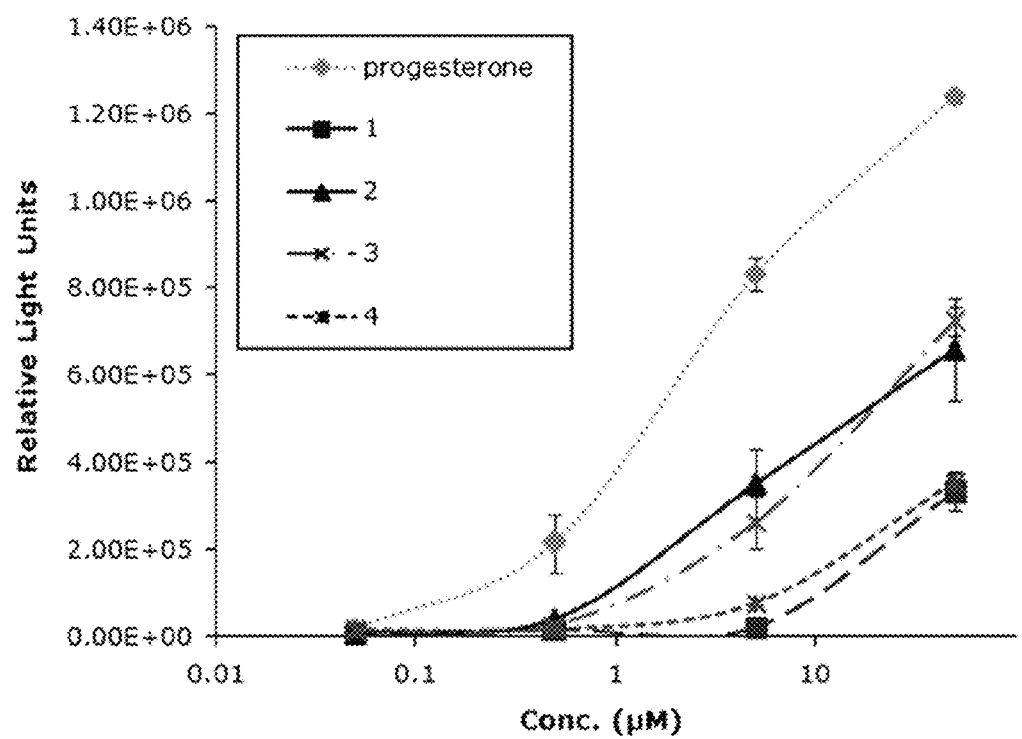
FIG. 4 shows a graph demonstrating that progesterone-Gd (III) chelates function biologically to initiate gene transcription of a progesterone responsive element.

Progesterone receptors bind to a region of DNA referred to as the progesterone response element (PRE). This DNA element (repeated three times) was ligated to DNA encoding the luciferase gene and used to (1) monitor the cell permeability of the compounds, (2) verify the ability to interact with the progesterone receptor dimer, and (3) evaluate function in a transcription complex (FIG. 4). For the progesterone derivatives, induction of luciferase demonstrated that the compound was functional. Each compound showed the ability to alter transcription of the PRE, indicating that it entered the cell and bound to the full-length progesterone receptor. Agent 2 proved the most effective transcriptional agent and differed marginally from compound 3 in its ability to bind to the receptor. This demonstrates that a neutral charge on the agent is beneficial for activity and permeability. A hydrophobic linker between the progesterone molecule and the Gd(III) chelate appeared to improve cell permeability and may increase transcription, because the compounds are inside the cell interacting with the progesterone receptor for a longer period of time. These data confirm that although compound 2 does not bind as readily to the PR as compound 1, the improved cell permeability makes the agent enter the cells more rapidly, at lower doses, and provides higher transcriptional activity.

Example 8

Steroid-Based Contrast Agents Enhance T1 Relaxivity In Vitro

Figure 5:
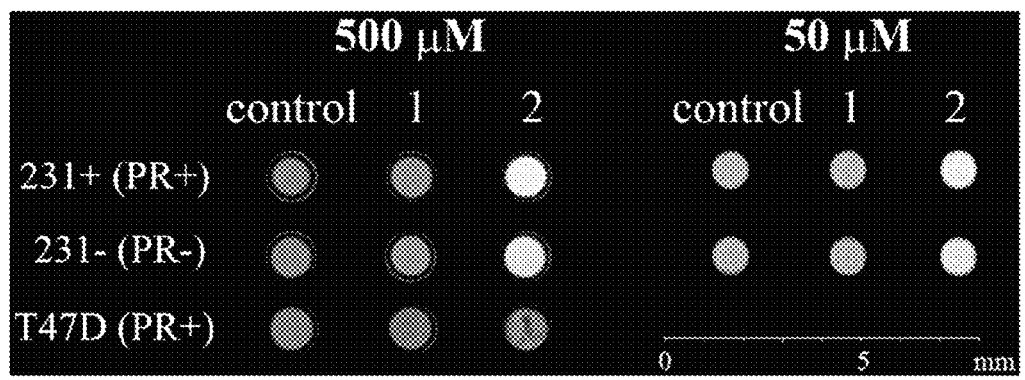
FIG. 5 shows in vitro MRI results: (A) $T_1$-weighted averages of breast cancer cells incubated with compounds 1 and 2 for 24 hours, and (B) $T_1$ data of cells incubated with 50, 150, and 500 µM of compound 1 or 2.

To determine the effect of 1 and 2 on $T_1$ after receptor binding, $T_1$-weighted images and measured spin-lattice relaxation times of incubated cells were obtained (FIG. 5A). Compound 1 was chosen because of its high binding affinity and compound 2 because of efficient cellular uptake. Progesterone receptor-positive cells (T47D, MDA-MB-231 transfected with PRA) and -negative cells (MDA-MB-231) were incubated with 50, 150, and 500 mM 1 and 2 for 24 hr prior to scanning $T_1$-weighted images and relaxation times show that compound 2 enhanced MR contrast significantly more than compound 1 in any given cell type. All cells that were treated with compound 2 appeared much brighter than the cells that were treated with compound 1 or control media. For example, cells exposed to 150 mM 2 reduced $T_1$ more than 60% compared to controls. There are no significant changes in $T_1$ at 500 mM 2, demonstrating that the cells were saturated with compound 2 at 150 mM and no further uptake occurred.

Example 9

Steroid Hormones Modified with Gd(III) Chelates

Figure 6:
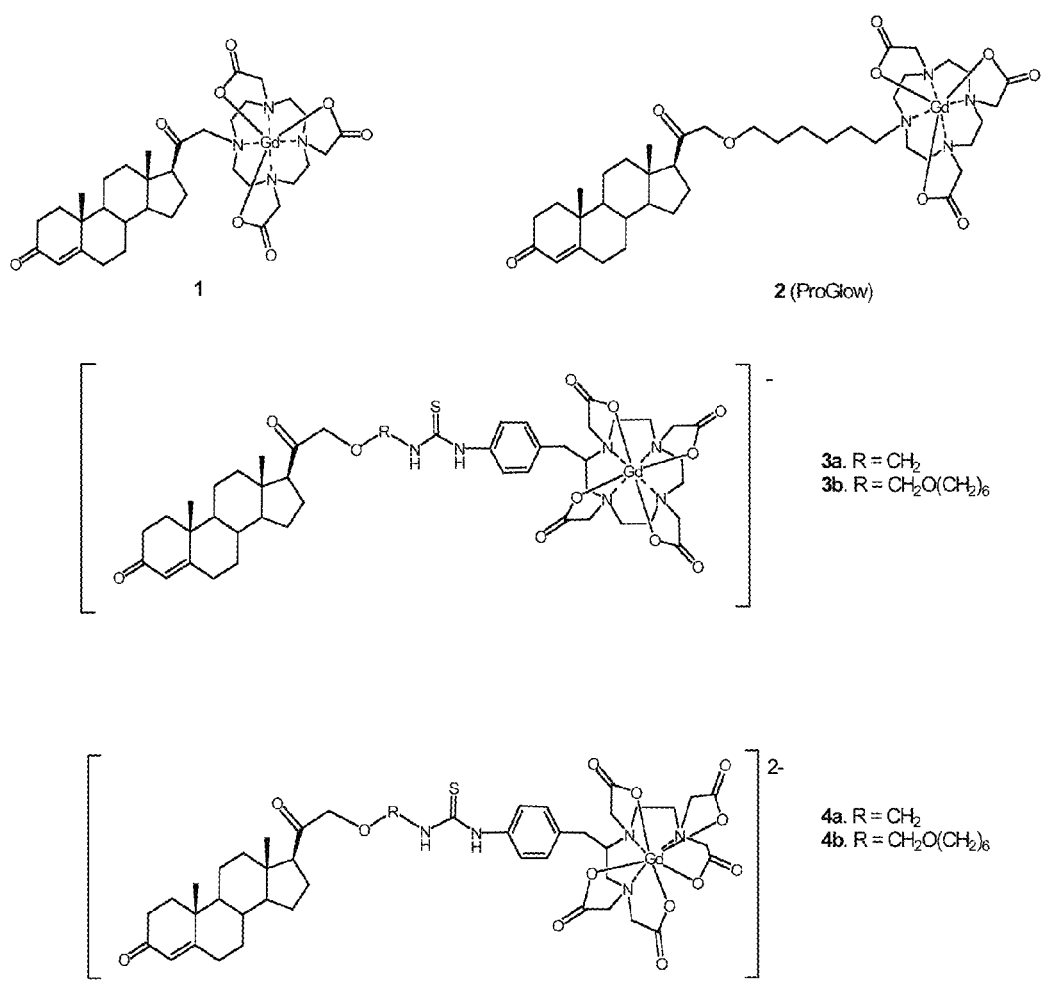
FIG. 6 shows chemical structures and names of steroid contrast agents.

During experiments performed during development of embodiments of the present invention, first and second generation steroid-modified contrast agents, mifepristone-Gd(III) (RU486-Gd(III)) and progesterone-Gd(III) were developed. Progesterone can be monitored biologically, and has a higher binding affinity for the receptor and better activation of target genes than RU486-Gd(III). The progesterone contrast agents were synthesized by modifying 21-hydroxyprogesterone (SEE FIG. 6). The first progesterone contrast agent (SEE FIG. 6 (1)) synthesized has no linker between the Gd(III) chelate and progesterone. A second agent possesses a 6-carbon linker between the Gd(III) chelate and the progesterone molecule (SEE FIG. 6 (2)). Agents were prepared with a Gd(III) chelate that contains either a −1 or −2 charge (SEE FIG. 6 (3a, 3b, 4a, 4b)). This series of demonstrated higher water solubility while still traversing the phospholipid bilayer. Compound 2 demonstrated the best overall activity and image enhancement.

Example 10

Steroid Conjugates Bind to the Ligand Binding Domain of Progesterone Receptor A Competitive binding experiments were carried out using fluorescently labeled progesterone as a competitor for each synthesized compound at increasing doses. Experiments were performed to determine the inhibitory concentration at 50% ($IC_{50}$) of each synthesized agent for the ligand-binding domain of the progesterone receptor (PR). The results for the compounds are shown in Table 3.

TABLE 3

Steroid contrast agents bind to the progesterone receptor.

| Compound | $IC_{50}$ (M) |
|---|---|
| Progesterone | $1.6 \times 10^{-9}$ |
| RU486 | $2.2 \times 10^{-8}$ |
| RU486-Gd(III) | $1.9 \times 10^{-6}$ |
| 1 | $9.6 \times 10^{-8}$ |
| 2 | $4.6 \times 10^{-7}$ |
| 3a | $7.4 \times 10^{-8}$ |
| 3b | $8.6 \times 10^{-7}$ |

Values represent the inhibitory concentration at 50% ($IC_{50}$) for PR-Gd(III) contrast agents bound to the purified ligand-binding domain of progesterone receptor A.

Relative binding of each progesterone contrast agent was compared to progesterone, whereas RU486-Gd(III) was compared to RU486. The contrast agent with the highest affinity of those tested is compound 1 followed by compound 3a. All of the progesterone agents demonstrated at least a 10 fold higher binding affinity as compared to the RU486 agents.

Example 11

Cell Permeability of Steroid-based Contrast Agents

Experiments were conducted during developments of embodiments of the present invention to develop cell permeable MRI contrast agents and to test the cell permeability of such agents. To test the cell-permeability of the synthesized compounds, cellular uptake experiments were performed by incubating the contrast agents with progesterone receptor positive (T47D) mammary epithelial cells. Dose response experiments were performed to identify the concentration of contrast agents needed for maximal cellular accumulation. The contrast agents were absorbed in a dose dependent manner and demonstrated maximal accumulation at 50 µM (not shown).

Cells were incubated with compound 1 compound 2 at various time points including 1, 2, 4, and 24 hours. After incubation, the cells were lysed, and subjected to ICP-MS analysis to quantify the amount of Gd(III) present in each cell based on mg of protein. Significantly more Compound 2 was absorbed into cells than Compound 1. This finding may demonstrate the importance of the hydrophobic carbon linker, although the present invention is not limited to any particular mechanism of action and an understanding of the mechanism of action is not necessary to practice the present invention.

Example 12

Figure 7:
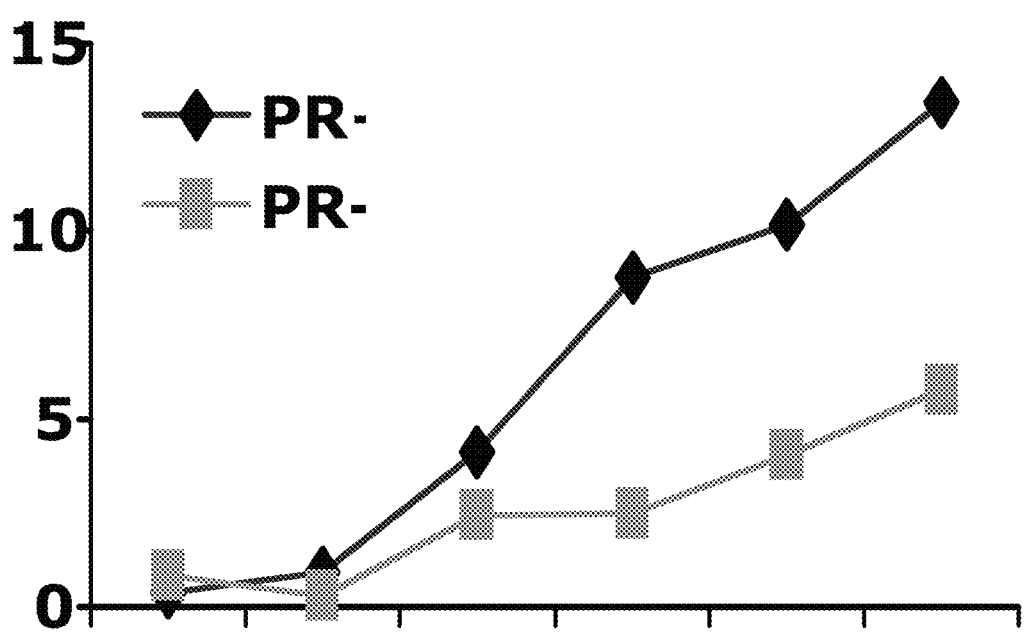
FIG. 7 shows a graph demonstrating progesterone-Gd(III) chelates are selectively retained in progesterone receptor expressing cells. Gd(III) was quantified using ICP-MS.

Steroid-based Contrast Agents are Specifically Retained in Progesterone Receptor Cells Progesterone mediated cell retention may provide specificity for imaging progesterone receptor positive mammary cancers. Experiments were performed during development of embodiments of the present invention to determine if progesterone binding resulted in slower leaching of the contrast agents from progesterone receptor expressing T47D cells as compared to the progesterone receptor negative MDA-MB-231 cells. Cells were incubated with 50 µM of compound 1 and compound 2 for an initial 24-hour absorption period. The media containing the contrast agents was then removed, followed by three PBS washes and then the cells were allowed to leach the intracellular portion of the contrast agent into serum free media for either 0.5, 1, 2, 4, 6, or 24 hours. The percent retained of the contrast agents was then determined by quantifying the amount of compound inside the cell using ICP-MS divided by the amount of Gd(III) in the leached media minus the background (SEE FIG. 7). Although compound 1 did not appear to leach from the MDA-MB-231 cells more quickly, compound 2 showed much higher retention in the T47D cell line as compared to MDA-MB-231. Compound 2 and other compound of the present invention specifically mark progesterone receptor positive cancers by residing in the receptor positive cells due to interaction with PR

Example 13

Steroid Conjugates Function to Transcriptionally Upregulate Pre-luciferase

Figure 8:
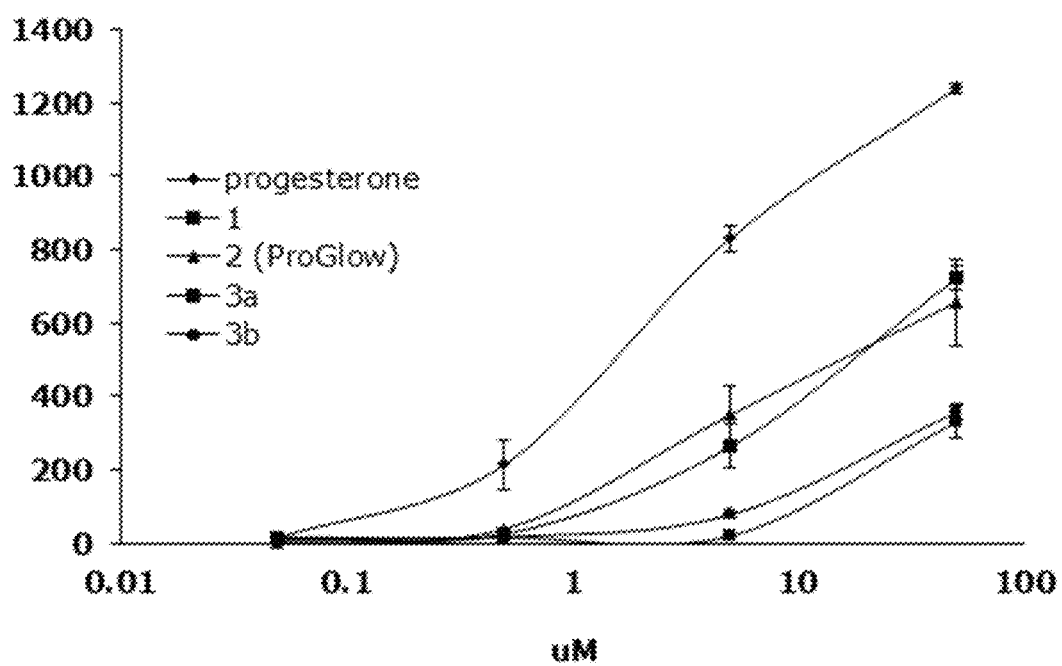
FIG. 8 shows a graph demonstrating transcriptional upregulation of progesterone responsive promoter in response to PR-Gd(III) contrast agents.

Progesterone receptors, when bound with progesterone, bind to a region of the DNA commonly referred to as the progesterone response element (PRE). A triple repeat of the PRE was ligated to DNA encoding the luciferase gene and was used to monitor cell permeability of the compounds as well as the ability of compounds to interact with a progesterone receptor and function as a transcriptional complex (SEE FIG. 8). The induction of luciferase indicated that the compound was functional. Each agent showed the ability to increase transcription of the PRE indicating that it entered the cell and bound to the full-length receptor. Compound 2 proved the most effective transcriptional agent and only differed marginally from compound 3a in its ability to bind to the receptor, thus indicating that a neutral charge on the contrast agent is most beneficial for activity and permeability. The transcription of PRE in response to these novel contrast agents demonstrates: 1) the agents cross the cell membrane, 2) the agents bind to the full-length endogenous receptor and initiate dimerization, and 3) the agents function as initiators of gene transcription which will likely provide for longer cell retention and demonstrates that the biological target has been activated.

Example 14

Figure 9:
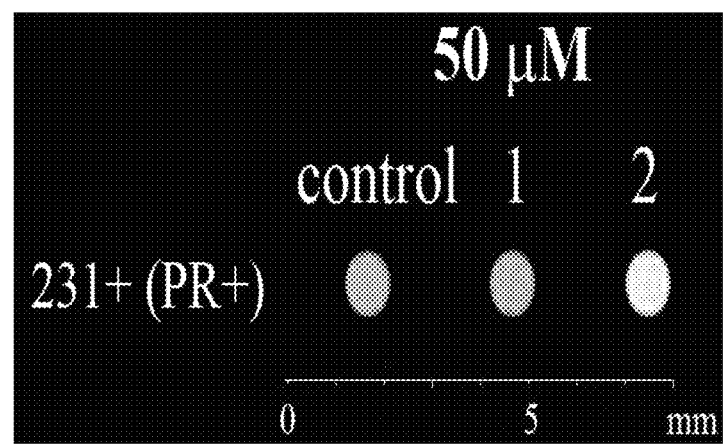
FIG. 9 shows $T_1$-weighted images and measured spin-lattice relaxation times of cells incubated with compounds 1 and 2: Top Panel, MRI images acquired from PR-Gd(III) contrast agents inside of human breast cancer cells expressing the progesterone receptor; Bottom Panel, $T_1$ weighted values of mammary cells incubated with PR-Gd(III) contrast agents. The values are also depicted as the percent decrease in relaxivity as compare to the solvent control.

Steroid-based Contrast Agents Enhance Relaxivity in Mammary Cells $T_1$-weighted images and measured spin-lattice relaxation times were obtained of cells incubated with compound 1 and compound 2 (SEE FIG. 9). Compound has demonstrated a high binding affinity and compound 2 has demonstrated efficient cellular uptake. Progesterone receptor positive cells (MDA-MB-231 transfected with PR-A) were incubated with 50, 150, and 500 uM of compound 1 and compound 2 for 24 hours prior to scan. The images are of cell pellets that were grown in monolayer culture, treated with contrast agent, washed with PBS, and then compacted into a capillary tube for MRI. The $T_1$ values were weighted. All MR data was collected at ambient temperature in a General Electric/Bruker Omega 400WB 9.4 T magnet (83 mm bore size) fitted with Accustar shielded gradient coils. Spin lattice relaxation times ($T_1$) were measured using an inversion recovery pulse sequence. Images were acquired using a $T_1$ weighted spin-echo pulse sequence with repetition time ($T_R$) of 100~600 ms and an echo time ($T_E$) of 10~10.2 ms. $T_1$-weighted images and relaxation times show that compound 2 enhanced MR contrast significantly more than compound 1. All cells that were treated with compound 2 appeared brighter than the cells that were treated with compound 1 or control media. The synthesized progesterone compounds significantly increase relaxivity of cells in vitro.

Example 15

Figure 10:
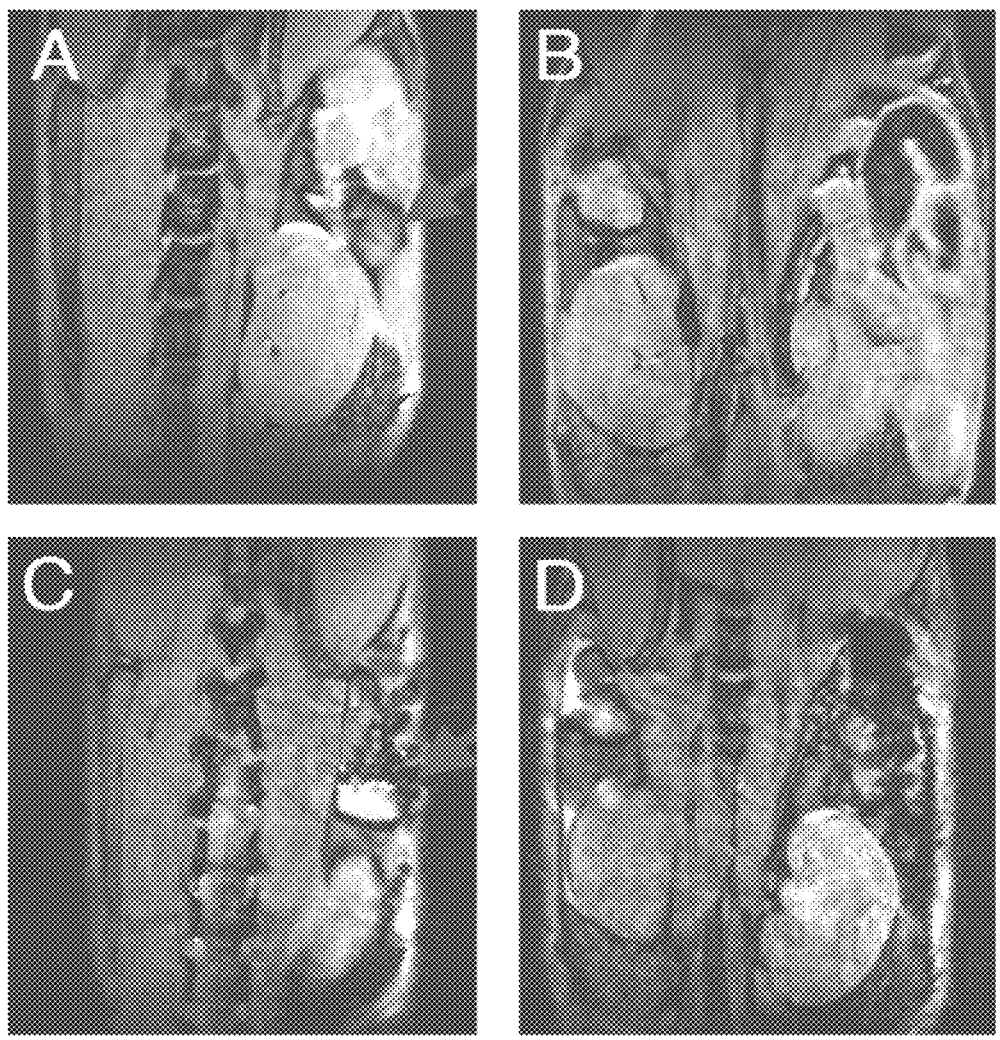
FIG. 10 shows mouse ovaries imaged before and after contrast agent 2 was injected. The arrows depict the ovary on either the left (A, C) or right (B,D) side of the body. The top two panels (A,B) were taken before injection and the bottom two panels were taken 30 minutes after 0.15 mmol/kg compound 2 was injected. Note the specific accumulation in the ovary, rich in progesterone receptors, but not in the kidney or bladder, organs that express low levels of PR.

Steroid-based Contrast Agents Accumulate and Specifically Enhance Relaxivity in the Uterus and Ovaries Experiments were performed during development of embodiments of the present invention to examine the accumulation of compound 2 in the progesterone receptor rich ovarian tissues of a female mouse in vivo. Compound 2 was suspended in DMSO and injected in the intraperitoneal cavity at a concentration of 0.15 mmol/kg weight of the mouse. The mouse was imaged prior to contrast agent to create the untreated, negative control (SEE FIGS. 10A and B). The ovaries were then identified using gradient echo imaging TR/TE (250/7 ms), array size $256^2$, and slice thickness 0.5 mm, NEX 2. The post injection images were acquired after 30 minutes (SEE FIGS. 10C and D). The ovary and uterus specifically retain compound 2 after injection. In addition, compound 2 generates a significant increase in relaxivity producing a vibrant image of a progesterone rich organ in the mouse.

Example 16

Figure 11:
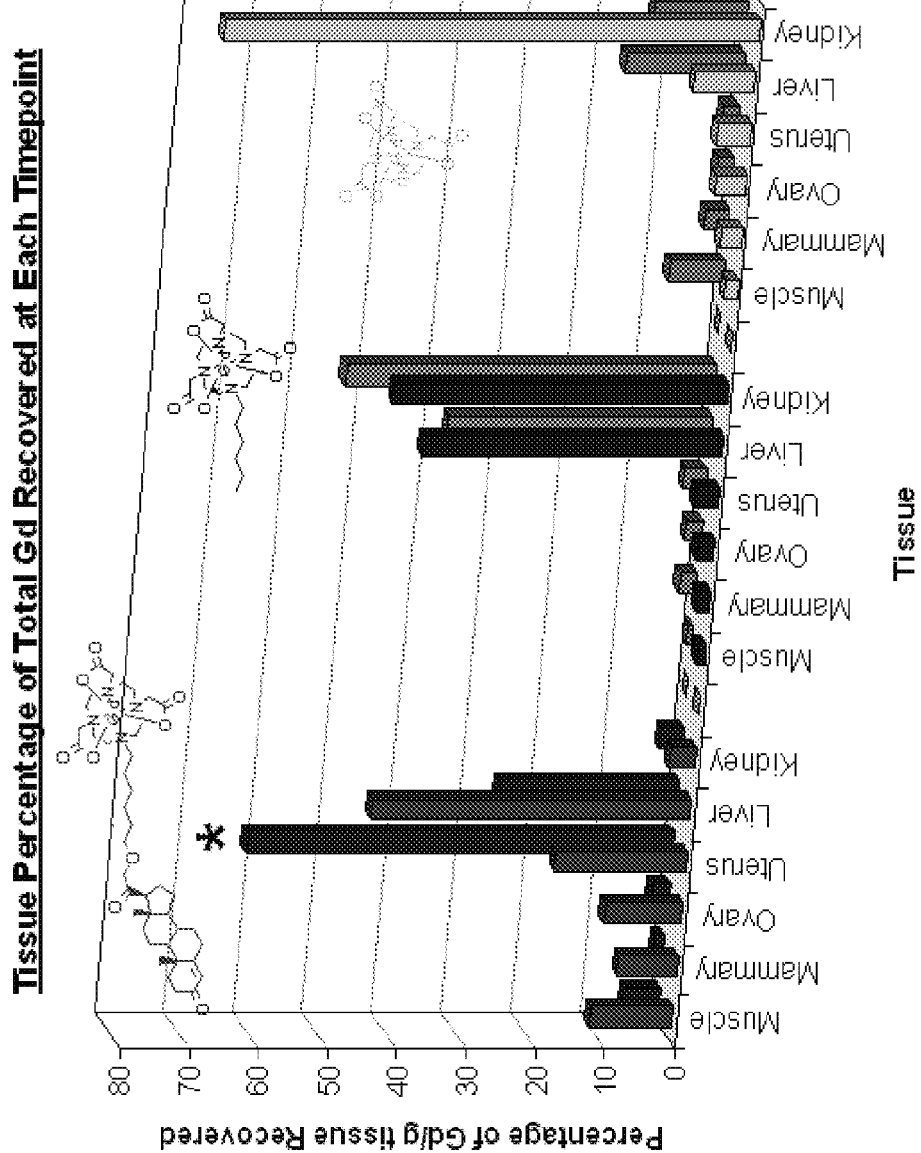
FIG. 11 shows a histogram of the percentage of Gd(III) recovered per gram of various tissues for three Gd(III) compounds (2 and 24 hour time points).
Figure 12:
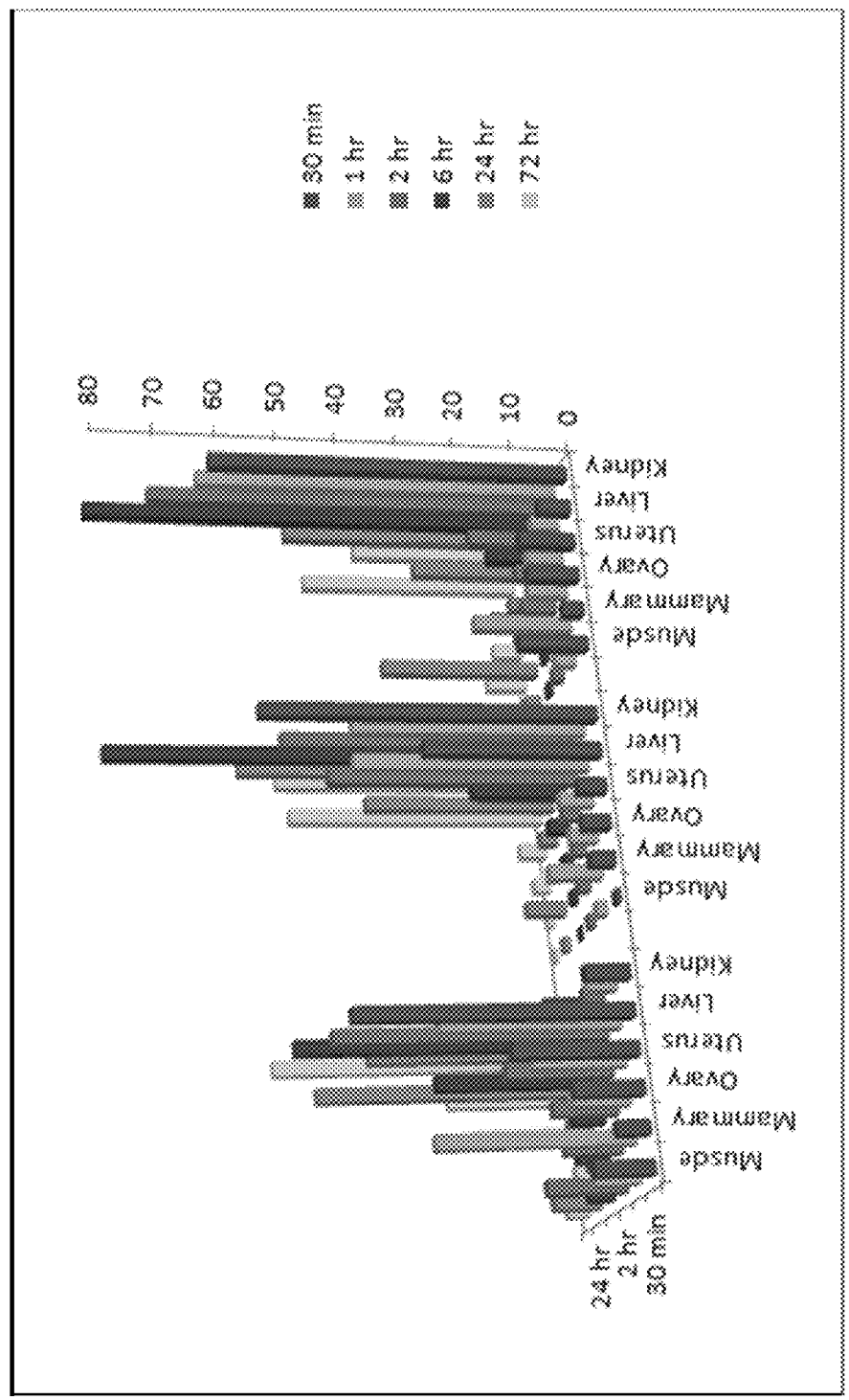
FIG. 12 shows a histogram of the percentage of Gd(III) recovered per gram of various tissues for three Gd(III) compounds (30 min, 1 hour, 2 hour, 6 hour, and 24 hour time points).

Steroid-based Contrast Agents are Retained in Tissues that Express Progesterone Receptors In Vivo A biodistribution study performed during development of embodiments of the present invention to determine whether steroid-modified contrast agents are specifically retained within cell types that express the progesterone receptor. Compound 2 was suspended in DMSO and injected into mice and the organs were harvested at 30 minute and 1, 2, 6, 24, and 72 hour timepoints. The harvested organs were dissolved by heating in concentrated nitric acid, and the Gd(III) content was determined by ICP-MS. The data was compared to biodistribution of two control compounds, hexyl-DO3A-Gd(III) (Compound 2 without the ligand moiety) and DO3A-Gd(III) (the contrast moiety of c). Data was acquired at the 30 minute, 1 hour, 2 hour, 6 hour, and 24 hour time points (SEE FIGS. 11 and 12). Gd(III) is shown as a percentage of the total Gd(III) per gram of tissue recovered from all the organs at each timepoint. The control compounds do not target any tissues and mainly end up in the liver and kidney, whereas compound 2 is retained in the uterus, which expresses PR.

Experiments were performed during development of embodiments of the present invention have demonstrated that steroid-based Gd(III) contrast agents can be synthesized, bind to their respective receptors, cross mammalian cellular membranes, drive transcription, and provide a magnetic resonance signal. The progesterone contrast agents are more specific and more cell permeable than the RU486 compounds.

Example 17

Synthesis and Evaluation of Water-Soluble Progesterone-Conjugated Probes

This Example describes the synthesis and biological evaluation of water-soluble Progesterone-Conjugated Probes and their exemplary use in magnetic resonance imaging of hormone related cancers. In particular, this Example describes the synthesis of a series of water-soluble PR-targeted MR probes. These agents demonstrated activation of PR in vitro with lower cytotoxicity than ProGlo. Higher cellular Gd(III) accumulation was observed in comparison to a nontargeted agent, particularly in PR(+) cells. Finally, these agents preferentially enhanced signal intensity in PR(+) tumors compared to PR(−) tumors and were not associated with toxicity in preliminary in vivo studies.

General Methods

Unless noted, materials and solvents were purchased from Sigma-Aldrich Chemical Co. (St. Louis, Mo.) and used without further purification. $GdCl_3 \cdot 6H_2O$ and 1,4,7,10-tetraaza-cyclododecane (cyclen) were purchased from Strem Chemicals (Newburyport, Mass.) and used without further purification. Unless noted, all reactions were performed under a nitrogen or argon atmosphere. DMSO, N,N-dimethylformamide, and methanol were purified using a Glass Contour Solvent system. Deionized water was obtained from a Millipore Q-Guard System equipped with a quantum Ex cartridge (Billerica, Mass.). Thin-layer chromatography (TLC) was performed on EMD 60F 254 silica gel plates. Visualization of the developed chromatogram was performed by CAM stain and platinum stain. Standard grade 60 Å 230-400 mesh silca gel (Sorbent Technologies) was used for flash column chromatography. $^1H$ and $^{13}C$ NMR spectra were obtained on a Bruker 500 MHz Avance III NMR Spectrometer with deuterated solvent as noted. Electrospray ionization mass spectrometry (ESI-MS) spectra were taken on a Varian 1200 L single-quadrupole mass spectrometer. High-resolution mass spectrometry data were acquired on an Agilent 6210 LC-TOF (ESI, APCI, APPI). Analytical reverse-phase HPLC-MS was performed on a Varian Prostar 500 system with a Waters Atlantis C18 column (4.6×250, 5 µm). This system is equipped with a Varian 380 LC ELSD system, a Varian 363 fluorescence detector, a Varian 335 UV-vis detector, and a Varian 1200 L Quadrupole MS detector. Preparative runs were performed on a Waters Atlantis C18 column (19×250, 10 µm). Mobile phase consisted of water (solvent A) and HPLC-grade acetonitrile (solvent B).

Synthesis

{1,4,7-Tris(carboxymethyl)-10-[10-(6-(2-((10R,13S,17S)-10,13-dimethyl-3-oxo-2,3,6,7,8,9,10,11,12,13,14,15,16,17-tetradecahydro-1H-cyclopenta[a]phenanthren-17-yl)-2-oxoethoxy)hexyl]-1,4,7,10-tetraazacyclododecanato}Gd (III) (ProGlo)

The synthesis and purification of ProGlo were performed as described above.

2-(10,13-Dimethyl-3-oxo-2,3,6,7,8,9,10,11,12,13,14,15,16,17-tetradecahydro-1H-cyclopenta[a]phenanthren-17-yl)-2-oxoethyl 5-bromopentanoate (8) A solution of 21-hydroxyprogesterone (300 mg, 1.36 mmol), 5-bromovaleric acid (111 mg, 0.613 mmol), diisopropyl carbodiimide (DIC) (122 μL, 0.786 mmol), and 4-(dimethylamino)pyridinium-4-toluenesulfonate (DPTS) (207 mg, 0.666 mmol) in anhydrous dichloromethane (1.1 mL) was stirred for 16 h at room temperature. The reaction mixture was diluted in dichloromethane and washed with water three times. The organic layer was dried over sodium sulfate and concentrated by rotary evaporation. The crude residue was purified by flash chromatography with hexanes/ethyl acetate (1:1) as the eluent to afford 8 as a white solid (348 mg, 75%). $^1$H NMR (500 MHz, $CDCl_3$) δ 5.65 (1H, s, 4-H), 4.68 (1H, d, J=17, $COCH_2O$), 4.45 (1H, d, J=17, $COCH_2O$) 3.36 (2H, t, J=6.5, $CH_2Br$), 2.47-0.80 (complex, 26H), 1.12 (3H, s, $CH_3$), 0.63 (3H, s, $CH_3$); $^{13}$C NMR (125 MHz, $CDCl_3$) δ 203.77, 199.80, 172.71, 171.17, 124.18, 69.34, 59.31, 56.41, 53.79, 51.04, 44.91, 38.81, 38.56, 35.94, 35.77, 34.16, 33.39, 32.98, 32.1, 32.2, 24.71, 23.62, 23.07, 21.22, 17.59, 13.43; ESI-MS m/z $[M+H]^+$ observed: 494.8, calculated: 495.2.

2-(10,13-Dimethyl-3-oxo-2,3,6,7,8,9,10,11,12,13,14,15,16,17-tetradecahydro-1H-cyclopenta[a]phenanthren-17-yl)-2-oxoethyl 5-azidopentanoate (10). To a solution of 8 (325 mg, 0.639 mmol) in anhydrous N,N-dimethylformamide (7 mL) was added sodium azide (415 mg, 6.39 mmol). The reaction mixture was heated to 65° C. and stirred overnight. Excess sodium azide was filtered off and the solvent was removed by rotary evaporation. The crude residue was dissolved in ethyl acetate and washed with water three times. The organic layer was dried over sodium sulfate and concentrated followed by flash chromatography in hexanes/ethyl acetate (4:3) to give 10 (206 mg, 71%). $^1$H NMR (500 MHz, $CD_3CN$) δ 5.62 (1H, s, 4-H), 4.72 (1H, d, J=17, $COCH_2O$), 4.53 (1H, d, J=17, $COCH_2O$), 3.31 (2H, t, J=6.5, $CH_2N_3$), 2.55-0.99 (complex, 26H), 1.17 (3H, s, $CH_3$), 0.64 (3H, s, $CH_3$); $^{13}$C NMR (125 MHz, $CD_3CN$) δ 204.49, 199.18, 173.04, 171.81, 123.86, 69.81, 59.25, 56.55, 54.21, 51.43, 44.95, 39.12, 38.60, 36.20, 35.94, 34.28, 33.36, 32.96, 32.52, 28.46, 24.79, 23.62, 23.07, 21.46, 17.35, 13.20. ESI-MS m/z $[M+Na]^+$ observed: 478.3, calculated: 478.3.

17-(2-((5-Bromopentyl)oxy)acetyl)-10,13-dimethyl-6,7,8,9,10,11,12,13,14,15,16,17-dodecahydro-1H-cyclopenta[a]phenanthren-3(2H)-one (7). A mixture of 21-hydroxyprogesterone (200 mg, 0.605 mmol), 1,5-dibromopentane (1.65 mL, 12.1 mmol), 40% KOH (300 μL), and tetrabutylammonium hydroxide (60 μL) was stirred for 16 h at room temperature. The reaction mixture was diluted in dichloromethane and washed with water three times. The organic layer was dried over sodium sulfate and concentrated by rotary evaporation. The crude residue was purified by flash chromatography with hexanes/ethyl acetate (2:1) as the eluent to afford 7 as a colorless oil (125 mg, 43%). $^1$H NMR (500 MHz, $CDCl_3$) δ 5.67 (s, 1H), 3.96 (q, J=17.2 Hz, 2H), 3.41 (t, J=6.4 Hz, 2H), 3.38-3.31 (m, 2H), 2.56 (t, J=9.1 Hz, 1H), 2.40-2.09 (m, 6H), 1.96 (m, 1H), 1.90-1.74 (m, 5H), 1.72-1.16 (m, 14H), 1.12 (s, 3H), 1.05-0.86 (m, 2H), 0.65-0.58 (m, 3H). $^{13}$C NMR (125 MHz, $CDCl_3$) δ 207.55, 198.50, 169.94, 122.92, 75.79, 70.34, 61.56, 57.43, 55.12, 52.51, 43.53, 37.54, 34.61, 32.85, 31.74, 31.47, 30.82, 28.69, 27.74, 23.77, 23.47, 21.81, 19.97, 16.34, 12.55. ESI-MS m/z $[M+H]^+$ observed: 481.1, calculated: 481.2.

17-(2-((5-Azidopentyl)oxy)acetyl)-10,13-dimethyl-6,7,8,9,10,11,12,13,14,15,16,17-dodecahydro-1H-cyclopenta[a]phenanthren-3(2H)-one (9). To a solution of 7 (125 mg, 0.261 mmol) in anhydrous N,N-dimethylformamide (7 mL) was added sodium azide (169 mg, 2.61 mmol). The reaction mixture was heated to 65° C. and stirred overnight. Excess sodium azide was filtered off and the solvent was removed by rotary evaporation. The crude residue was dissolved in ethyl acetate and washed with water three times. The organic layer was dried over sodium sulfate and concentrated followed by flash chromatography in hexanes/ethyl acetate (2:1) to give 9 (78 mg, 68%). $^1$H NMR (500 MHz, $CD_3OD$) δ 5.61 (d, J=4.9 Hz, 1H), 3.39 (t, J=6.4 Hz, 2H), 3.25-3.17 (m, 4H), 2.60 (t, J=9.1 Hz, 1H), 2.45-2.33 (m, 2H), 2.25-2.15 (m, 2H), 2.12-2.03 (m, 1H), 1.99 (m, 1H), 1.89-1.76 (m, 2H), 1.70-1.29 (m, 15H), 1.29-1.15 (m, 2H), 1.13 (d, J=11.0 Hz, 4H), 1.04-0.87 (m, 2H), 0.60 (s, 3H). $^{13}$C NMR (125 MHz, $CD_3OD$) δ 210.81, 202.29, 174.92, 124.24, 78.00, 72.34, 62.71, 59.71, 57.39, 55.16, 52.43, 45.67, 39.99, 39.72, 36.81, 34.72, 33.90, 33.20, 30.15, 29.75, 25.52, 24.46, 24.17, 23.76, 22.15, 17.67, 13.96. ESI-MS m/z $[M+Na]^+$ observed: 464.2, calculated: 464.3.

General Procedure for Click Chemistry

All click chemistry reactions were run in 1:1 methanol/water or 1:1 DMSO/water solutions. The steroid derivative (1 equiv) and Gd(III) or Eu(III) chelate (1.1 equiv) were dissolved and $N_2$ gas was bubbled through the solution to remove oxygen. Sodium ascorbate (1 equiv), $CuSO_4$ (0.167 equiv), and [(1-benzyl-1H-1,2,3-triazol-4-yl)methyl]amine (TBTA) (0.02 equiv) were added and the reaction mixture was stirred at 60° C. for 24 h. The crude residue was purified by reverse-phase preparative HPLC using a ramp from 0% to 100% B over 20 min.

Figure 13:
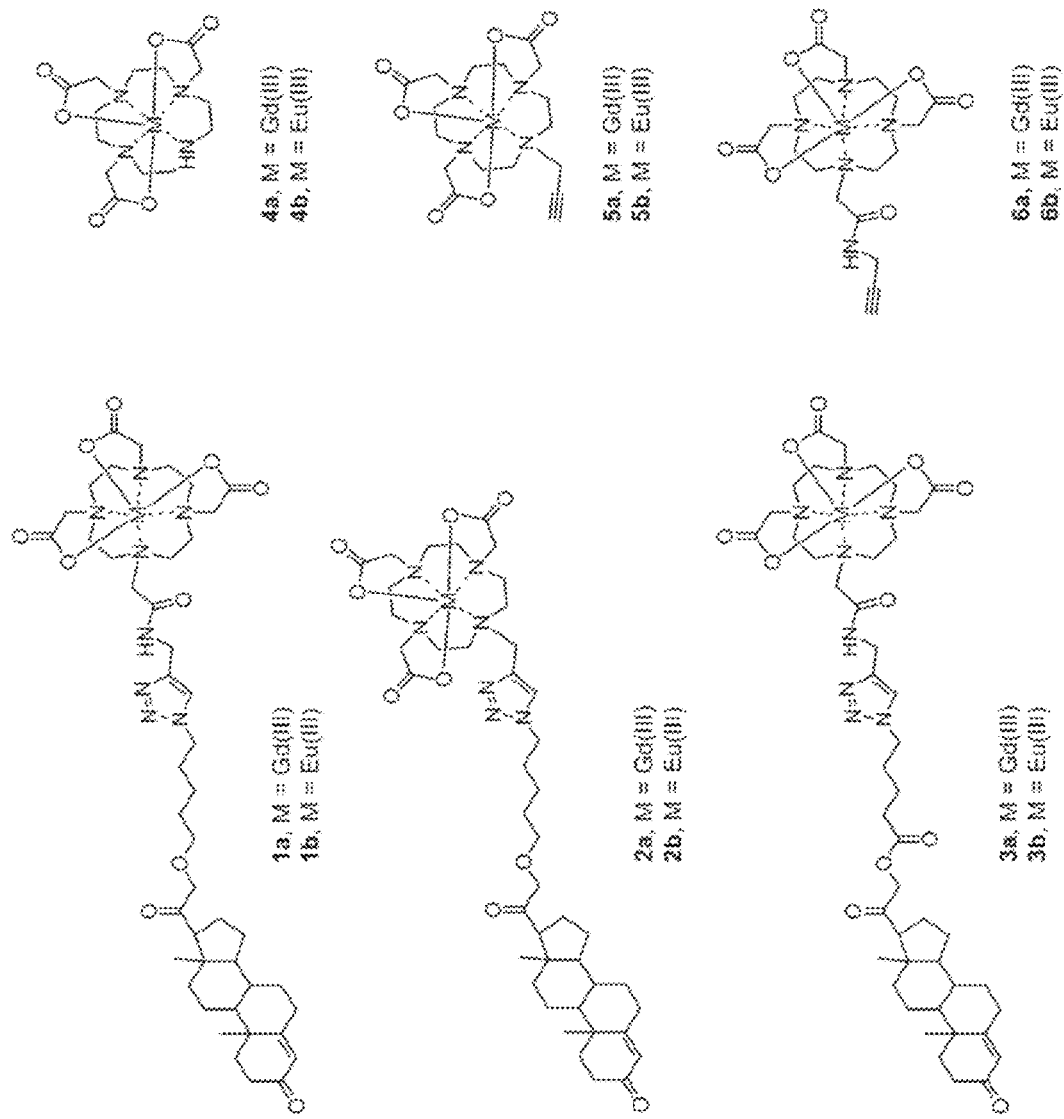
FIG. 13 shows the chemical structures of the PR-targeted agents (1a, 1b, 2a, 2b, 3a, and 3b) and the nontargeted control agents (4a, 4b, 5a, 5b, 6a, and 6b) used in Example 17.

{2,2',2''-(10-(2-(((1-(5-(2-(10,13-Dimethyl-3-oxo-2,3,6,7,8,9,10,11,12,13,14,15,16,17-tetradecahydro-1H-cyclopenta[a]phenanthren-17-yl)-2-oxoethoxy)pentyl)-1H-1,2,3-triazol-4-yl)methyl)amino)-2-oxoethyl)-1,4,7,10-tetraazacyclododecane-1,4,7-triyl)triacetate}gadolinium (1a; FIG. 13). HRMS (ESI) m/z $[M+H]^+$ observed: 1034.4231, calculated: 1034.4267 for $C_{45}H_{68}GdN_8O_{10}$.

{2,2',2''-((10-((1-(5-(2-(10,13-Dimethyl-3-oxo-2,3,6,7,8,9,10,11,12,13,14,15,16,17-tetradecahydro-1H-cyclopenta[a]phenanthren-17-yl)-2-oxoethoxy)pentyl)-1H-1,2,3-triazol-4-yl)methyl)-1,4,7,10-tetraazacyclododecane-1,4,7-triyl)triacetate}gadolinium (2a; FIG. 13). HRMS (ESI) m/z $[M+H]^+$ observed: 977.4066, calculated: 977.40524 for $C_{43}H_{65}GdN_7O_9$.

{2,2',2''-(10-(2-(((1-(5-(2-(10,13-Dimethyl-3-oxo-2,3,6,7,8,9,10,11,12,13,14,15,16,17-tetradecahydro-1H-cyclopenta[a]phenanthren-17-yl)-2-oxoethoxy)-5-oxopentyl)-1H-1,2,3-triazol-4-yl)methyl)amino)-2-oxoethyl)-1,4,7,10-tetraazacyclododecane-1,4,7-triyl)triacetate}gadolinium (3a; FIG. 13). HRMS (ESI) m/z $[M+H]^+$ observed: 1049.4078, calculated: 1049.40775 for $C_{45}H_{66}GdN_8O_{11}$.

{2,2',2''-(10-(2-(((1-(5-(2-(10,13-Dimethyl-3-oxo-2,3,6,7,8,9,10,11,12,13,14,15,16,17-tetradecahydro-1H-cyclopenta[a]phenanthren-17-yl)-2-oxoethoxy)pentyl)-1H-1,2,3-triazol-4-yl)methyl)amino)-2-oxoethyl)-1,4,7,10-tetraazacyclododecane-1,4,7-triyl)triacetate}europium (1b; FIG. 13). HRMS (ESI) m/z $[M+H]^+$ observed: 1031.4252, calculated: 1031.4256 for $C_{45}H_{68}EuN_8O_{10}$.

{2,2',2''-(10-(((1-(5-(2-(10,13-Dimethyl-3-oxo-2,3,6,7,8,9,10,11,12,13,14,15,16,17-tetradecahydro-1H-cyclopenta

[a]phenanthren-17-yl)-2-oxoethoxy)pentyl)-1H-1,2,3-triazol-4-yl)methyl)-1,4,7,10-tetraazacyclododecane-1,4,7-triyl)triacetate}europium (2b; FIG. 13). HRMS (ESI) m/z [M+H]$^+$ observed: 974.4058, calculated: 974.40416 for $C_{43}H_{65}EuN_7O_9$.

{2,2',2"-(10-(2-(((1-(5-(2-(10,13-Dimethyl-3-oxo-2,3,6,7,8,9,10,11,12,13,14,15,16,17-tetradecahydro-1H-cyclopenta[a]phenanthren-17-yl)-2-oxoethoxy)-5-oxopentyl)-1H-1,2,3-triazol-4-yl)methyl)amino)-2-oxoethyl)-1,4,7,10-tetraazacyclododecane-1,4,7-triyl)triacetate}europium (3b; FIG. 13). HRMS (ESI) m/z [M+H]$^+$ observed: 1045.4074, calculated: 1045.40487 for $C_{45}H_{66}EuN_8O_{11}$.

Relaxivity

Solutions of 1a, 2a, 3a, 4a, 5a, and 6a were prepared in 500 µL, of Millipore water for $T_1$ and $T_2$ acquisition. $T_1$ and $T_2$ relaxation times were measured on a Bruker mq60 NMR analyzer equipped with Minispec v 2.51 rev. 00/NT software (Billerica, Mass., USA) operating at 1.41 T (60 MHz) and 37° C. $T_1$ relaxation times were measured using an inversion recovery pulse sequence using the following parameters: 4 scans per point, 10 data points for fitting, monoexponential curve fitting, phase cycling, 10 ms first pulse separation, and a recycle delay and final pulse separation of $\geq 5$ $T_1$. The Gd(III) concentration of each solution was determined using ICP-MS. The inverse of the relaxation time ($1/T_1$, s$^{-1}$) was plotted against Gd(III) concentration (mM) and fitted to a straight line with $R^2 > 0.99$. The slope of the fitted line was recorded as the relaxivity, $r_1$.

Octanol-Water Partition Coefficients

Approximately 1 mg of each compound was dissolved in 1 mL of a 1:1 mixture of water/1-octanol. After shaking the sample tube vigorously for 30 s, the tube was placed on a rotator for gentle mixing over 4 h. The tube was then removed from the rotator and allowed to sit for 10 h to ensure complete separation of the aqueous and organic phases. 50 µL, was removed from each layer and subjected to ICP-MS to determine the Gd concentration in each layer. The partition coefficient was calculated from the following equation: $\log_{10} P = \log_{10}(C_o/C_w)$, where $\log_{10} P$ is the logarithm of the partition coefficient, $C_o$ is the concentration of Gd in the 1-octanol layer, and $C_w$ is the concentration of Gd in the water layer.

Determination of q

The Eu(III) complexes were dissolved in $D_2O$ and $H_2O$. The emission was monitored at 614 nm with excitation at 395 nm on a Hitachi F4500 fluorescence spectrophotometer operating in phosphorescence lifetime mode. Twenty-five scans were averaged and fit to a monoexponential decay ($R^2 > 0.98$) to give the phosphorescent lifetimes which were entered into this equation (corrected for one amide oscillator): $q = 1.0 (k_{H2O} - k_{D2O} - 0.25 - 0.075)$. (24, 25)

Receptor Binding to nPR

The progesterone receptor A ligand binding domain (amino acids 675-933) fused to GST (PR-LBD-GST; 80 nM), a fluorescently tagged PR ligand (fluoromone green PL; 4 nM), and progesterone, ProGlo, 1a, or 3a (several concentrations) were incubated in PR screening buffer with 4 mM dithiothreitol (DTT) in a total volume of 100 µL for 4 h at room temperature according to the manufacturer's protocol (Invitrogen, Carlsbad, Calif., USA). Each sample was measured using the Beacon 2000 fluorescence polarization analyzer (Invitrogen, Carlsbad, Calif.) located in the Northwestern University Keck Facility. The machine was used in static mode, batch blank, no delay, with an average of 1 read per cycle, at 22° C. A sample containing only buffer and PR-LBD-GST with no fluorescent PL was used as the blank to eliminate background signal from the protein or buffer. A sample with no competitor was used to determine 100% binding capacity of the PR-LBD-GST for the PL ligand. Curve fitting and error calculation was performed using Prism software from GraphPad Software, Inc. (La Jolla, Calif.).

General Cell Culture

Dulbecco's modified phosphate buffered saline (DPBS), media, sera, and dissociation reagents were purchased from Invitrogen (Carlsbad, Calif.). Cell culture consumables (flasks, plates, etc.) were purchased from VWR (Radnor, Pa.). Charcoal dextran stripped FBS was purchased from Atlanta Biologicals (Lawrenceville, Ga.). MDA-MB-231 cells were cultured using phenol red free α-MEM (modified to contain 20 ng/mL insulin) supplemented with 10% FBS (characterized) or with 10% charcoal dextran stripped FBS. T47D cells were cultured using phenol red free RPMI 1640 (modified to contain 1.0 mM sodium pyruvate, 1.0 mM HEPES, and 4.5 g/L glucose) supplemented with 10% FBS or 10% charcoal dextran stripped FBS. Prior to all experiments, cells were plated in the appropriate medium containing noncharcoal dextran stripped FBS. After plating, this medium was replaced with medium containing the stripped FBS and allowed to sit for 24 h, at which point the medium was replaced with fresh stripped medium and the cells were allowed to sit for another 24 h prior to beginning the experiment. MDA-MB-231 and T47D cells were harvested by incubation with 0.25% TrypLE for 10 min at 37° C. in a 5.0% $CO_2$ incubator. All incubations were carried out at 37° C. in a 5.0% $CO_2$ incubator unless otherwise specified.

Cell Counting and Percent Cell Viability Determination Using Guava EasyCyte Mini Personal Cell Analyzer (PCA) System After cell harvesting, an aliquot (15 or 30 µL) of the cell suspensions were mixed with Guava ViaCount reagent (final sample volume of 150 µL) and allowed to stain at room temperature for at least 5.0 min (no longer than 20 min). Stained samples were then vortexed for 10 s, after which cells were counted and percent cell viability determined via manual analysis using a Guava EasyCyte Mini Personal Cell Analyzer (PCA) and ViaCount software module. For each sample, 1000 events were acquired with dilution factors that were determined based upon optimum machine performance (~25-70 cells/µL). Instrument reproducibility was assessed daily using GuavaCheck Beads and following the manufacturer's suggested protocol using the Daily Check software module.

Cellular Uptake Studies

Contrast agents were dissolved in the appropriate medium (containing stripped FBS) for each cell line (T47D and MDA-MB-231) at concentrations of 2, 1, 0.5, 0.25, and 0.125 mM of contrast agent. For concentration-dependent cellular uptake, cells were incubated with 2, 1, 0.5, and 0.25 mM of each contrast agent for 4 h. For the time dependent cellular uptake, cells were incubated with 0.125 mM contrast agent for 1, 4, 10, and 24 h. After incubation, the media was removed, and the cells were rinsed twice with PBS and trypsinized. An aliquot was used for cell counting and the remaining portion was analyzed for Gd(III) content by ICP-MS. Each condition was done in triplicate.

Fractionation of Nuclear, Cytoplasmic, and Membrane Components

T47D and MDA-MB-231 cells were incubated with 0.250 mM of contrast agent (in the appropriate medium containing stripped FBS) for 10 h. After incubation, the cells were rinsed twice with PBS, trypsinized, pelleted (500 g for 5 min), and resuspended in PBS. A portion was removed for cell counting, and the rest was pelleted (500 g for 5 min) and the PBS removed. Cytoplasmic and nuclear fractions were extracted using a NE-PER Nuclear and Cytoplasmic Extraction Kit according to manufacturer protocol (Pierce, Rockford, Ill.). The remaining pellet after cytoplasmic and nuclear extraction was assumed to consist mainly of membrane. Each fraction was analyzed for Gd(III) content by ICP-MS.

Cytotoxicity

The CellTiter 96 A$_{Queous}$ Non-Radioactive Cell Proliferation Assay (Promega, Madison, Wis.) was used to measure cell viability. Cells were plated at 5000 cells/well in 96 well plates and maintained in medium containing stripped serum for 48 h before beginning the experiment. ProGlo, progesterone, 1a, 2a, 3a, and 4a were dissolved in varying concentrations in media. After 24 h of incubation, the assay was run according to manufacturer protocol. Absorbance was measuring using a Biotek Synergy4 microplate reader in the High Throughput Analysis Facility at Northwestern University.

Luciferase Assay for nPR Activation

T47D cells were grown in phenol-free medium, and cells were trypsinized and plated in 24-well plate (50 000 cells/well). Incubation of cells with the pPRE-luciferase plasmid (100 ng/well, construct provided by Dr. Ken Korach, NIEHS, NIH), RSV-β-galactosidase (100 ng/well, provided by Dr. William T. Beck, University of Illinois at Chicago), and Lipofectamine 2000 (1 µL per well, Invitrogen, Carlsbad, Calif.) in Opti-MEM was performed overnight at 37° C. inside a humidified incubator. The cells were treated with 1a, 2a, 3a, and 4a for an additional 24 h.

To measure luciferase production, cells were lysed in 100 µL GME buffer (25 mM glycylglycine at pH 7.8, 15 mM MgSO$_4$, 4 mM EGTA, 1 mM dithiothreitol, and 1% Triton X-100) and lysates were added to assay buffer (GME buffer, 16.5 mM KPO$_4$, 2.2 mM ATP, and 1.1 mM dithiothreitol). Luciferase substrate was injected followed by a 30 s read by a FLUOstar OPTIMA (BMG Lab Tech, Offenburg, Germany). LacZ activity (50 µL lysate) was measured from cleavage of ONPG. The sample results were normalized to β-galactosidase to account for transfection efficiency by dividing the sum of the luciferase activity by the sum of the β-galactosidase activity. Fold change was calculated by taking the luciferase value, dividing by the β-galactosidase activity, and then dividing by the solvent control, which was set equal to one.

RT-PCR

Total RNA was isolated using Qiagen RNA easy columns with on column DNase added according to the manufacture (Qiagen, Valencia, Calif.). RNA samples (2 µg) were then primed with random hexamers and reverse transcribed with M-MLV Reverse Transcriptase (Promega, Madison, Wis.) according to manufacturer's instructions. From the original RT reaction, 1 µL was subjected to PCR amplification in a 25 µL volume with Taqman Universal PCR SYBR Green Master Mix (Applied Biosystems, Foster City, Calif.) under the following conditions: 50° C. hold 2 min, 95° C. hold for 10 min, the 40 cycles of 95° C. for 15 s, 65° C. for 30 s, and 72° C. for 1 min. The primers used were designed using Integrated DNA technologies primer quest for ZBTB16 forward 5'TGTTTGAGATCCTCTTCCACCGCA3' (SEQ ID NO:1) and reverse 5' TCTCCAGCATCTTCAGGCACTGTT3' (SEQ ID NO:2) and normalized to GAPDH forward 5' ATGGGGAAGGTGAAGGTCG3' (SEQ ID NO:3) and reverse 5'GGGGTCATTGATGGCAACAATA3' (SEQ ID NO:4).

ICP-MS Sample Preparation and Instrument Parameters

For octanol-water partition coefficients, relaxivity, and cell studies, ACS reagent grade nitric acid (70%) was added to solutions of the agent in water or 1-octanol, cell suspensions, and media (for a 1.0:1.0 v/v sample/nitric acid) in 15 mL conical tubes and placed at 65° C. for at least 4.0 h to allow for complete sample digestion. For samples in 1-octanol, tubes were vented every 30 min due to buildup of pressure. Nanopure H$_2$O and internal standard (either indium or multielement) were added to produce a final solution of 3.0% nitric acid (v/v) and 5.0 ng/mL internal standard. Gd(III) standards were prepared at 0.10, 0.25, 0.50, 1.0, 5.0, 10, 25, and 50 ng/mL concentrations with 3.0% nitric acid (v/v) and internal standard final concentrations. ICP-MS was performed on a computer-controlled Thermo (Waltham, Mass.) X Series II inductively coupled plasma mass spectrometer equipped with a CETAC 260 autosampler. Each sample was acquired using 1 survey run and 3 main (peak jumping) runs. The isotopes selected were $^{156,157}$Gd, as well as $^{115}$In and $^{165}$Ho (as internal standards for data interpolation and machine stability).

Animal Experiments

Female Balb/C athymic nude mice were acquired from Harlan (Indianapolis, Ind.) and housed under pathogen free conditions. All animal studies were conducted at Northwestern University in accordance with the National Institutes of Health Guide for the Care and Use of Laboratory Animals and established institutional animal use and care protocols. Due to low circulating estradiol levels in nude mice, a 17β-estradiol pellet (Innovative Research of America, Sarasota, FA, 70-day release, 0.72 mg/pellet) was implanted subcutaneously in the nape of the neck to ensure growth of estrogen-dependent T47D cells. Two to seven days later, T47D and MDA-MB-231 ((1–2)×10$^6$) cells were suspended in Matrigel (1:1 volume) and injected subcutaneously into the rear flank (T47D cells on the right side and MDA-MB-231 cells on the left). Mice were monitored for tumor growth every two to three days after injection of cells. Mice were imaged two to three weeks after xenografting when tumors were palpable with a minimum weight of 20 mg (determined after tumor removal postimaging).

In Vivo MR Imaging

Xenografted nude mice were injected intraperitoneally (n=1 per compound) with each agent (0.15 mmGd/kg) dissolved in 50 µL, DMSO. During imaging, mice were maintained under anesthesia (1-3% isoflurane) but were allowed to wake up and recover between imaging time points. Tubing containing heated water was positioned under the mouse to keep a constant body temperature. All MR imaging was performed on a 89 mm bore size PharmaScan 7.05 T MR imager fitted with shielded gradient coils (Bruker BioSpin, Billerica, Mass., USA) using a RF RES 300 1H 089/038 quadrature transmit receive volume coil (Bruker BioSpin, Billerica, Mass., USA). Standard T$_1$-weighted multislice multiecho (MSME) scans with fat suppression were used for imaging the uterus, ovaries, and xenografts: TR=700 ms, TE=10.635 ms, FOV=35×35 mm, matrix size=256×256, slice thickness=1.0 mm, contiguous slices. Images were analyzed using ImageJ. Contrast-to-noise ratio (CNR) was calculated using the equation CNR=(SI$_{Tissue}$−SI$_{muscle}$)/σ$_{noise}$ where SI$_{Tumor}$ is the signal intensity in the tumor, SI$_{Muscle}$ is the signal intensity in the muscle, and σ$_{noise}$ is the standard deviation of the noise. CNRs were averaged over two to three axial slices in which the tumors were clearly demarcated.

Results

Click Chemistry Synthesis of Water-Soluble PR-Targeted MRI Contrast Agents

In order to increase the solubility of ProGlo while attempting to retain its biological properties, the core structure of the targeting steroid and the Gd(III) chelate were maintained while the linker was modified. The structures of the new PR-targeted agents and nontargeted control agents used in this Example are presented in FIG. 13.

Figure 14:
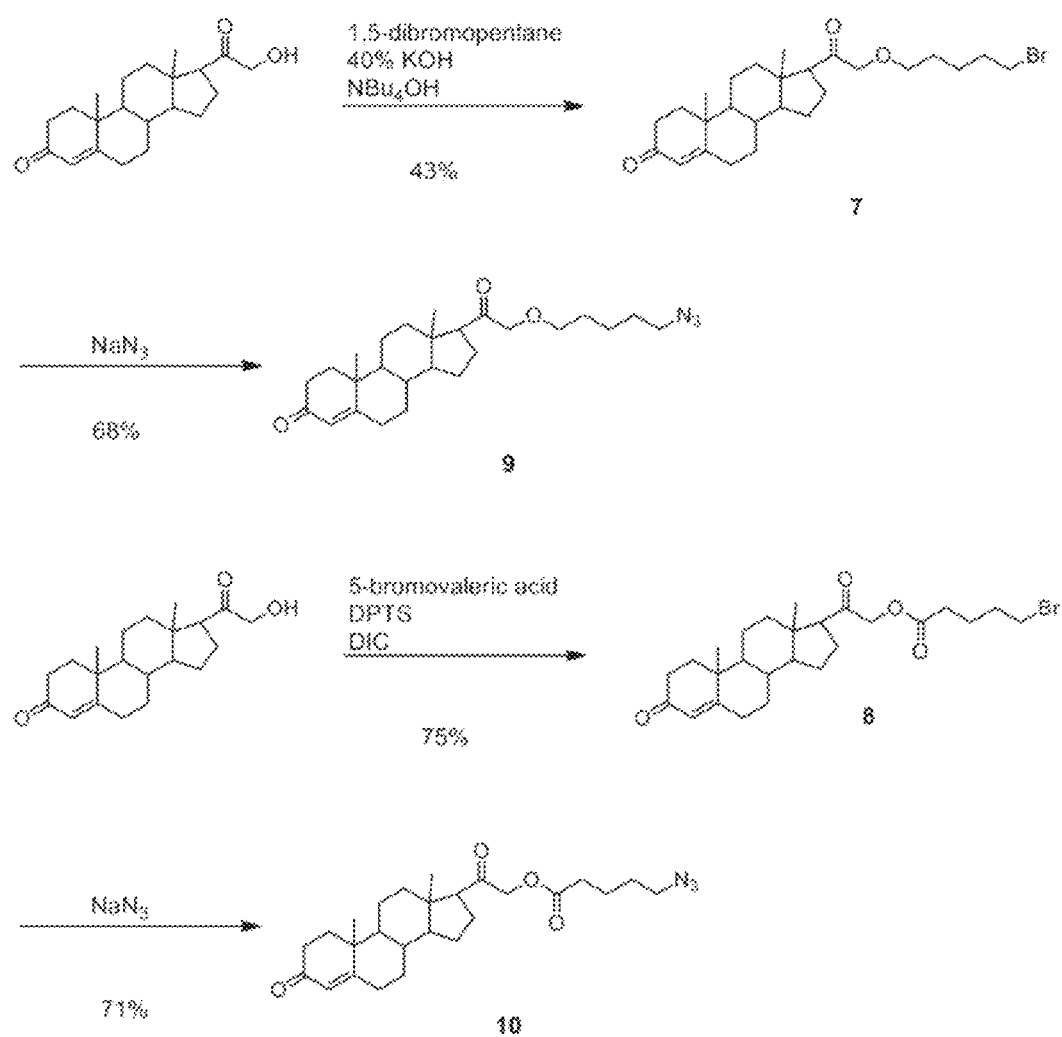
FIG. 14 shows the synthesis of the azide derivatives of progesterone from Example 17, where 9 and 10 were synthesized and coupled to the alkyne-functionalized Gd(III) or Eu(III) chelates via Cu(I)-catalyzed click chemistry.
Figure 15:
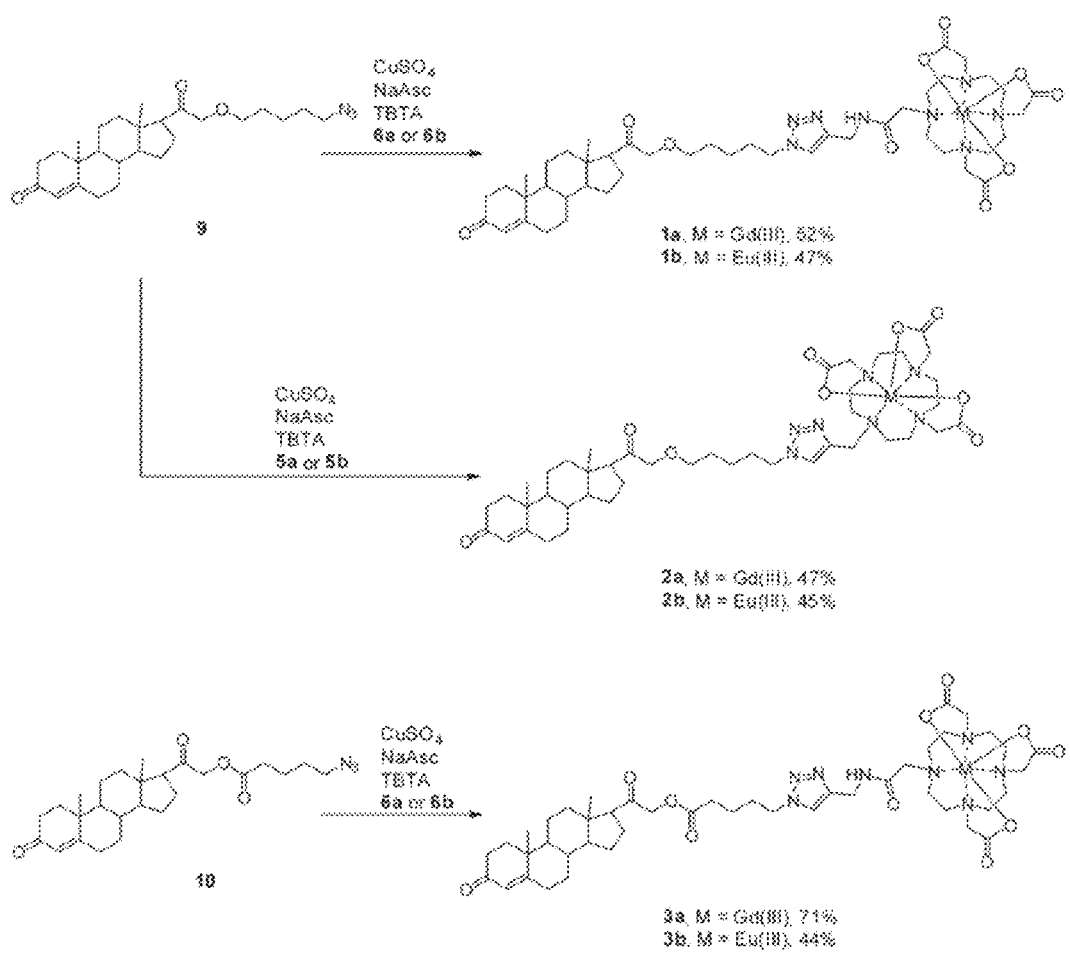
FIG. 15 shows synthesis of the water-soluble progesterone-conjugated MRI contrast agents via copper-catalyzed click chemistry as described in Example 17.

The synthesis of each water-soluble PR-targeted agent began with the coupling of 1,5-dibromopentane or 5-bromovaleric acid to 21-hydroxyprogesterone off the 21-hydroxyl group because PR is known to accommodate bulky substituents on the D ring of the progesterone.(17, 26, 27). Reaction with sodium azide yielded the azido derivative of these steroids (FIG. 14). Using copper-catalyzed click chemistry (Scheme 2), (28, 29) these steroid derivatives were attached to alkyne-functionalized Gd(III) chelates, 5a and 6a, which were synthesized using modifications of previously reported procedures.(19, 30-34). FIG. 15 shows the synthesis of water-soluble progesterone-conjugated MRI contrast agents via copper-catalyzed click chemistry.

Relaxivities, Hydration Numbers, and Octanol-Water Partition Coefficients of Progesterone-Conjugated MRI Probes The longitudinal relaxivities of the PR-targeted agents and 4a are similar to those reported for clinically used contrast agents, about 4-5 mM$^{-1}$ s$^{-1}$ (Table 1).(35, 36) Like most clinically used contrast agents, each of the PR-targeted agents has approximately one water molecule bound to the Gd(III), as determined by analysis of hydration number (q) on the Eu(III) analogues of these agents (Table 1). For complex 2b, the coordination of one water molecule, rather than two, indicates that the triazole ring from the click reaction coordinates to the Gd(III), an effect that was previously reported. (33) For 3b and 1b, the q of one is due to the coordination of the amide group back to the metal.

TABLE 1

Characterization of the Water-Soluble PR-Targeted Agents and Nontargeted Control Agents

| agent[a] | $r_1$ (mM$^{-1}$ s$^{-1}$)[b] | $r_2$ (mM$^{-1}$ s$^{-1}$)[b] | q | log P | RBA |
|---|---|---|---|---|---|
| 1 | 4.16 ± 0.05 | 4.78 ± 0.26 | 0.75 | −0.37 ± 0.09 | 0.40% |
| 2 | 4.16 ± 0.50 | 4.48 ± 0.33 | 1.03 | −0.59 ± 0.04 | n.d.[c] |
| 3 | 4.26 ± 0.13 | 4.90 ± 0.14 | 1.24 | −0.27 ± 0.08 | 0.29% |
| ProGlo | 5.35 ± 0.74 | 6.14 ± 0.81 | n.d. | 1.40 ± 0.08 | 0.45% |
| 4 | 4.05 ± 0.018 | 4.75 ± 0.35 | 2.13 | −2.96 ± 0.35 | n.d. |
| 5 | 4.98 ± 0.069 | 5.64 ± 0.24 | 2.16 | n.d. | n.d. |
| 6 | 3.36 ± 0.11 | 3.89 ± 0.20 | 1.21 | n.d. | n.d. |

[a]Gd(III) complexes (1a-6a) were used for measuring relaxivities, log P, and RBA; Eu(III) complexes (1b-6b) were used for measuring q.
[b]1.41 T, 37° C.
[c]n.d. = not determined.

Octanol-water partition coefficients (log P) were measured to determine the hydrophobicity of these agents, which correlates to the cellular permeability and tissue distribution (Table 1).(21, 37) The negative log P value for 4a was characteristic of its high water solubility. The log P values of these water-soluble PR-targeted agents are between the values for ProGlo and 4a, indicating an intermediate hydrophobicity.

High Receptor Binding Affinity is Maintained by Progesterone-Modified Gd(III) Chelates These water-soluble agents were expected to have receptor binding affinities similar to that of ProGlo because the chemical modification occurred at the same position on the steroid. Compounds 1a and 3a were chosen to compare the effect of the ether to an ester linker in terms of PR binding (2a was not tested because this molecule has the same linker as 1a). The relative binding affinities (RBAs) of these agents and of ProGlo were measured (Table 1). Both 1a and 3a have RBAs similar to that of ProGlo and about 100-fold less than that of progesterone. These results are consistent with previously published data that demonstrated approximately 100-fold lower binding affinity of ProGlo compared to unmodified progesterone.(17) Although 3a demonstrated a minimal decrease in binding affinity (likely due to the presence of the additional carbonyl), the RBAs of these agents indicate that the modifications made to the linker did not significantly affect their ability to bind PR as compared to ProGlo.

Progesterone-Conjugated MRI Probes Demonstrate Enhanced Cellular Association

Figure 16:
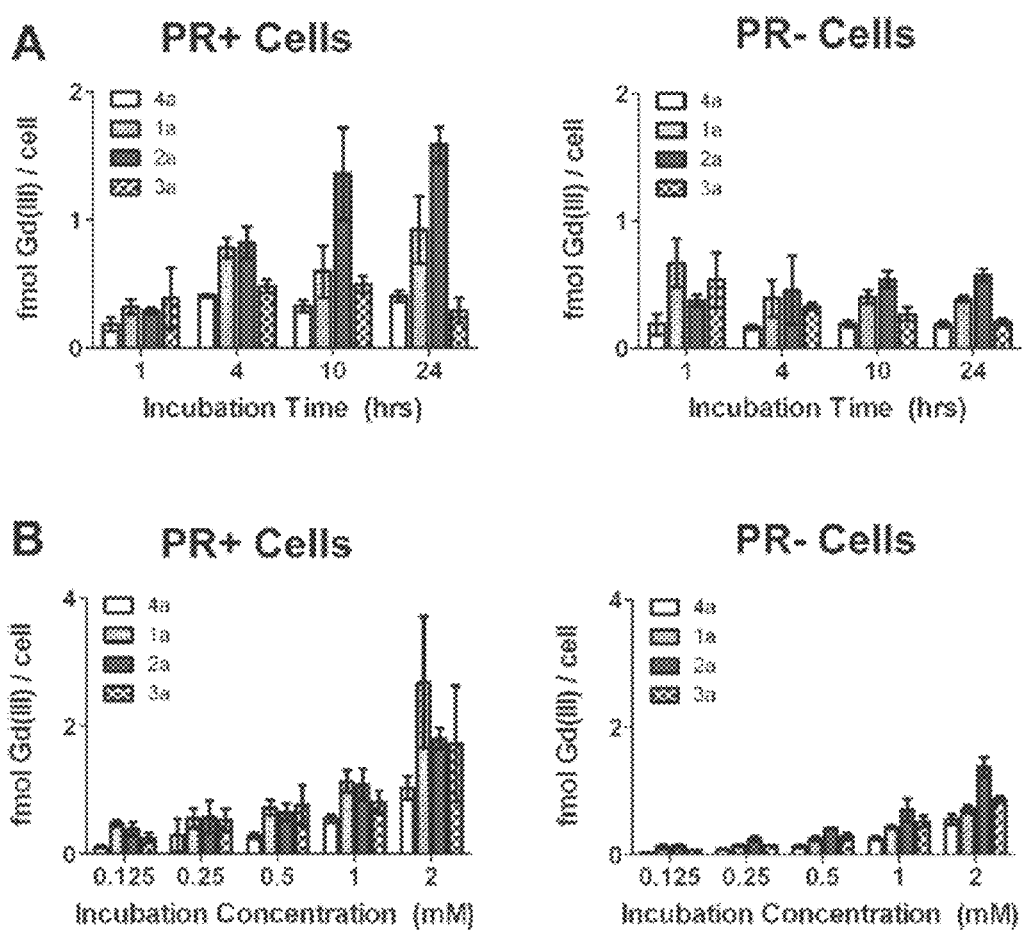
FIG. 16 shows cellular uptake of PR-targeted agents and nontargeted control from Example 17. (A) Time-dependent cellular uptake of Gd(III) in PR(+) versus PR(−) cells after incubation with 4a, 1a, 2a, and 3a. (B) Concentration-dependent cellular uptake of Gd(III) in PR(+) versus PR(−) cells after incubation with 4a, 1a, 2a, and 3a. Error bars represent mean±standard deviation.

To determine the cell permeability of the compounds, PR(+) (T47D) and PR(−) (MDA-MB-231) human breast cancer cells were incubated with 1a, 2a, 3a, and 4a. Time- and concentration-dependent experiments were performed to identify the optimal dose and incubation times of the agents (FIG. 16). Each agent demonstrated increased cellular Gd(III) accumulation with increased incubation concentrations in both cell lines. However, time-dependent accumulation was observed only for 2a in the PR(+) cells. The uptake of 1a in the PR(+) cells increased slightly after 1 h and then stabilized, while the Gd(III) levels in PR(+) cells incubated with 3a had decreased by 24 h in comparison to earlier time points. No time dependence in uptake was seen in PR(−) cells as the Gd(III) levels remained constant at all time points or even decreased (for 3a). The uptake of the steroid-conjugated agents was higher than that of 4a at all time points and cell lines, except for 3a, which showed equal or lower Gd(III) than 4a at the 24 h time point in both cell lines. These results indicate that the presence of the steroid moiety encourages cellular uptake of the targeted contrast agents when compared to the nonfunctionalized Gd(III) chelate.

Importantly, the Gd(III) accumulation of the PR-targeted agents was significantly higher in PR(+) than in PR(−) cells. While the uptake of 4a was higher in PR(+) cells than in PR(−) cells, the difference in uptake was lower than for the progesterone-conjugated agents (particularly 1a and 2a). These data indicate that conjugation with progesterone increases the ability of Gd(III) contrast agents to associate with cells. In addition, the increased Gd(III) accumulation in PR(+) cells compared to PR(−) cells suggests that PR likely plays a role in the accumulation and retention of these progesterone-conjugated agents.

Water-Soluble PR-Targeted Agents Cross the Cell Membrane and Activate PR

Figure 17:
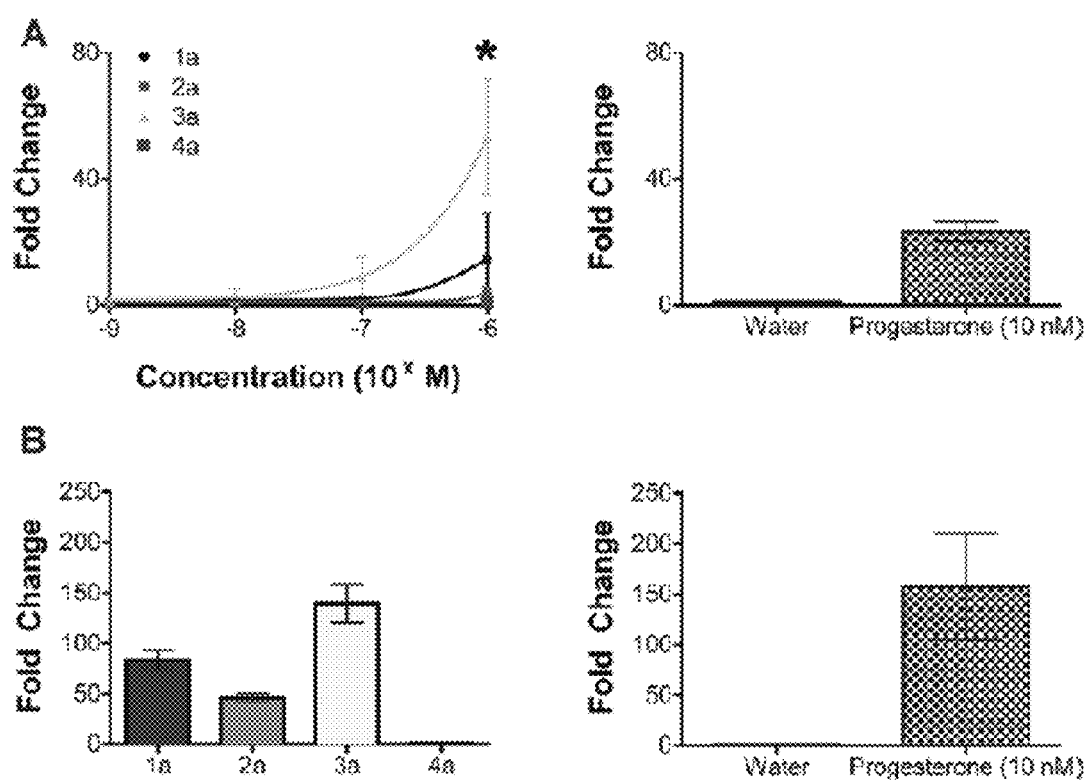
FIG. 17 shows progesterone Gd(III) chelates initiate gene transcription as described in Example 17. (A) Incubation with 3a resulted in the greatest transcriptional activation of luciferase reporter gene, while incubation with 4a resulted in no transcriptional activation (left). The asterisk denotes a significant difference in activation after incubation with 3a compared to 1a (at the highest incubation concentration, p<0.05, Student's t test). Activation with water or 10 nM progesterone is shown as a control (right). (B) Endogenous gene transcription is consistent with the luciferase assay. Induction of ZBTB16 was normalized to GAPDH. Error bars represent mean±standard deviation.

Progesterone receptors bind to a region of DNA referred to as the progesterone response element (PRE).(17) This DNA element was ligated to the luciferase gene and used to verify the ability of the compounds to cross the cell membrane and interact with PR to form a functional transcription complex. The change in luciferase activity at increasing incubation concentrations of each PR-targeted contrast agent is shown in FIG. 17a (left graph). The graph on the right in FIG. 17 shows the change in luciferase activity when cells were incubated with either water or 10 nM progesterone as a positive control. As expected, the control compound 4a did not induce PRE-mediated transcription to any significant extent. However, incubation with each of the progesterone derivatives resulted in luciferase activity, indicating that these compounds entered the cells and bound to PR as agonistic ligands. Interestingly, 3a was the most effective agent despite its low cell uptake and lower relative binding affinity for PR in vitro compared to 1a and 2a. Compound 2a demonstrated the lowest efficacy of the three progesterone-conjugated agents.

To further investigate the ability of the contrast agents to activate transcription, PR-regulation of the gene ZBTB16 was examined based on previous reports of its induction in T47D cells (FIG. 17b). The increase in ZBTB16 transcription in response to 1a-4a and progesterone was measured and normalized to GAPDH. Each progesterone-conjugated agent activated transcription after incubation at 10 nM, providing further evidence that these agents cross the cell membrane and bind to PR. Furthermore, the transcriptional activation demonstrated the same relative potency as the luciferase assays in that 3a demonstrated the highest activation of endogenous gene transcription. As expected, control agent 4a did not result in transcription of endogenous ZBTB16.

Water-Soluble MRI Contrast Agents Localize to the Cytoplasm

Figure 18:
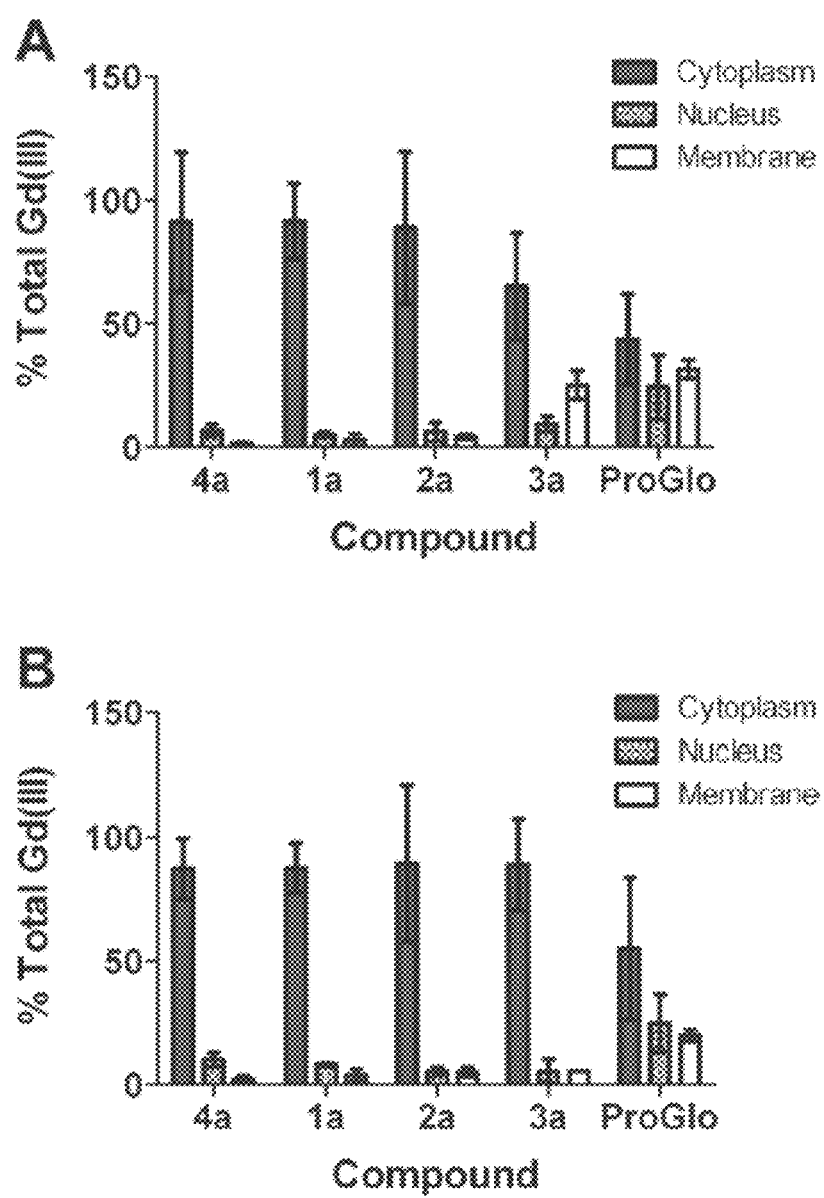
FIG. 18 shows results of tests of subcellular localization of the water-soluble PR-targeted agents, ProGlo, and nontargeted 4a in Example 17. (A) Subcellular localization in PR(+) T47D cells. (B) Subcellular localization in PR(−) MDA-MB-231 cells. Error bars represent mean±standard deviation. The water-soluble agents predominantly localized to the cytoplasm, whereas ProGlo was distributed in significant levels in the nucleus and membrane.

To examine the cellular distribution of the water-soluble PR-targeted agents as compared to 4a and ProGlo, PR(+) and PR(−) cells incubated with each agent were subjected to a nuclear cytoplasmic fractionation kit (FIG. 18). The pellet remaining after isolation of the nuclear and cytoplasmic fractions was assumed to contain material that was primarily associated with cell membrane proteins.

As expected, the majority of each agent was found in the cytoplasm of each cell type. However, the fraction of agent in the cytoplasm was lowest for ProGlo in both PR(+) and PR(−) cells. For 4a and the water-soluble PR-targeted agents, the fraction of agent in the cytoplasm was around 80-90% in both cell lines except for 3a, which showed a lower fraction in the cytoplasm of the PR(+) cells. The fraction of Gd(III) in the nucleus and membrane was similar for 4a and the water-soluble agents in both cell lines, although 3a had a higher presence in the pellet fraction in the PR(+) cells. ProGlo was found in high levels (relative to 1a-4-a) in the pellet and in the nucleus in both cell lines.

The majority of PR resides in the cytoplasm, but it was expected that incubation with the targeted contrast agents would result in translocation of a fraction of the total cytoplasmic receptor to the nucleus, leading to higher levels of Gd(III) in the nucleus after incubation with the targeted agents compared to 4a. While the luciferase assays and real-time PCR indicated that PR was activated, the difference in levels of progesterone-conjugated agents versus 4a that translocated to the nucleus was likely too low to detect using ICP-MS. However, the cell fractionation data indicate that in cells incubated with the water-soluble contrast agents, the majority of the Gd(III) associated with these cells is intracellular and not interacting within the membrane. While this was true for cells incubated with ProGlo, 20-30% of the total ProGlo was detected in the remaining membrane pellet fraction. The hydrophobicity of ProGlo likely increased nonspecific interaction with nontargeted biomolecules and could explain high levels of the agent in the membrane, as well as the higher levels in the nucleus compared to fractions from cells incubated with the water-soluble agents.

Water-Soluble Agents Demonstrate Lower Cytotoxicity than ProGlo

Figure 19:
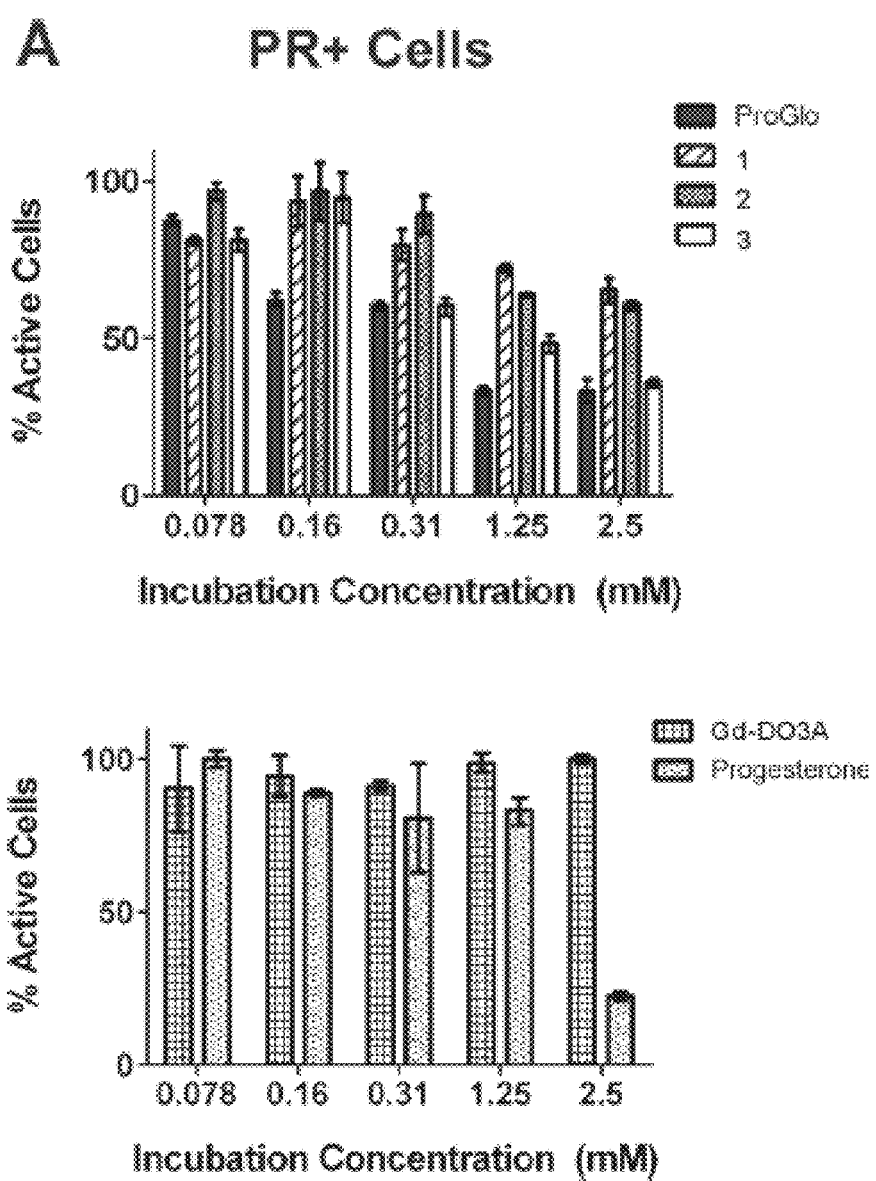
FIG. 19 shows the cytotoxicity of the PR-targeted agents (top graphs) compared to progesterone and nontargeted 4a (bottom graphs). (A) Cell viability in PR(+) T47D cells. (B) Cell viability in PR(−) MDAMB-231 cells. The water-soluble PR-targeted agents are associated with lower toxicity than ProGlo in both cell lines.
Figure 19:
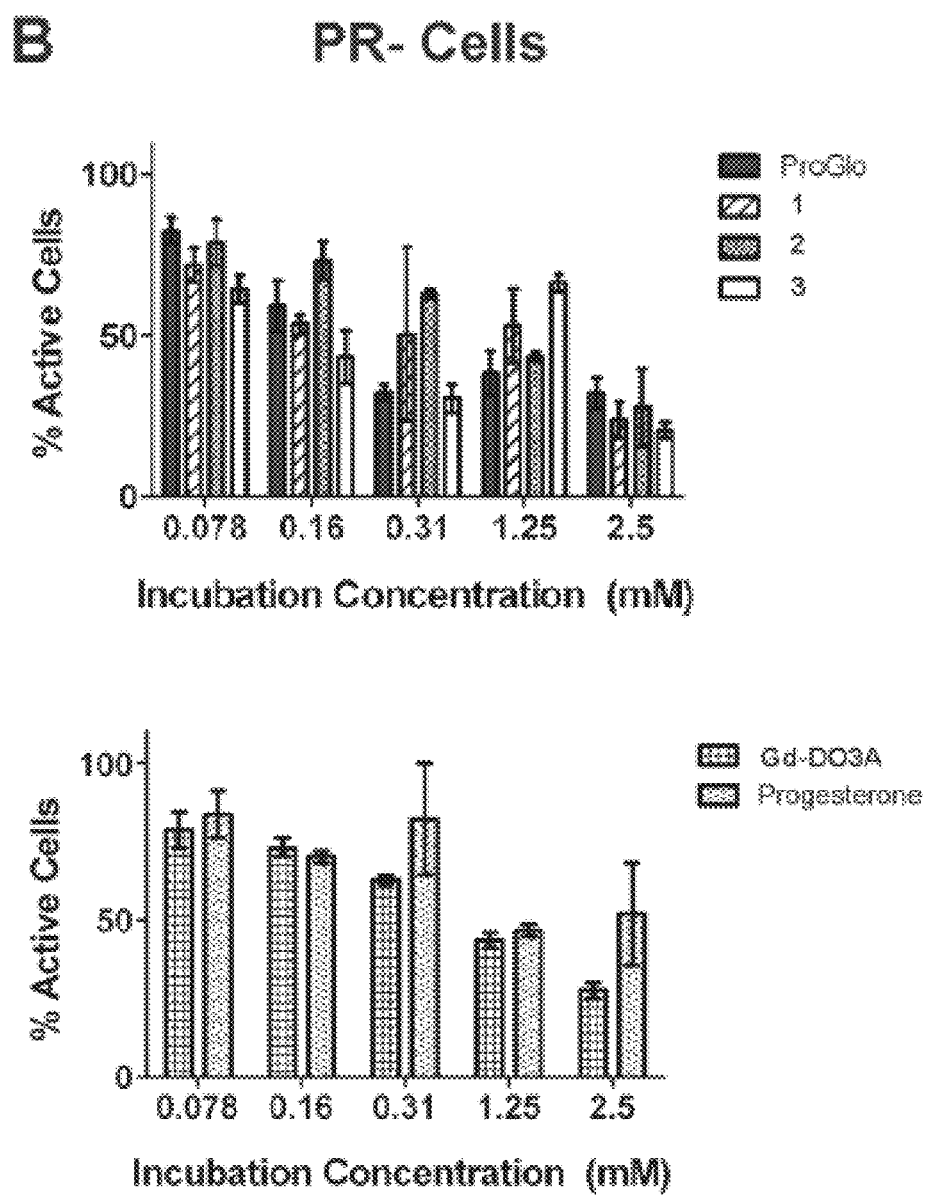

To determine the toxicity profile of the agents, a MTS assay of cell viability was conducted after incubating T47D or MDA-MB-231 cells with varying concentrations of each agent for a 24 h period. The toxicities of the water-soluble agents were compared to that of progesterone, ProGlo, and the nontargeted 4a, and the data are presented in FIG. 19.

As expected, in PR(+) T47D cells, the water-soluble PR-targeted agents were less toxic than ProGlo at all concentrations except for the lowest concentration tested. In addition, progesterone was more toxic than the water-soluble agents at the highest concentration tested (2.5 mM), but reached similar levels at 1.25 mM and lower. Control agent 4a was nontoxic at all concentrations tested. In PR(−) MDA-MB-231 cells, all agents had similar toxicity profiles, including 4a. While the effect on cell viability in both cell types was similar for ProGlo and progesterone, 4a and the water-soluble PR-targeted agents were surprisingly more toxic in the MDA-MB-231 cells than in the T47D cells. 3a was the most toxic of the water-soluble agents in both cell lines.

Water-Soluble Progesterone-Conjugated MRI Contrast Agents Specifically Enhance Contrast in PR(+) Preliminary Xenograft Images To determine whether the water-soluble progesterone-conjugated agents would increase the contrast-to-noise ratio (CNR) of PR(+) tumors relative to PR(−) tumors in vivo, athymic nude mice with PR(+) and PR(−) xenografted tumors were injected intraperitoneally with 1a, 2a, or 3a dissolved in DMSO and imaged at 2 and 6 h postinjection. Intraperitoneal injection was chosen over subcutaneous injection because it yielded more consistent results in previous studies, and the parent compound, ProGlo, has been more extensively studied for its biodistribution after intraperitoneal injection. (19) In addition, while these agents are water-soluble, they were dissolved in DMSO to compare back to previous in vivo imaging with the insoluble ProGlo and the control agent 4a.(19)

Figure 20:
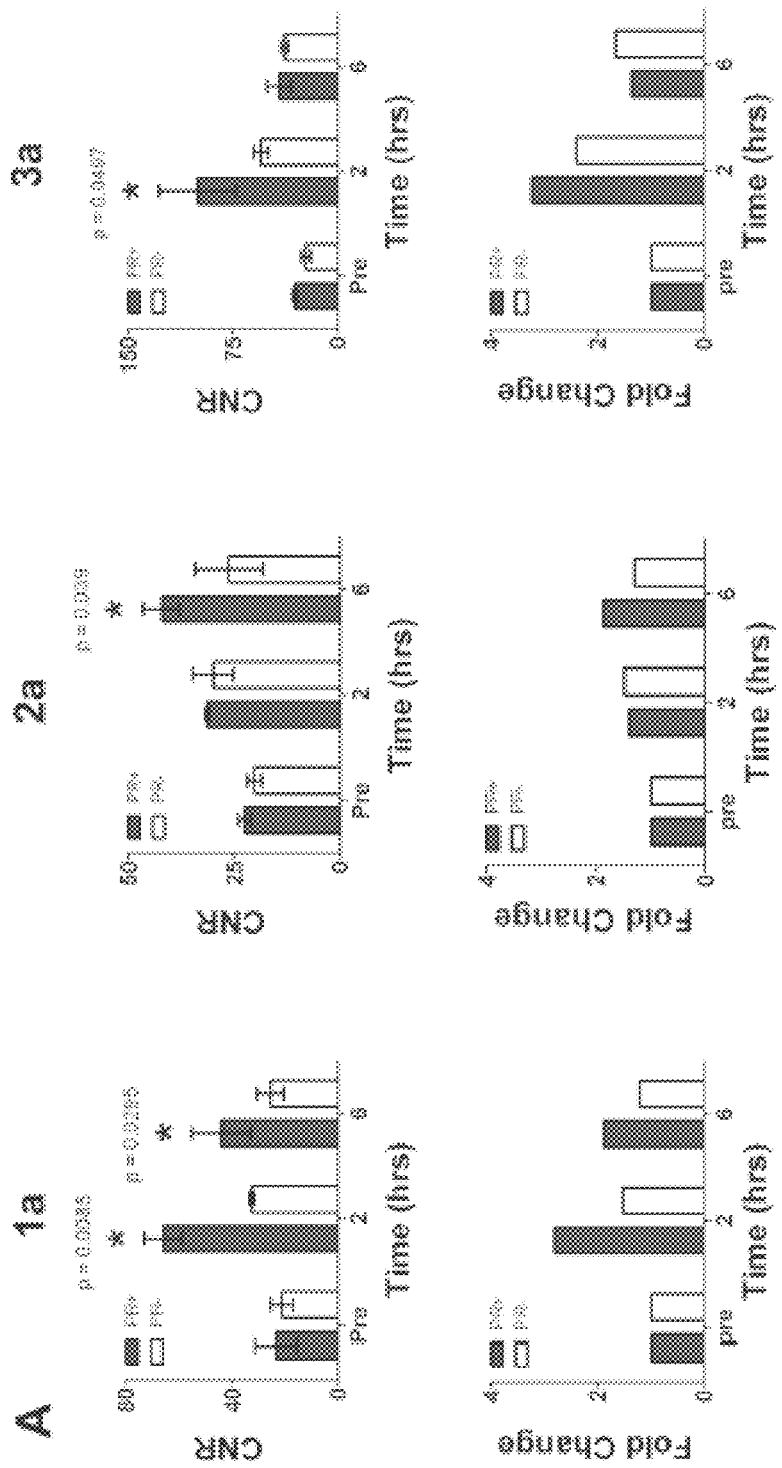
FIG. 20 shows xenograft images before and after injection of water-soluble agents. (A) Changes in contrast-to-noise ratio (CNR) in individual mice after intraperitoneal injection of 1a, 2a, or 3a (top graphs) and fold change in CNRs compared to preinjection CNR levels (bottom graphs). The water-soluble progesterone-conjugated agents preferentially enhanced CNR in the PR(+) tumors compared to the PR(−) tumors (asterisks, Student's t test p<0.05). Error bars represent±standard deviation of the mean. (B) Representative images of xenografted mice injected subcutaneously with 1a (top panels), 2a (middle panels), or 3a (bottom panels). White scale bars represent 5 mm.
Figure 20:
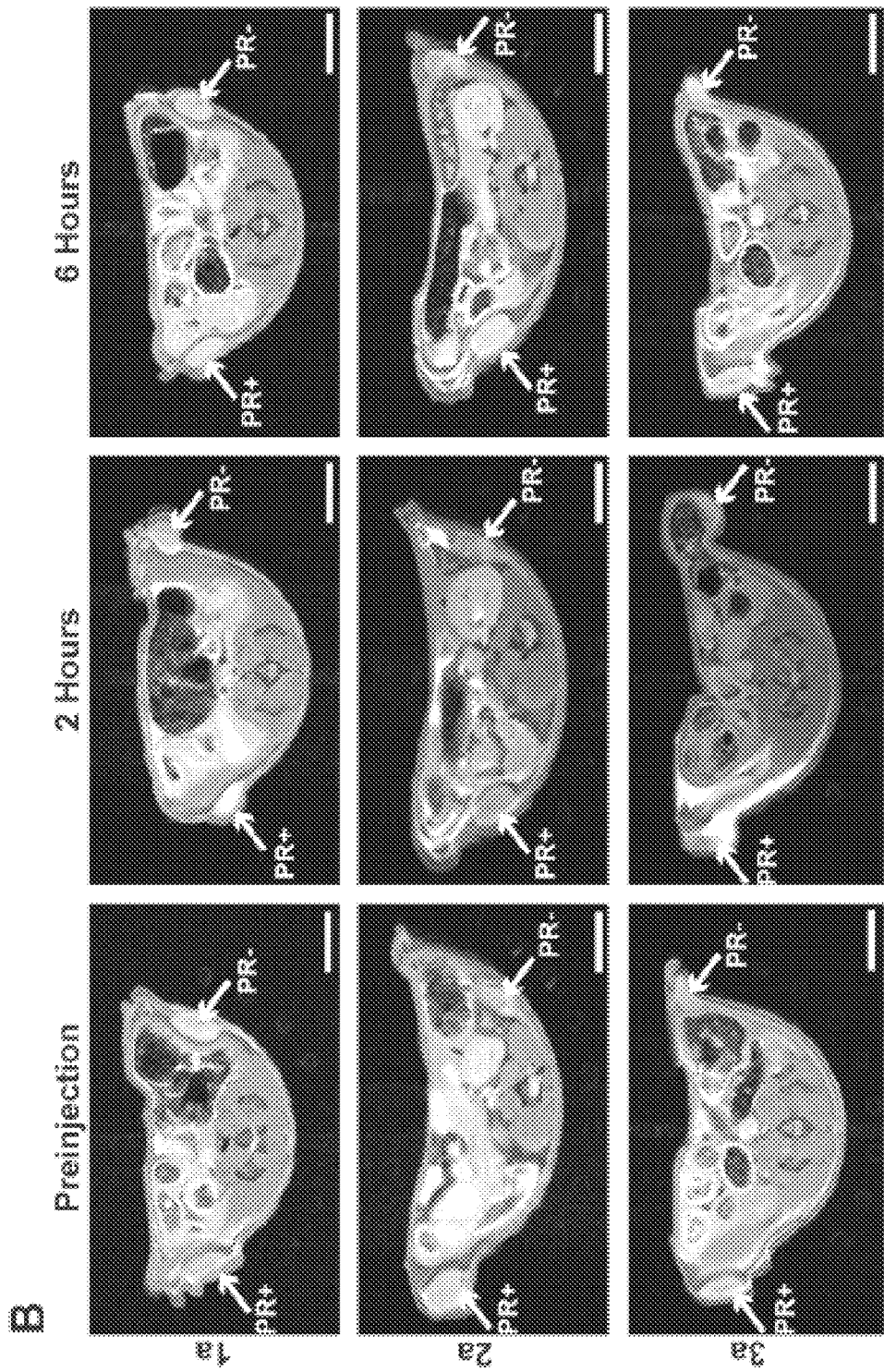

After injection of each of the PR-targeted agents, the PR(+) tumor exhibited significantly higher CNR than the PR(−) tumor at 6 h postinjection with 2a, 2 and 6 h postinjection with 1a, and 2 h postinjection with 3a (FIG. 20A, top graphs). At all other time points, the CNRs in the PR(+) and PR(−) were not significantly different. This is in contrast to the CNRs after injection with nontargeted 4a, in which the CNRs of the PR(+) and PR(−) tumors were not significantly different at any time point. (19) The uptake of these agents in the different tumor types can be partially attributed to PR-independent mechanisms, which would explain the presence of contrast agent in the PR(−) tumors. However, the increased CNR in the PR(+) compared to the PR(−) tumor is seen only with the progesterone-functionalized agents, indicating that the agents used here are targeting PR in vivo. Most likely, the higher accumulation in the PR(+) tumors is a result of accumulation and retention due to interaction with PR as previously reported(17) rather than PR-driven uptake of the agents.

Analysis of the xenograft images revealed that the PR-targeted agents each increased the CNR in both tumors over the preinjection CNR levels, particularly after injection of 1a and 3a (FIG. 20A, bottom graphs). Injection with ProGlo was previously reported to similarly increase CNR several-fold in both tumors, while injection with Gd-DO3A resulted in only minimal increases in CNR over time. Furthermore, the fold changes in CNR (compared to the preinjection CNR) in the PR(+) tumors after injection with 1a and 3a were 16% and 34% higher, respectively, at the 2 h time point than with ProGlo.(19) Injection with 3a resulted in the highest overall increase in CNR of the three agents, but 1a demonstrated a several-fold increase in CNR along with higher CNR in the PR(+) tumor than the PR(−) tumor at both the 2 and 6 h time points. These data provide evidence that the water-soluble PR-targeted probes function better as tumor imaging agents compared to nonfunctionalized 4a, and they preferentially target PR(+) cancer cells over PR(−) cancer cells (in similar fashion to ProGlo). Of the three water-soluble agents tested, 1a provided an optimal balance between tumor uptake and specificity for PR(+) cells compared to PR(−) cells. Representative images of the xenografts at each time point are shown in FIG. 20B.

Importantly, there was no observed toxicity associated with mice that were intraperitoneally injected with these water-soluble PR-targeted agents. Intraperitoneal injection with ProGlo had previously been associated with toxicity (xenografted mice injected with ProGlo in this manner became lethargic after the 6 h time point and did not survive to 24 h). (19) The mice injected with the water-soluble agents, however, remained active and survived to 24 h after injection with no changes in behavior.

Discussion

Steroid receptors such as PR correlate with disease prognosis and therapeutic efficacy in breast cancer.(5, 38) Receptor status is currently determined by immunohistochemistry assays of tumor biopsy samples, but noninvasive PR imaging agents would allow for improved molecular characterization, treatment decisions, and repeat analyses.(12) The hydrophobic PR-targeted ProGlo previously described demonstrated accumulation in, and consequent enhancement of, CNRs in PR-rich organs and tumors in vivo.(19) This example describes the synthesis and biological testing of several water-soluble compounds. These agents were associated with lower toxicity than ProGlo, but retained the ability to target PR in vitro and in preliminary in vivo experiments.

To decrease toxicity while maintaining PR targeting and biological activity, the structure of ProGlo was modified by using click chemistry to introduce a 1,2,3-triazole ring into the linker between progesterone and the Gd(III) chelate, which resulted in increased solubility. This triazole is spaced several carbons away from the steroid and did not interfere with receptor binding, as evidenced by the similar RBAs for these novel agents as compared to ProGlo. The induction of luciferase and endogenous progesterone-regulated ZBTB16 by each PR-targeted agent indicates that these agents crossed the cell membrane and bound to PR at biologically significant amounts. While the present invention is not limited to any particular mechanism and an understanding of the mechanism is not necessary to practice the invention, it may be that while 3a was not taken up well by cells, the ester may have hydrolyzed (due to the presence of esterases or via other mechanisms) to release 21-hydroxyprogesterone. This cleavage product would bind more strongly to PR and could explain the higher transcriptional activity observed after incubation with 3a.

The water-soluble progesterone-conjugated agents were less toxic than ProGlo due to their hydrophilic nature. The reduced toxicity is partially explained by decreased nonspecific interactions with these water-soluble agents as compared to ProGlo, as demonstrated by the cell fractionation experiments. ProGlo was distributed almost evenly across all the compartments analyzed, while the water-soluble agents were primarily located in the cytoplasm, indicating more nonspecific interaction between Proglo and off-target biomolecules. Incubation with 3a resulted in Gd(III) accumulation in the membrane of the PR(+) cells, possibly due to ester hydrolysis and subsequent production of a Gd(III) chelate with a pentanoic acid tail that could insert in cell membranes. While the present invention is not limited to any particular mechanism and an understanding of the mechanism is not necessary to practice the invention, this ester cleavage might explain the high signal intensity surrounding the PR(+) tumor in the in vivo images taken 2 h after injection with 3a, as well. In addition, ester hydrolysis would release 21-hydroxyprogesterone, which would enter the cells at high levels and could explain the higher cytotoxicity observed after incubation with this agent.

Studies in tumor xenografts demonstrated that 1a, 2a, and 3a preferentially enhanced CNR in PR(+) tumors as compared to PR(−) tumors at 2 and/or 6 h after injection. Injection of control agent 4a, by contrast, resulted in minimal changes in CNR at 2 and 6 h postinjection and no difference between the PR(+) and PR(−) tumors. Of these PR-targeted agents, 1a was the most promising in that it resulted in higher CNR in the PR(+) tumor than the PR(−) tumors at both 2 and 6 h postinjection. In addition, the fold change in CNR compared to preinjection levels was higher in the PR(+) tumor than the PR(−) tumor at both time points after injection. The accumulation of Gd(III) in these tumors may have been time-dependent. Injection with 1a and 3a increased CNR by 2 h, but CNR had decreased by 6 h. Injection with 2a, however, resulted in a slow increase in CNR over time. Interestingly, this pattern corresponded to the cellular accumulation in cells where 2a was the only agent tested that demonstrated time-dependent accumulation in PR(+) cells. Studies are ongoing to determine the optimal postinjection imaging time points for each of these agents.

The changes in CNR in the PR(+) tumor after injection of the water-soluble PR-targeted agents were comparable to or greater than the changes seen after injection of ProGlo previously demonstrated.(19) The difference between CNRs of the PR(+) and PR(−) tumors was greater after injection of these water-soluble agents than after intraperitoneal injection of ProGlo, indicating that these agents possibly have more bioavailability due to their enhanced solubility. Finally, these water-soluble agents were associated with less in vivo toxicity than ProGlo. The enhanced solubility and bioavailability combined with the decreased toxicity might both be attributed to the less hydrophobic nature of these agents.

Recent reports have asserted that, although there has been a focus on developing drugs that accumulate in cancer cells, this accumulation might actually prevent drugs from penetrating deep within tumors and decrease their efficacy.(40-42) Drugs that accumulate quickly within cells tend not to penetrate deeper areas of tumors, while less cell-permeable drugs travel further within the tumor and are more effective. (42) This indicates that decreasing lipophilicity of the agent would reduce cellular accumulation and allow for improved tumor penetration. The ability to inject water-soluble agents intravenously would also increase tumor penetration, as the angiogenic vasculature of the tumor would likely leak the agent allowing for accumulation. For imaging agents, this property of tumor penetration would be important in terms of measuring receptor levels in a tumor with heterogeneous receptor distribution.(43) The PR-targeted agents described here would likely penetrate tumors better than ProGlo and increase signal intensity of the entire tumor rather than the surface especially since it can only be administered intraperitoneally or subcutaneously.

As described above, a series of water-soluble PR-targeted MRI contrast agents were designed and synthesized. These agents crossed cell membranes PR(+) T47D cells and activated PR at biologically relevant levels but exhibited lower in vitro and in vivo toxicity than the more hydrophobic ProGlo. Finally, these progesterone-conjugated agents enhanced CNR in PR(+) tumors as compared to PR(−) tumors in imaging studies in xenografts References (All of Which are Herein Incorporated by Reference)

1. Gambhir, S. S. (2002) Molecular imaging of cancer with positron emission tomography Nat. Rev. Cancer 2, 683-693.
2. Weissleder, R. (2002) Scaling down imaging: molecular mapping of cancer in mice Nat. Rev. Cancer 2, 11-18.
3. Weissleder, R. (2006) Molecular imaging in cancer Science 312, 1168-1171.
4. Pysz, M. A., Gambhir, S. S., and Willmann, J. K. (2010) Molecular imaging: current status and emerging strategies Clin. Radiol. 65, 500-516.
5. Ahmad, N. and Kumar, R. (2011) Steroid hormone receptors in cancer development: a target for cancer therapeutics Cancer Lett. 300, 1-9.
6. Benard, F. and Turcotte, E. (2005) Imaging in breast cancer: Single-photon computed tomography and positron-emission tomography Breast Cancer Res. 7, 153-162.

7. Linden, H. M., Stekhova, S. A., Link, J. M., Gralow, J. R., Livingston, R. B., Ellis, G. K., Petra, P. H., Peterson, L. M., Schubert, E. K., Dunnwald, L. K., Krohn, K. A., and Mankoff, D. A. (2006) Quantitative fluoroestradiol positron emission tomography imaging predicts response to endocrine treatment in breast cancer J. Clin. Oncol. 24, 2793-2799.

8. Yoshida, Y., Kurokawa, T., Sawamura, Y., Shinagawa, A., Okazawa, H., Fujibayashi, Y., and Kotsuji, F. (2007) The positron emission tomography with F18 17beta-estradiol has the potential to benefit diagnosis and treatment of endometrial cancer Gynecol. Oncol. 104, 764-766.

9. Dehdashti, F., Picus, J., Michalski, J. M., Dence, C. S., Siegel, B. A., Katzenellenbogen, J. A., and Welch, M. J. (2005) Positron tomographic assessment of androgen receptors in prostatic carcinoma Eur. J. Nucl. Med. Mol. Imaging. 32, 344-350.

10. Roy, F.-N., Croteau, E., Ouellet, R., Bujold, R., Forget, A., Dufresne, J., van Lier, J., and Benard, F. (2010) Predictive value of (16 alpha[18-F]-fluoroestradiol) FES-PET in recurrent estrogen receptor positive (ER+) breast cancer J. Nucl. Med. Meeting Abstr. 51, 56.

11. Katzenellenbogen, J. A., Zhou, H. B., Lee, J. H., Mayne, C. G., and Carlson, K. E. (2010) Imaging progesterone receptor in breast tumors: synthesis and receptor binding affinity of fluoroalkyl-substituted analogues of Tanaproget J. Med. Chem. 53, 3349-3360.

12. Lee, J. H., Zhou, H. B., Dence, C. S., Carlson, K. E., Welch, M. J., and Katzenellenbogen, J. A. (2010) Development of [F-18]fluorine-substituted Tanaproget as a progesterone receptor imaging agent for positron emission tomography Bioconjugate Chem. 21, 1096-1104.

13. Verhagen, A., Studeny, M., Luurtsema, G., Visser, G. M., De Goeij, C. C., Sluyser, M., Nieweg, O. E., Van der Ploeg, E., Go, K. G., and Vaalburg, W. (1994) Metabolism of a [18F]fluorine labeled progestin (21-[18F]fluoro-16 alpha-ethyl-19-norprogesterone) in humans: a clue for future investigations Nucl. Med. Biol. 21, 941-52.

14. Frullano, L. and Meade, T. J. (2007) Multimodal MRI contrast agents J. Biol. Inorg. Chem. 12, 939-949.

15. Major, J. L. and Meade, T. J. (2009) Bioresponsive, cell-penetrating, and multimeric MR contrast agents Acc. Chem. Res. 42, 893-903.

16. Lee, J., Zylka, M. J., Anderson, D. J., Burdette, J. E., Woodruff, T. K., and Meade, T. J. (2005) A steroid-conjugated contrast agent for magnetic resonance imaging of cell signaling J. Am. Chem. Soc. 127, 13164-13166.

17. Lee, J., Burdette, J. E., MacRenaris, K. W., Mustafi, D., Woodruff, T. K., and Meade, T. J. (2007) Rational design, synthesis, and biological evaluation of progesterone-modified MRI contrast agents Chem. Biol. 14, 824-834.

18. Saha, P., Hodl, C., Strauss, W. S. L., Steiner, R., Goessler, W., Kunert, O., Leitner, A., Haslinger, E., and Schramm, H. W. (2010) Synthesis, in vitro progesterone receptors affinity of gadolinium containing mifepristone conjugates and estimation of binding sites in human breast cancer cells Bioorg. Med. Chem. 18, 1891-1898.

19. Sukerkar, P. A., Macrenaris, K. W., Meade, T. J., and Burdette, J. E. (2011) A steroid-conjugated magnetic resonance probe enhances contrast in progesterone receptor expressing organs and tumors in vivo Mol. Pharmaceutics. 8, 1390-1400.

20. Couture, J. F., Legrand, P., Cantin, L., Luu-The, V., Labrie, F., and Breton, R. (2003) Human 20alpha-hydroxysteroid dehydrogenase: crystallographic and site-directed mutagenesis studies lead to the identification of an alternative binding site for C21-steroids J. Mol. Biol. 331, 593-604.

21. Leo, A., Hansch, C., and Elkins, D. (1971) Partition coefficients and their uses Chem. Rev. 71, 525-616.

22. Leo, A. J. (1987) Some advantages of calculating octanol-water partition coefficients J. Pharm. Sci. 76, 166-168.

23. Price, D. A., Blagg, J., Jones, L., Greene, N., and Wager, T. (2009) Physicochemical drug properties associated with in vivo toxicological outcomes: a review Expert Opin. Drug Metab. Toxicol. 5, 921-931.

24. Beeby, A., Clarkson, I. M., Dickins, R. S., Faulkner, S., Parker, D., Royle, L., de Sousa, A. S., Williams, J. A. G., and Woods, M. (1999) Non-radiative deactivation of the excited states of europium, terbium and ytterbium complexes by proximate energy-matched OH, NH and CH oscillators: an improved luminescence method for establishing solution hydration states J. Chem. Soc., Perkin Trans. 2 493-504.

25. Quici, S., Cavazzini, M., Marzanni, G., Accorsi, G., Armaroli, N., Ventura, B., and Barigelletti, F. (2005) Visible and near-infrared intense luminescence from water-soluble lanthanide [Tb(III), Eu(III), Sm(III), Dy(III), Pr(III), Ho(III), Yb(III), Nd(III), Er(III)] complexes Inorg. Chem. 44, 529-537.

26. Williams, S. P. and Sigler, P. B. (1998) Atomic structure of progesterone complexed with its receptor Nature 393, 392-396

27. Madauss, K. P., Deng, S. J., Austin, R. J., Lambert, M. H., McLay, I., Pritchard, J., Short, S. A., Stewart, E. L., Uings, I. J., and Williams, S. P. (2004) Progesterone receptor ligand binding pocket flexibility: crystal structures of the norethindrone and Mometasone furoate complexes J. Med. Chem. 47, 3381-3387.

28. Kolb, H. C., Finn, M. G., and Sharpless, K. B. (2001) Click chemistry: diverse chemical function from a few good reactions Angew. Chem., Int. Ed. Engl. 40, 2004-2021.

29. Tornoe, C. W., Christensen, C., and Meldal, M. (2002) Peptidotriazoles on solid phase: [1,2,3]-triazoles by regiospecific copper(i)-catalyzed 1,3-dipolar cycloadditions of terminal alkynes to azides J. Org. Chem. 67, 3057-3064.

30. Song, Y., Kohlmeir, E. K., and Meade, T. J. (2008) Synthesis of multimeric MR contrast agents for cellular imaging J. Am. Chem. Soc. 130, 6662-6663.

31. Viguier, R. F. and Hulme, A. N. (2006) A sensitized europium complex generated by micromolar concentrations of copper(I): toward the detection of copper(I) in biology J. Am. Chem. Soc. 128, 11370-11371.

32. Prasuhn, D. E., Jr., Yeh, R. M., Obenaus, A., Manchester, M., and Finn, M. G. (2007) Viral MRI contrast agents: coordination of Gd by native virions and attachment of Gd complexes by azide-alkyne cycloaddition Chem. Commun. (Camb.) 1269-1271.

33. Stasiuk, G. J. and Lowe, M. P. (2009) Click chemistry with lanthanide complexes: a word of caution Dalton Trans. 9725-9727.

34. Lebedev, A. Y., Holland, J. P., and Lewis, J. S. (2010) Clickable bifunctional radiometal chelates for peptide labeling Chem. Commun. (Camb.) 46, 1706-1708.

35. Caravan, P., Ellison, J. J., McMurry, T. J., and Lauffer, R. B. (1999) Gadolinium(III) chelates as MRI contrast agents: structure, dynamics, and applications Chem. Rev. 99, 2293-2352.

36. Meade, T. J., Taylor, A. K., and Bull, S. R. (2003) New magnetic resonance contrast agents as biochemical reporters Curr. Opin. Neurobiol. 13, 597-602.
37. Leeson, P. D. and Springthorpe, B. (2007) The influence of drug-like concepts on decision-making in medicinal chemistry Nat. Rev. Drug Discovery 6, 881-890.
38. Orlando, L., Schiavone, P., Fedele, P., Calvani, N., Nacci, A., Rizzo, P., Marino, A., D'Amico, M., Sponziello, F., Mazzoni, E., Cinefra, M., Fazio, N., Maiello, E., Silvestris, N., Colucci, G., and Cinieri, S. (2010) Molecularly targeted endocrine therapies for breast cancer Cancer Treat. Rev. 36 (Suppl 3) S67-S71.
39. Marik, J. and Sutcliffe, J. L. (2006) Click for PET: rapid preparation of [18F]fluoropeptides using CuI catalyzed 1,3-dipolar cycloaddition Tetrahedron Lett. 47, 6681-6684.
40. Tunggal, J. K., Cowan, D. S., Shaikh, H., and Tannock, I. F. (1999) Penetration of anticancer drugs through solid tissue: a factor that limits the effectiveness of chemotherapy for solid tumors Clin. Cancer Res. 5, 1583-1586.
41. Minchinton, A. I. and Tannock, I. F. (2006) Drug penetration in solid tumours Nat. Rev. Cancer 6, 583-592.
42. Bryce, N. S., Zhang, J. Z., Whan, R. M., Yamamoto, N., and Hambley, T. W. (2009) Accumulation of an anthraquinone and its platinum complexes in cancer cell spheroids: the effect of charge on drug distribution in solid tumour models Chem. Commun. (Camb.) 2673-2675.
43. Mankoff, D. A., Link, J. M., Linden, H. M., Sundararajan, L., and Krohn, K. A. (2008) Tumor receptor imaging J. Nucl. Med. 49 (Suppl 2) 149S-163S.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:
1. A composition comprising an MRI contrast agent, wherein said MRI contrast agent comprises:
   a) a ligand moiety, wherein said ligand moiety comprises progesterone,
   b) a contrast moiety comprising M-DO3A, wherein the structure of said M-DO3A is as follows:

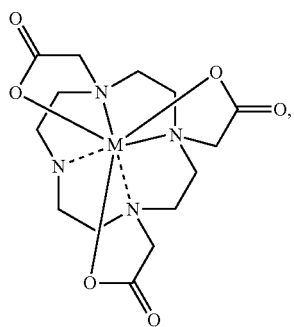

wherein M is a paramagnetic metal ion selected from the group consisting of: Gd(III), Fe(III), Mn(II), Y(III), Cr(III), Eu(III), and Dy(III), and
   c) a linkage region, wherein said linkage region comprises a triazole ring, wherein said linkage region covalently links said ligand moiety to said contrast moiety, and wherein said linkage region is directly attached to said ligand moiety and said contrast moiety, and
   wherein said MRI contrast agent is water soluble.

2. The composition of claim 1, wherein said paramagnetic metal ion is selected from the group comprising Gd(III) and Eu(III).

3. The composition of claim 1, wherein said paramagnetic metal ion comprises Gd(III).

4. The composition of claim 1, wherein said linker region further comprises one or more methylene carbons.

5. The composition of claim 4, wherein said linker region comprises 3 or 6 methylene carbons.

6. A method comprising:
   a) administering a composition of claim 1 to a cell or tissue; and
   b) producing a magnetic resonance image of said cell or tissue.

7. The method of claim 6, wherein said cell or tissue expresses progesterone receptor.

8. The method of claim 7, wherein said progesterone binds to said progesterone receptor.

9. The method of claim 8, wherein binding of said progesterone to said progesterone receptor results in localization of said composition.

10. The method of claim 6, wherein said cell or tissue does not express progesterone receptor.

* * * * *